United States Patent
McNaughton et al.

(10) Patent No.: US 10,538,556 B2
(45) Date of Patent: Jan. 21, 2020

(54) ANTI-HIV PEPTIDES

(71) Applicants: Colorado State University Research Foundation, Fort Collins, CO (US); University of Rochester, Rochester, NY (US)

(72) Inventors: Brian R. McNaughton, Fort Collins, CO (US); David W. Crawford, Fort Collins, CO (US); Joseph E. Wedekind, Rochester, NY (US); Ivan A. Belashov, Rochester, NY (US)

(73) Assignees: Colorado State University Research Foundation, Fort Collins, CO (US); University of Rochester, Rochester, NY (US)

( * ) Notice: Subject to any disclaimer, the term of this patent is extended or adjusted under 35 U.S.C. 154(b) by 0 days.

(21) Appl. No.: 15/805,933

(22) Filed: Nov. 7, 2017

(65) Prior Publication Data
US 2018/0127468 A1    May 10, 2018

Related U.S. Application Data

(60) Provisional application No. 62/418,529, filed on Nov. 7, 2016.

(51) Int. Cl.
| | |
|---|---|
| *A61K 38/00* | (2006.01) |
| *A61K 38/03* | (2006.01) |
| *A61K 38/04* | (2006.01) |
| *A61K 38/10* | (2006.01) |
| *A61P 31/18* | (2006.01) |
| *C07K 7/06* | (2006.01) |
| *C07K 7/08* | (2006.01) |
| *C07K 7/50* | (2006.01) |
| *C07K 7/64* | (2006.01) |
| *C07K 7/00* | (2006.01) |
| *C07K 11/00* | (2006.01) |
| *C07K 14/00* | (2006.01) |

(52) U.S. Cl.
CPC ............ *C07K 7/64* (2013.01); *A61P 31/18* (2018.01); *C07K 7/06* (2013.01); *C07K 7/08* (2013.01); *C07K 7/50* (2013.01); *A61K 38/00* (2013.01)

(58) Field of Classification Search
CPC ........ A61K 38/00; A61K 38/03; A61K 38/04; A61K 38/10; C07K 7/06; C07K 7/08; C07K 7/50; C07K 7/64; C07K 7/00; C07K 11/00; C07K 14/00; A61P 31/18

USPC ...... 514/3.7, 3.8, 3.6, 21.5, 21.4, 21.3, 21.2, 514/21.1; 530/388.35, 388.3, 327, 326, 530/325, 324, 300
See application file for complete search history.

(56) References Cited

U.S. PATENT DOCUMENTS

| | | | |
|---|---|---|---|
| 5,646,120 A | 7/1997 | Sumner-Smith et al. | |
| 8,889,394 B2* | 11/2014 | Chalasani | C07K 14/4702 435/199 |
| 2016/0282347 A1* | 9/2016 | Irminger-Finger | C07K 14/47 |

FOREIGN PATENT DOCUMENTS

FR    2792204 A1    10/2000

OTHER PUBLICATIONS

Adessi et al, "Coverting a Peptide into a Drug: Strategies to Improve Stability and Bioavailability," Current Medicinal Chemistry, 2002, 9: 963-978.*
Crawford DW et al. An Evolved RNA Recognition Motif that Suppresses HIV-1 Tat/TAR-Dependent Transcription. ACS Chem Biol. Aug. 19, 2016;11(8):2206-2215.
Davidson A et al. Simultaneous recognition of HIV-1 TAR RNA bulge and loop sequences by cyclic peptide mimics of Tat protein. Proceedings National Academy of Sciences PNAS. Jul. 21, 2009;106(29):11931-11936.
Fu J et al. Design-Based Peptidomimetic Ligand Discovery to Target HIV TAR RNA Using Comparative Analysis of Different Docking Methods. Current HIV Research. 2016;14(6):476-483.
International Search Report and Written Opinion, PCT/US2017/060400, dated Feb. 8, 2018.
Li CH et al. The interactions and recognition of cyclic peptide mimetics of Tat with HIV-1 TAR RNA: a molecular dynamics simulation study. Journal of Biomolecular Structure and Dynamics. Mar. 1, 2013;31(3):276-287.
Xie B et al. Selection of TAR RNA-Binding Chameleon Peptides by Using a Retroviral Replication System. Journal of Virology. Feb. 2004;78(3):1456-1463.

* cited by examiner

*Primary Examiner* — Julia Ha
(74) *Attorney, Agent, or Firm* — Polsinelli PC

(57) ABSTRACT

Simple β-hairpin peptides in linear and cyclic form that specifically bind to HIV-1 Trans-Activation Response element (HIV-1 TAR), as well as compositions and use thereof are described.

34 Claims, 11 Drawing Sheets
(9 of 11 Drawing Sheet(s) Filed in Color)
Specification includes a Sequence Listing.

| SEQ ID NO | β2β3 loop sequences at given positions | | | | | | | | | | | | | | | | | | | |
|---|---|---|---|---|---|---|---|---|---|---|---|---|---|---|---|---|---|---|---|---|
| 1 |   |   |   | L | D | I | L | V | S | R | S | L | K | M | R | G | Q | A | F | V | I | F |
| 2 |   |   |   |   |   |   | X | X | P | R | X1 | R | X2 | X3 | R | K | X | X | X |   |   |
| 3 |   |   |   |   |   |   | X | X | P | R | X1 | R | X2 | X3 | R | K | X | X | X |   |   |
| 4 |   |   |   |   |   |   | X | X | P | R | T | R | T | P | R | K | X | X | X |   |   |
| 5 | K | X | X | X | X | P | R | X1 | R | X2 | X3 | R | K | X | X | X | X | X | X |
| 6 | K | X | X | X | X | P | R | X1 | R | X2 | X3 | R | K | X | X | X | X | X | X |
| 7 | X | X | X | X | X | P | R | T | R | T | P | R | K | X | X | X | X | X | X |
| 8 | L | D | I | L | V | P | R | H | R | T | P | R | G | Q | A | F | V | I | F |
| 9 | L | D | I | L | V | P | R | K | R | T | P | R | G | Q | A | F | V | I | F |
| 10 | L | D | I | L | V | P | R | M | R | R | P | R | G | Q | A | F | V | I | F |
| 11 | L | D | I | L | V | P | R | M | R | T | P | R | G | Q | A | F | V | I | F |
| 12 | L | D | I | L | V | P | R | P | R | R | P | R | G | Q | A | F | V | I | F |
| 13 | L | D | I | L | V | P | R | P | R | T | P | R | G | Q | A | F | V | I | F |
| 14 | L | D | I | L | V | P | R | P | R | T | Y | R | G | Q | A | F | V | I | F |
| 15 | L | D | I | L | V | P | R | Q | R | T | P | R | G | Q | A | F | V | I | F |
| 16 | L | D | I | L | V | P | R | R | R | Q | P | R | G | Q | A | F | V | I | F |
| 17 | L | D | I | L | V | P | R | R | R | T | P | R | G | Q | A | F | V | I | F |
| 18 | L | D | I | L | V | P | R | R | R | T | W | R | G | Q | A | F | V | I | F |
| 19 | L | D | I | L | V | P | R | R | R | T | Y | R | G | Q | A | F | V | I | F |
| 20 | L | D | I | L | V | P | R | T | R | N | P | R | G | Q | A | F | V | I | F |
| 21 | L | D | I | L | V | P | R | T | R | R | P | R | G | Q | A | F | V | I | F |
| 22 | L | D | I | L | V | P | R | T | R | T | P | R | G | Q | A | F | V | I | F |
| 23 | L | D | I | L | V | P | R | T | R | V | P | R | G | Q | A | F | V | I | F |
| 24 | L | D | I | L | V | P | R | Y | R | T | P | R | G | Q | A | F | V | I | F |

SEQ ID NO: 2 - X is any amino acid; X1 is T, N, Q, K, R, or H; X2 is T, N, Q, S, R, or H; X3 is P, Y, W, F, L, I, V, or A
SEQ ID NO: 3 - X is any amino acid; X1 is T, N, or Q; X2 is T, N, Q, or S; X3 is P, Y, W, F
SEQ ID NO: 4 - X is any amino acid
SEQ ID NO: 5 - X is any amino acid; X1 is T, N, Q, K, R, or H; X2 is T, N, Q, S, R, or H; X3 is P, Y, W, F, L, I, V, or A
SEQ ID NO: 6 - X is any amino acid; X1 is T, N, or Q; X2 is T, N, Q, or S; X3 is P, Y, W, F
SEQ ID NO: 7 - X is any amino acid

ANTI-HIV PEPTIDES

CROSS REFERENCE TO RELATED APPLICATIONS

This application claims the benefit of U.S. provisional application No. 62/418,529, filed Nov. 7, 2016, the disclosure of which is hereby incorporated by reference in its entirety.

GOVERNMENTAL RIGHTS

This invention was made with government support under GM107520 awarded by the National Institutes of Health. The government has certain rights in the invention.

FIELD OF THE INVENTION

The present disclosure provides simple β-hairpin peptides in linear and cyclic form that specifically bind to HIV-1 Trans-Activation Response element (HIV-1 TAR), as well as compositions and use thereof.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

HIV/AIDS afflicts nearly 37 million people worldwide. At present there is no cure or vaccine. New antivirals must be developed to combat drug resistance, while addressing the needs of an aging population requiring decades of therapy compliance. Existing FDA-approved drugs target many facets of the viral life cycle. To improve long-term therapeutic outcome, modulation of new targets—especially those resistant to mutation—is needed.

The HIV-1 Trans-Activation Responsive element (TAR) is highly resistant to mutation and plays important roles in facilitating proviral transcription and blocking apoptosis of the infected host cell. Despite its central importance in the HIV life cycle, TAR has been refractory to the discovery of small-molecules or peptides with sufficient affinity and selectivity to warrant pharmaceutical development. Crawford et al. described 70 different proteins, referred to as TAR binding proteins (TBPs), that specifically recognize TAR through combined interactions of the N- and C-terminal helix present in each TBP (Crawford et al. *ACS Chem Biol*, 2016, 11(8): 2206-2215). However, due to the size of these proteins, pharmaceutical development is not ideal.

Thus, there remains a need in the art for new HIV therapeutics.

SUMMARY OF THE INVENTION

In an aspect, the present disclosure encompasses an isolated peptide consisting of an amino acid sequence of SEQ ID NO: 2, or a derivative or a conjugate thereof, wherein the isolated peptide, derivative, or conjugate specifically binds to HIV-1 trans-activation responsive RNA. The peptide can be linear or cyclic. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptides.

In another aspect, the present disclosure encompasses an isolated peptide consisting of an amino acid sequence of SEQ ID NO: 3, or a derivative or a conjugate thereof, wherein the isolated peptide, derivative, or conjugate specifically binds to HIV-1 trans-activation responsive RNA. The peptide can be linear or cyclic. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses an isolated peptide consisting of an amino acid sequence of SEQ ID NO: 4, or a derivative or a conjugate thereof, wherein the isolated peptide, derivative, or conjugate specifically binds to HIV-1 trans-activation responsive RNA. The peptide can be linear or cyclic. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses an isolated peptide consisting of residues 4 to 16 of an amino acid sequence selected from the group SEQ ID NO: 8 to SEQ ID NO: 24, or a derivative or a conjugate thereof, wherein the isolated peptide, derivative, or conjugate specifically binds to HIV-1 trans-activation responsive RNA. The peptide can be linear or cyclic. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses an isolated peptide consisting of an amino acid sequence of SEQ ID NO: 5, or a derivative or a conjugate thereof, wherein the isolated peptide, derivative, or conjugate specifically binds to HIV-1 trans-activation responsive RNA. The peptide can be linear or cyclic. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses an isolated peptide consisting of an amino acid sequence of SEQ ID NO: 6, or a derivative or a conjugate thereof, wherein the isolated peptide, derivative, or conjugate specifically binds to HIV-1 trans-activation responsive RNA. The peptide can be linear or cyclic. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses an isolated peptide consisting of an amino acid sequence of SEQ ID NO: 7, or a derivative or a conjugate thereof, wherein the isolated peptide, derivative, or conjugate specifically binds to HIV-1 trans-activation responsive RNA. The peptide can be linear or cyclic. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses an isolated peptide selected from the group SEQ ID NO: 8 to SEQ ID NO: 24, or a derivative or a conjugate thereof, wherein the isolated peptide, derivative, or conjugate specifically binds to HIV-1 trans-activation responsive RNA. The peptide can be linear or cyclic. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses a cyclic peptide comprising an amino acid sequence of SEQ ID NO: 2, or a derivative or a conjugate thereof. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses a cyclic peptide comprising an amino acid sequence of SEQ ID NO: 3, or a derivative or a conjugate thereof. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses a cyclic peptide comprising an amino acid sequence of SEQ ID NO: 4, or a derivative or a conjugate thereof. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses a cyclic peptide comprising residues 4 to 16 of an amino acid selected from the group SEQ ID NO: 8 to SEQ ID NO: 24, or a derivative or a conjugate thereof. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses a cyclic peptide comprising an amino acid sequence of SEQ ID NO: 5, or a derivative or a conjugate thereof. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses a cyclic peptide comprising an amino acid sequence of SEQ ID NO: 6, or a derivative or a conjugate thereof. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses a cyclic peptide comprising an amino acid sequence of SEQ ID NO: 7, or a derivative or a conjugate thereof. The peptide can be cyclized by head-to-tail cyclization, side chain-to-tail cyclization, head-to-side chain cyclization, or side chain-to-side chain cyclization. The present disclosure also encompasses pharmaceutical compositions comprising said peptide.

In another aspect, the present disclosure encompasses a cyclic peptide comprising an amino acid sequence selected from the group SEQ ID NO: 8 to SEQ ID NO: 24, or a derivative or a conjugate thereof. The peptide can be cyclized by head-to-tail cyclization, side chain-to-tail cycliza-tion, head-to-side chain cyclization, or side chain-to-side chain cyclization. The present disclosure also encompasses pharmaceutical compositions comprising said peptide.

In another aspect, the present disclosure encompasses a method of inhibiting the interaction between HIV Tat and HIV TAR, the method comprising contacting an HIV infected cell with a linear or cyclic peptide disclosed herein.

In another aspect, the present disclosure encompasses a method of reducing HIV proliferation, the method comprising contacting an HIV infected cell with a linear or cyclic peptide disclosed herein.

In another aspect, the present disclosure encompasses a method for treating or preventing an HIV infection, the method comprising administering to a subject in need thereof a pharmaceutical composition comprising an effective amount of a linear or cyclic peptide disclosed herein.

In another aspect, the present disclosure encompasses a method for treating or preventing a disease or disorder involving HIV, the method comprising administering to a subject in need thereof a pharmaceutical composition comprising an effective amount of a linear or cyclic peptide disclosed herein.

Other aspects and iterations of the invention are described more thoroughly below.

BRIEF DESCRIPTION OF THE FIGURES

The application file contains at least one photograph executed in color. Copies of this patent application publication with color photographs will be provided by the Office upon request and payment of the necessary fee.

FIG. 8 depicts the relationship between SEQ ID NO: 1 to 24.

DETAILED DESCRIPTION

Figures 1A, 1B:
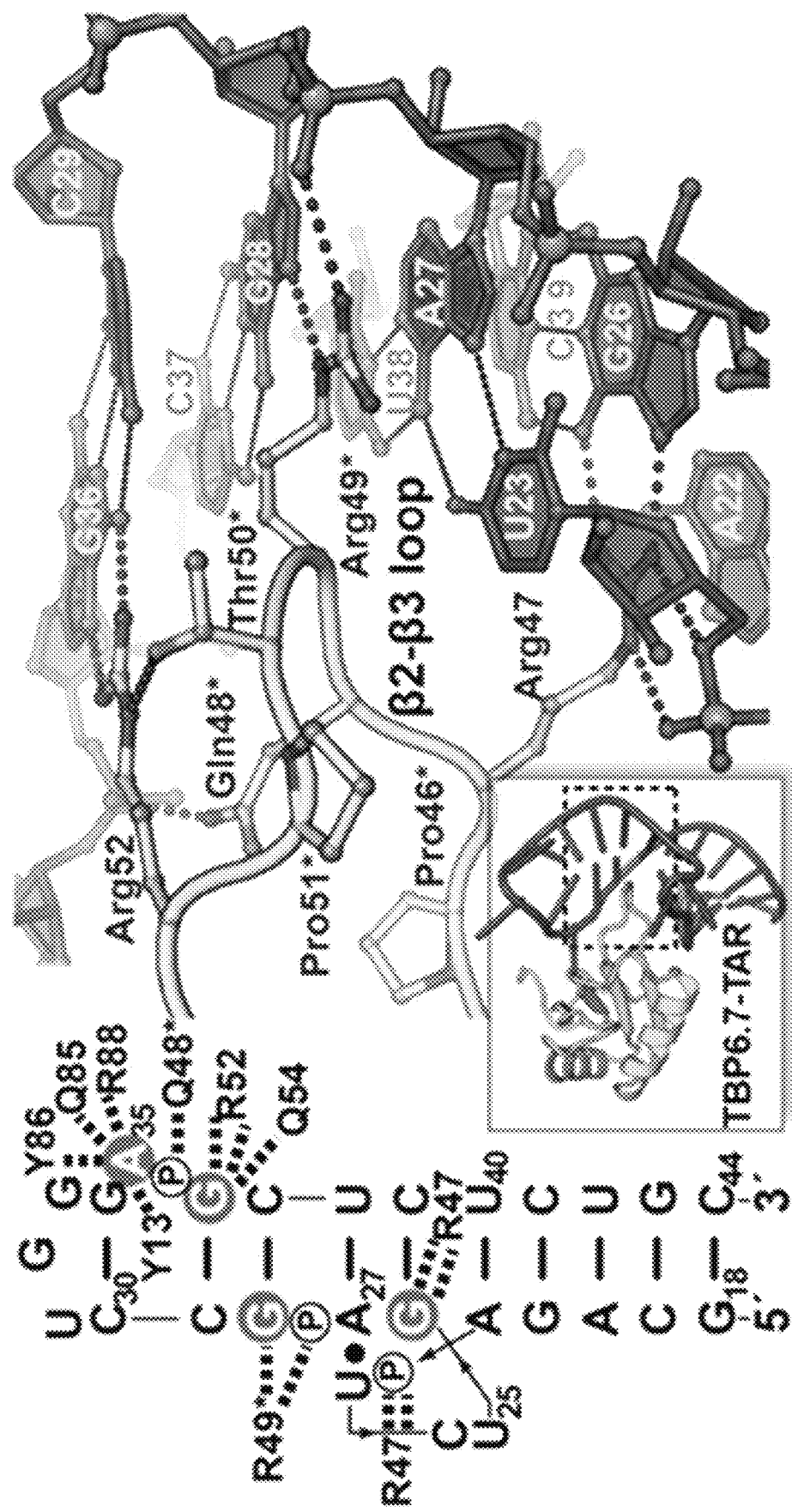
FIG. 1A-B depict β2-β3 loop interactions between TBP6.7 and HIV-1 TAR RNA based on the crystal structure. (A) Schematic of the global protein-RNA interactions as thick dashed lines (black). Asterisks (*) indicate evolved residues. Red nucleotides are directly engaged. (B) β2-β3 loop close-up and global structure (inset) depicting amino acid interactions to the TAR (UCU) bulge and upper stem; thin lines (blue) show hydrogen (H) bonding base pairs.

The present disclosure encompasses the discovery of the critical amino acids in the N-terminus of TBPs that provide specificity for HIV-1 TAR, as well as the discovery of a minimal β-hairpin that retains TAR affinity and inhibits HIV transcription. The peptides, compositions comprising said peptides, and uses thereof are discussed in further detail below.

I. Definitions

The singular forms "a," "an" and "the" include plural referents unless the context clearly dictates otherwise.

As used herein, the term "HIV" refers to a human immunodeficiency virus, and is not limiting in regards to a particular HIV genotype or subtype. Accordingly, the term "HIV" encompasses the two major types, HIV-1 and HIV-2.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature. The treatment regime herein can be either consecutive or intermittent. Subjects for whom the preventive measures are appropriate include those with one or more known risk factors for the disorder (e.g., HIV infection or acquired immune deficiency syndrome (AIDS).

The term "effective amount" refers to an amount of peptide effective to treat a disease or disorder in a mammal. In the case of an HIV infection or AIDS, the effective amount of a peptide may: inhibit (i.e., slow to some extent and preferably stop) viral replication; inhibit (i.e., slow to some extent and preferably stop) HIV infection of uninfected cells; reduce the number of HIV infected cells; and/or relieve to some extent one or more of the symptoms associated with the disorder. For HIV therapy or AIDS therapy, efficacy in vivo can, for example, be measured by a decrease in viral load (i.e., any reduction in plasma HIV ribonucleic acid (RNA) level, though preferably below the level of detection of sensitive HIV-RNA assay), reduced AIDS morbidity, reduced AIDS mortality, an increase in the subject's $CD4^+$ cell count, etc.

As used herein, "individual" or "subject" means a mammal, particularly a non-human primate, e.g., apes and monkeys, and most particularly a human.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "amino acid" within the scope of the present invention is used in its broadest sense. The term includes L-amino acids and D-amino acids, natural protein occurring amino acids and natural non-protein amino acids, as well as chemically-modified amino acids such as amino acid analogs, and chemically-synthesized compounds having properties known in the art to be characteristic of an amino acid. For example, analogs or mimetics of phenylalanine or proline, which allow the same conformational restriction of the peptides compounds as natural Phe or Pro, are included within the definition of amino acid. Such analogs and mimetics are referred to herein as "functional equivalents" of an amino acid. Other examples of amino acids are listed by Roberts and Vellaccio, *The Peptides: Analysis, Synthesis, Biology*, Eds. Gross and Meiehofer, Vol. 5, p. 341 (Academic Press, Inc.: N.Y. 1983). The commonly used one- and three-letter abbreviations for naturally-occurring amino acids are used herein (Lehninger, *Biochemistry,* 2d ed., pp. 71-92, (Worth Publishers: New York, 1975).

Commonly-encountered amino acids that are not encoded by the genetic code include, for example, those described in WO 90/01940, as well as, for example, 2-amino adipic acid (Aad) for Glu and Asp; 2-aminopimelic acid (Apm) for Glu and Asp; 2-aminobutyric (Abu) acid for Met, Leu, and other aliphatic amino acids; 2-aminoheptanoic acid (Ahe) for Met, Leu, and other aliphatic amino acids; 2-aminoisobutyric acid (Aib) for Gly; cyclohexylalanine (Cha) for Val, Leu and Ile; homoarginine (Har) for Arg and Lys; 2,3-diaminopropionic acid (Dpr) for Lys, Arg, and His; N-ethylglycine (EtGly) for Gly, Pro, and Ala; N-ethylglycine (EtGly) for Gly, Pro, and Ala; N-ethylasparagine (EtAsn) for Asn, and Gln; hydroxylysine (Hyl) for Lys; allohydroxylysine (AHyl) for Lys; 3-(and 4-)hydroxyproline (3Hyp, 4Hyp) for Pro, Ser, and Thr; allo-isoleucine (AIle) for Ile, Leu, and Val; Δ-amidinophenylalanine for Ala; N-methylglycine (MeGly, sarcosine) for Gly, Pro, and Ala; N-methylisoleucine (MeIle) for Ile; norvaline (Nva) for Met and other aliphatic amino acids; norleucine (Nle) for Met and other aliphatic amino acids; ornithine (Orn) for Lys, Arg and His; citrulline (Cit) and methionine sulfoxide (MSO) for Thr, Asn, and Gln; and N-methylphenylalanine (MePhe), trimethylphenylalanine, halo-(F-, Cl-, Br-, or I-)phenylalanine, or trifluorylphenylalanine for Phe. Modified or unusual amino acids which can be used to practice the invention also include D-amino acids, a N-Cbz-protected amino acid, 2,4-diaminobutyric acid, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanocarboxylic acid, 1-aminocyclopropanecarboxylic acid, and 2-benzyl-5-aminopentanoic acid.

"Peptides" are defined herein as organic compounds comprising a chain of two or more amino acids covalently joined by peptide bonds. The term "peptide" includes polypeptides. Preferably, peptides of the present disclosure have about 7 to about 70 amino acids, more preferably about 10 to about 30 amino acids, and most preferably about 13 to about 20 amino acids. The definition includes linear peptides, cyclic peptides, and peptide derivatives, as well as their salts and optical isomers.

The term "peptide bond" means a covalent amide linkage formed by loss of a molecule of water between the carboxyl group of one amino acid and the amino group of a second amino acid.

The term "peptide backbone" means the chain of atoms of a peptide comprising the carboxamide groups that are the peptide bonds together with the atoms of the amino acids that link the carboxyl and amino groups of the amino acid (usually the α-carbon of an α-amino acid).

The term "side chain" means groups that are attached to the peptide backbone, and typically refers to the group attached to the α-carbon of an α-amino acid. For example, for the side chains of the proteinogenic amino acids include: methyl (alanine), hydroxymethyl (serine), benzyl (phenylalanine), mercaptomethyl (cysteine), and carboxymethyl (aspartic acid).

The term "derivative" as applied to compounds comprising a peptide chain means a compound wherein one or more of the amino, hydroxyl, or carboxyl groups in a side chain of a peptide, or the terminal amino or carboxyl groups are modified. The term "C-terminal derivative" used in reference to a peptide means a peptide where the C-terminal carboxyl group is modified. The term "N-terminal derivative" used in reference to a peptide means a peptide where the N-terminal amino group is modified. For example, one or more of the amino, hydroxyl, or carboxyl groups in a side chain of the peptide, or the terminal amino or carboxyl groups, may be modified to a derivative functional group. Non-limiting examples of derivative functional groups suitable for amino, hydroxyl, or carboxyl groups in a peptide follow. For example, an amino group may be derivatized as an amide (such as an alkyl carboxamide, acetamide), a carbamate (such as an alkyl carbamate, e.g., methyl carbamate or t-butylcarbamate), or a urea. As another example, a hydroxyl group may be derivatized as an ester (such as an alkanoate, e.g., acetate, propionate, or an arenecarboxylate, e.g., benzoate), a carbamate (such as an alkyl carbamate, e.g. methyl carbamate), a carbonate (such as an alkyl carbonate, e.g., ethyl carbonate). As another example, a carboxyl group may be derivatized as an ester (such as an alkyl ester, e.g., ethyl ester) or an amide (e.g., primary carboxamide, an N-alkyl secondary carboxamide, or an N,N-dialkylcarboxamide). Alternatively, or in addition, one or more of the amino groups in a side chain or a terminal α-amino group of a peptide disclosed herein may be modified by an acetyl group, a formyl group, a methyl group, a myristoyl group, a palmitoyl group, a propionyl group, or ubiquitin. Other modifications are known in the art. The person skilled in the art will appreciate that derivatives of the peptide may improve an aspect of the peptide (e.g., solubility, susceptibility to peptidases, etc.) without substantially affecting the desired activity of the parent peptide (e.g., specific binding to HIV-1 TAR). Preferred embodiments of the invention are those wherein three or fewer of the amino, carboxyl, and hydroxyl groups, and preferably two or fewer, or one or none, are modified. The term "derivative" also includes salts of derivatives.

The term "isolated peptide" means a peptide substantially free of contaminants or cell components with which the peptide naturally occurs, or the reagents used in synthesis or the byproducts of synthesis. "Isolated" and "substantially free of contaminants" does not mean that the preparation is technically pure (homogeneous), but it is sufficiently pure to provide the peptide in a form in which it can be used therapeutically.

The term "cell-penetrating domain" refers to a peptide that is capable of crossing cell membranes and of directing the transport of a peptide, protein, or molecule associated with the cell-penetrating domain, from the outside of a cell into the cytoplasm of the cell through the cytoplasmic membrane of the cell.

The term "conjugated" referring to the linking of two peptides means that the two peptides are covalently linked to one another. The linking may be accomplished directly, through the formation of an amide bond between the carboxyl group of one peptide and an amino group of the other peptide, or by means of a linking group wherein the linking group has covalent bonds to each of the peptides. For example, the linking group may be an amino acid, a peptide, or any group having at least two functional groups and capable of forming covalent bond to each of the two peptide chains. The term "directly bound" or "directly conjugated", referring to the joining of two chemical groups, means that the groups are linked by means of a covalent bond (rather than being linked by virtue of each being bound to a linking group).

A "conjugate," refers to a compound having two portions covalently linked (conjugated) together, where each of the portions is derived from different proteins. The two portions may be linked directly by a single peptide bond or by means of a linking group wherein the linking group has covalent bonds to each of the peptides.

A "fusion protein" refers to a polypeptide having two portions covalently linked (conjugated) together, where each of the portions is derived from different proteins. The two portions may be linked directly by a single peptide bond or through a linker containing one or more amino acid residues. Generally, the two portions and the linker will be in reading frame with each other and are produced using recombinant techniques. A fusion protein is an example of a conjugate.

II. Peptides

The present disclosure provides simple β-hairpin peptides in linear and cyclic form. Peptides of the present disclosure preferably bind HIV-1 Trans-Activation Response element (HIV-1 TAR), and more preferably inhibit the HIV-1 Tat-TAR interaction and/or inhibit Tat-dependent long terminal repeat (LTR) transcription. The polynucleotide sequence of HIV-1 TAR is provided as SEQ ID NO: 25. Peptides of the present disclosure can be conjugated to one or more additional domains to facilitate expression and/or purification, to direct the peptide to the correct intracellular location, and/or to target to a peptide to an infected cell.

In an aspect, the present disclosure provides isolated peptides that specifically bind to HIV-1 TAR, as well as derivatives thereof and conjugates thereof. The term "derivative" is defined above. Conjugates are described in further detail in Section II(a). Isolated peptides of the present disclosure can be linear or cyclic, and may be comprised of L-amino acids, D-amino acids, natural protein occurring amino acids, natural non-protein amino acids, chemically-modified amino acids, functional equivalents of amino acids, modified or unusual amino acids, or any combination thereof. Peptides of the present disclosure, and the derivatives and conjugates thereof, "specifically bind to HIV-1 TAR" when the affinity constant or affinity of interaction (KD) is between about 0.1 pM to about 25 μM, preferably about 0.1 pM to about 20 μM, preferably about 0.1 pM to about 1 µM, more preferably about 0.1 pM to about 100 nM. Methods for determining the affinity constant of a binding interaction are known in the art. Suitable methods are also disclosed in Crawford et al., *ACS Chem Biol*, 2016, 11: 2206-2215, the disclosure of which is hereby incorporated by reference in its entirety.

In some embodiments, an isolated peptide that specifically binds to HIV-1 TAR consists of an amino acid sequence of SEQ ID NO: 2, or is a derivative or conjugate thereof. In other embodiments, an isolated peptide that specifically binds to HIV-1 TAR consists of an amino acid sequence of SEQ ID NO: 3, or is a derivative or conjugate thereof. In each of the above embodiments, the amino acid sequence of the isolated peptide may consist of SEQ ID NO: 4, or may be a derivative or conjugate thereof. Alternatively, the amino acid sequence of the isolated peptide may consist of residues 4 to 16 of an amino acid sequence selected from the group SEQ ID NO: 8 to SEQ ID NO: 24, or may be a derivative or conjugate thereof. In an exemplary embodiment, the amino acid sequence of the isolated peptide consists of residues 4 to 16 of SEQ ID NO: 15, or is a derivative or conjugate thereof.

In other embodiments, an isolated peptide that specifically binds to HIV-1 TAR comprises of an amino acid sequence of SEQ ID NO: 2 and is 13 to 19 amino acids in length, or is a derivative or conjugate thereof. In other embodiments, an isolated peptide that specifically binds to HIV-1 TAR comprises an amino acid sequence of SEQ ID NO: 3 and is 13 to 19 amino acids in length, or is a derivative or conjugate thereof. In each of the above embodiments, the amino acid sequence of the isolated peptide may comprise SEQ ID NO: 4, or may be a derivative or conjugate thereof. Alternatively, the amino acid sequence of the isolated peptide may comprise residues 4 to 16 of an amino acid sequence selected from the group SEQ ID NO: 8 to SEQ ID NO: 24, or may be a derivative or conjugate thereof. In an exemplary embodiment, the amino acid sequence of the isolated peptide comprises residues 4 to 16 of SEQ ID NO: 15, or is a derivative or conjugate thereof.

In other embodiments, an isolated peptide that specifically binds to HIV-1 TAR consists of an amino acid sequence of SEQ ID NO: 5, or is a derivative or conjugate thereof. In still other embodiments, an isolated peptide that specifically binds to HIV-1 TAR consists of an amino acid sequence of SEQ ID NO: 6, or is a derivative or conjugate thereof. In each of the above embodiments, the isolated peptide may consist of an amino acid sequence of SEQ ID NO: 7, or may be a derivative or conjugate thereof. Alternatively, the amino acid sequence of the isolated peptide may consist of an amino acid sequence selected from the group SEQ ID NO: 8 to SEQ ID NO: 24, or may be a derivative or conjugate thereof. In an exemplary embodiment, the isolated peptide consists of an amino acid sequence of SEQ ID NO: 15, or is a derivative or conjugate thereof.

In still further embodiments, an isolated peptide or derivative thereof that specifically binds to HIV-1 TAR is a cyclic peptide. In various embodiments, the amino acid sequence of the cyclic peptide consists of SEQ ID NO: 2 or SEQ ID NO: 3, or is a derivative or conjugate thereof. For example, the amino acid sequence of the cyclic peptide may consist of SEQ ID NO: 4, or may be a derivative or conjugate thereof. Alternatively, the amino acid sequence of the cyclic peptide may consist of residues 4 to 16 of an amino acid sequence selected from the group SEQ ID NO: 8 to SEQ ID NO: 24, or may be a derivative or conjugate thereof. In yet another example, the amino acid sequence of the cyclic peptide may consist of residues 4 to 16 of SEQ ID NO: 15, or may be a derivative or conjugate thereof. In various other embodiments, the amino acid sequence of the cyclic peptide consists of SEQ ID NO: 5 or SEQ ID NO: 6, or is a derivative or conjugate thereof. For example, the amino acid sequence of the cyclic peptide may consist of SEQ ID NO: 7, or may be a derivative or conjugate thereof. Alternatively, the amino acid sequence of the cyclic peptide may consist of an amino acid sequence selected from the group SEQ ID NO: 8 to SEQ ID NO: 2, or may be a derivative or conjugate thereof. In yet another example, the amino acid sequence of the cyclic peptide may consist of SEQ ID NO: 15, or may be a derivative or conjugate thereof.

Still further, in each of the above embodiments a derivative may be an N-terminal derivative, a C-terminal derivative, or an N-terminal derivative and a C-terminal derivative. In an exemplary embodiment, the modification improves resistance of the peptide to degradation by peptidases (e.g., N-terminal acetylation, N-terminal methylation, C-terminal amidation, etc.).

In another aspect, the present disclosure provides cyclic peptides, as well as derivatives thereof and conjugates thereof. The term "derivative" is defined above. Conjugates are described in further detail in Section II (a). Cyclic peptides of the present disclosure may be comprised of L-amino acids, D-amino acids, natural protein occurring amino acids, natural non-protein amino acids, chemically-modified amino acids, functional equivalents of amino acids, modified or unusual amino acids, or any combination thereof.

In some embodiments, a cyclic peptide comprises an amino acid sequence of SEQ ID NO: 2, or is a derivative or conjugate thereof. In other embodiments, a cyclic peptide comprises an amino acid sequence of SEQ ID NO: 3, or is a derivative or conjugate thereof. In each of the above embodiments, the amino acid sequence of the cyclic peptide may comprise SEQ ID NO: 4, or may be a derivative or conjugate thereof. Alternatively, the amino acid sequence of the cyclic peptide may comprise residues 4 to 16 of an amino acid sequence selected from the group SEQ ID NO: 8 to SEQ ID NO: 24, or may be a derivative or conjugate thereof. In an exemplary embodiment, the amino acid sequence of the cyclic peptide comprises residues 4 to 16 of SEQ ID NO: 15, or is a derivative or conjugate thereof.

In other embodiments, a cyclic peptide comprises an amino acid sequence of SEQ ID NO: 5, or is a derivative or conjugate thereof. In other embodiments, a cyclic peptide comprises an amino acid sequence of SEQ ID NO: 6, or is a derivative or conjugate thereof. A cyclic peptide comprising an amino acid sequence of SEQ ID NO: 5 or SEQ ID NO: 6, or derivatives or conjugates thereof, includes N-terminal truncations of one, two, or three amino acids and/or C-terminal truncations of one, two, or three amino acids. In each of the above embodiments, the cyclic peptide may comprise an amino acid sequence of SEQ ID NO: 7, or may be a derivative or conjugate thereof. Alternatively, the amino acid sequence of the cyclic peptide may comprise an amino acid sequence selected from the group SEQ ID NO: 8 to SEQ ID NO: 24, or may be a derivative or conjugate thereof. In an exemplary embodiment, the cyclic peptide comprises an amino acid sequence of SEQ ID NO: 15, or is a derivative or conjugate thereof.

In each of the above embodiments directed to a cyclic peptide, the cyclic peptide may be isolated. Alternatively, or in addition, the cyclic peptide in each of the above embodiments may specifically bind to HIV-1 TAR. Still further, in each of the above embodiments a derivative may be an N-terminal derivative, a C-terminal derivative, or an N-terminal derivative and a C-terminal derivative. In an exemplary embodiment, the modification improves resistance of the peptide to degradation by peptidases (e.g., N-terminal acetylation, N-terminal methylation, C-terminal amidation, etc.).

In embodiments where the peptide of the present disclosure is a cyclic peptide, the peptide can be cyclized by head-to-tail cyclization, side chain-to-tail cyclization, head-to-side chain cyclization, or side chain-to-side chain cyclization. The ring structure can be formed by any suitable chemistry known in the art and available for ring closure. However, closure via simple disulfide bond formation (e.g., disulfide bond formation between the thiol groups of two cysteine amino acids) is not preferred since the interior of a cell is reducing. Non-limiting examples of preferred types of bonds for ring closure include amide, lactone, ether, thioether, thiocarbonyl, etc. Many suitable methods are well-known in the art for preparing cyclized peptides as contemplated herein, and various non-limiting methods are further detailed in Section II (c) and the Examples.

In certain embodiments, a cyclic peptide of the present disclosure is formed by conjugating two side chains occupying the same face of the β-sheet formed by β-hairpin. In an exemplary embodiment, the side chains of amino acids 1 and 13 of SEQ ID NO: 2 or SEQ ID NO: 3, or SEQ ID NO: 4 are conjugated to form a cyclic peptide. In an exemplary embodiment, the side chains of amino acids 2 and 18 of SEQ ID NO: 5 or SEQ ID NO: 6, or SEQ ID NO: 7 are conjugated to form a cyclic peptide. In another exemplary embodiment, the side chains of amino acids 4 and 16 of SEQ ID NO: 5 or SEQ ID NO: 6, or SEQ ID NO: 7 are conjugated to form a cyclic peptide. Amino acids 1 and 13 of SEQ ID NO: 2 or SEQ ID NO: 3, or SEQ ID NO: 4, or amino acids 4 and 16 of any one of SEQ ID NO: 5-24, can be engineered such that side chain-to-side chain cyclization occurs between those positions using methods well-known in the art. As a non-limiting example, cysteine residues may be engineered at (a) amino acids 1 and 13 of SEQ ID NO: 2, SEQ ID NO: 3, or SEQ ID NO:4, (b) at amino acids 2 and 18 of SEQ ID NO: 4, SEQ ID NO: 5, or SEQ ID NO:6, (c) at amino acids 2 and 18 of SEQ ID NO: 4, SEQ ID NO: 5, or SEQ ID NO:6, (d) at amino acids 4 and 16 of SEQ ID NO: 4, SEQ ID NO: 5, or SEQ ID NO:6, (e) at amino acids 4 and 16 of any one of SEQ ID NO: 5-24, or (f) at amino acids 4 and 16 of any one of SEQ ID NO: 5-24, and cyclization can occur via a tandem thiol SNAr reaction with hexafluorobenzene. See, for example, Spokoyny *Journal of the American Chemical Society* 2013, 135: 5946-5949, or WO 2015/181545. Alternatively, Lys/Asp side chain-to-side chain cyclization and Glu/Lys side chain-to-side chain cyclization is routinely performed in the art, as are many other well-known approaches.

The peptides of this disclosure may be in the form of any pharmaceutically acceptable salt. Acid addition salts of the peptides of this invention are prepared in a suitable solvent from the peptide and an excess of an acid, such as hydrochloric, hydrobromic, sulfuric, phosphoric, acetic, trifluoroacetic, maleic, succinic or methanesulfonic. Where the peptides of this invention include an acidic moiety, suitable pharmaceutically acceptable salts may include alkali metal salts, such as sodium or potassium salts, or alkaline earth metal salts, such as calcium or magnesium salts.

(a) Conjugates

As used herein, a conjugate comprises a peptide of the present disclosure conjugated to at least one additional domain. Non-limiting examples of suitable additional domains include signal sequences, cell-penetrating or translocation domains, and marker domains.

In some embodiments, a conjugate can comprise a peptide described above in this section conjugated to a signal sequence. Transport of protein produced by transgenes to a subcellular compartment or for secretion is accomplished by means of operably linking the nucleotide sequence encoding a signal sequence to the 5' and/or 3' region of a gene encoding the protein of interest (i.e., a peptide of the present disclosure, or a derivative thereof). Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion. Any signal sequence known in the art is contemplated by the present invention.

In other embodiments, a conjugate can comprise a peptide described above in this section conjugated to at least one marker domain. Non-limiting examples of marker domains include fluorescent proteins, luciferase enzymes, purification tags, and epitope tags. In some embodiments, the marker domain can be a fluorescent protein. Non limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreenI), yellow fluorescent proteins (e.g., YFP, EYFP, Citrine, Venus, YPet, PhiYFP, ZsYellowI,), blue fluorescent proteins (e.g., EBFP, EBFP2, Azurite, mKalamaI, GFPuv, Sapphire, T-sapphire,), cyan fluorescent proteins (e.g. ECFP, Cerulean, CyPet, AmCyanI, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedI, AsRed2, eqFP61 1, mRasberry, mStrawberry, Jred), and orange fluorescent proteins (e.g., mOrange, mKO, Kusabira-Orange, Monomeric Kusabira-Orange, mTangerine, tdTomato) or any other suitable fluorescent protein. In other embodiments, the marker domain can be a luciferase enzyme. Non-limiting examples include firefly luciferase, *Renilla* luciferase, Nanoluc luciferase, and derivatives thereof. In other embodiments, the marker domain can be a purification tag and/or an epitope tag. Exemplary tags include, but are not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His, biotin carboxyl carrier protein (BCCP), and calmodulin. The marker domain can be located at the N-terminus and/or the C-terminal of a peptide of the present disclosure.

In still other embodiments, a conjugate can comprise a peptide described above in this section conjugated to at least one cell penetrating domain. In one embodiment, the cell-penetrating domain can be a cell-penetrating peptide sequence derived from the HIV-1 TAT protein. In another embodiment, the cell-penetrating domain can be TLM, a cell-penetrating peptide sequence derived from the human hepatitis B virus. In still another embodiment, the cell-penetrating domain can be MPG. In an additional embodiment, the cell-penetrating domain can be Pep-1, VP22, a cell penetrating peptide from Herpes simplex virus, or a polyarginine peptide sequence. The cell-penetrating domain can be located at the N-terminus and/or the C-terminal of a peptide of the present disclosure.

A peptide of the present disclosure can be conjugated to the at least one additional domain directly or indirectly. In some embodiments, a conjugate comprises a linking group. A linking group may be any moiety that is at least bifunctional provided that the resulting link between the peptide and the additional domain is stable. Suitable linking moieties include bi- and multi-functional alkyl, aryl, aralkyl or peptidic moieties, alkyl, aryl, or aralkyl aldehydes acids esters and anhydrides, sulfhydryl or carboxyl groups, such as maleimido benzoic acid derivatives, maleimido propionic acid derivatives and succinimido derivatives or may be derived from cyanuric bromide or chloride, carbonyldiimidazole, succinimidyl esters or sulphonic halides and the like (Fischer et al., U.S. Pat. No. 6,472,507, the entire disclosure of which is incorporated herein by reference). The functional groups on the linker moiety may include amino, hydrazino, hydroxyl, thiol, maleimido, carbonyl, and carboxyl groups. Optionally the linker group is selected so as to be sufficiently labile (e.g., to enzymatic cleavage by an enzyme present in the targeted tissue) so that it is cleaved following transport of the peptide, thereby releasing the peptide. Exemplary labile linkages are described in Low et al., U.S. Pat. No. 5,108,921, the entire disclosure of which is incorporated herein by reference. The conjugate may also dissociate by way of chemical cleavage between the peptide of the present disclosure and the additional domain. Within the embodiments wherein the linker moiety includes amino acid residues, such cleavage may occur within the linker moiety itself. In some embodiments, a conjugate is a fusion protein. In other embodiments, a conjugate comprises a non-peptide linking group.

(b) Pharmaceutical Compositions

An active compound of the present disclosure (i.e., any peptide of the present disclosure, including derivatives and conjugates thereof, that specifically binds to HIV-1 TAR) can be incorporated into compositions, which in some embodiments are suitable for pharmaceutical use. Such compositions typically comprise a peptide of this disclosure (including derivatives and conjugates thereof) and an acceptable carrier, for example one that is pharmaceutically acceptable. A "pharmaceutically acceptable carrier" includes any and all solvents, dispersion media, coatings, antibacterial and antifungal agents, isotonic and absorption delaying agents, and the like, compatible with pharmaceutical administration (Gennaro, Remington: The science and practice of pharmacy. Lippincott, Williams & Wilkins, Philadelphia, Pa. (2000)). Examples of such carriers or diluents include, but are not limited to, water, saline, Finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

A pharmaceutical composition is formulated to be compatible with its intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents; for example, parabens, chlorobutanol, phenol, ascorbic acid, and thimerosal, can contain microorganism contamination. Isotonic agents; for example, sugars, polyalcohols such as manitol, sorbitol, and sodium chloride can be included in the composition. Compositions that can delay absorption include agents such as aluminum monostearate and gelatin.

Sterile injectable solutions can be prepared by incorporating the active compound in the required amount in an appropriate solvent with one or a combination of ingredients as required, followed by sterilization. Generally, dispersions are prepared by incorporating the active compound into a sterile vehicle that contains a basic dispersion medium, and the other required ingredients. Sterile powders for the preparation of sterile injectable solutions, methods of preparation include vacuum drying and freeze-drying that yield a powder containing the active ingredient and any desired ingredient from a sterile solutions.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for administration as an aqueous or oily suspension, solution, emulsion, syrup or elixir. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring. Liquid preparations may contain additives including, but not limited to, suspending agents, emulsifying agents, nonaqueous vehicles and preservatives.

For administration by inhalation, the compounds are delivered as an aerosol spray from a nebulizer or a pressurized container that contains a suitable propellant, e.g., a gas such as carbon dioxide.

Systemic administration can also be transmucosal or transdermal. For transmucosal or transdermal administration, penetrants that can permeate the target barrier(s) are selected. Transmucosal penetrants include detergents, bile salts, and fusidic acid derivatives. Nasal sprays or suppositories can be used for transmucosal administration. For transdermal administration, the active compounds are formulated into ointments, salves, gels, or creams.

The compounds can also be prepared in the form of suppositories (e.g., with bases such as cocoa butter and other glycerides) or retention enemas for rectal delivery.

The active compounds can also be are prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art. Liposomal suspensions can also be used as pharmaceutically acceptable carriers. These can be prepared according to methods known to those skilled in the art, such as in (Eppstein et al., U.S. Pat. No. 4,522,811, 1985).

Oral formulations or parenteral compositions in unit dosage form can be created to facilitate administration and dosage uniformity. Unit dosage form refers to physically discrete units suited as single dosages for the subject to be treated, containing a therapeutically effective quantity of active compound in association with the required pharmaceutical carrier. The specification for the unit dosage forms are dictated by, and directly dependent on, the unique characteristics of the active compound and the particular desired therapeutic effect, and the inherent limitations of compounding the active compound.

Nucleic acid molecules encoding peptides of the invention can be inserted into vectors and used as gene therapy vectors. Gene therapy vectors can be delivered to a subject by, for example, intravenous injection, local administration (Nabel and Nabel, U.S. Pat. No. 5,328,470, 1994), or by stereotactic injection (Chen et al., *Proc Natl Acad Sci USA.* 91; 3054-7 (1994)). The pharmaceutical preparation of a gene therapy vector can include an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

(c) Production of Peptides

Peptides of this disclosure can be made by chemical synthesis or by employing recombinant technology. These methods are well-known in the art. Chemical synthesis, especially solid-phase synthesis, is preferred for short (e.g., less than 50 residues) peptides or those containing unnatural or unusual amino acids. Recombinant procedures are preferred for longer peptides. When recombinant procedures are selected, a synthetic gene may be constructed de novo or a natural gene may be mutated by, for example, cassette mutagenesis.

Recombinant DNA techniques for producing peptides of the present disclosure contemplate, in simplified form, taking the gene, either natural or synthetic, encoding the peptide; inserting it into an appropriate vector; inserting the vector into an appropriate host cell; culturing the host cell to cause expression of the gene; and recovering or isolating the peptide produced thereby. Preferably, the isolated peptide is then purified to a suitable degree.

The DNA sequence encoding a peptide of the present disclosure can be cloned and manipulated (including but not limited to codon optimized) so that it may be expressed in a convenient host. DNA encoding a peptide of the present disclosure can be obtained by any method known in the art. See, for example, Sambrook et al., *Molecular Cloning: A Laboratory Manual* (2d ed.) (Cold Spring Harbor Laboratory: N.Y., 1989)). The DNA is then inserted into an appropriate plasmid or vector that is used to transform a host cell. In general, plasmid vectors containing replication and control sequences derived from species compatible with the host cell are used in connection with those hosts. The vector ordinarily carries a replication site, as well as sequences encoding proteins or peptides that are capable of providing phenotypic selection in transformed cells. Preferred vectors can be constructed using standard techniques by combining the relevant traits of the desired vector. Relevant traits include but are not limited to a promoter, a ribosome binding site, polynucleotide sequence(s) encoding antibiotic resistance marker(s), appropriate origins of replication, and polynucleotide sequences encoding additional domains (including but not limited to signal sequences, targeting domains, cell-penetrating or translocation domains, and marker domains).

The host cell may be prokaryotic or eukaryotic. When expressed by prokaryotes the peptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting. In addition to prokaryotes, eukaryotic organisms, such as yeast or fungi, or cells derived from multicellular organisms (insects, plants, mammals, etc.) may be used. In principle, any such cell culture is workable. However, interest has been greatest in vertebrate cells, and propagation of vertebrate cells in culture (tissue culture) has become a reproducible procedure. *Tissue Culture*, Academic Press, Kruse and Patterson, editors (1973). Examples of such useful host cell lines are VERO and HeLa cells, Chinese Hamster Ovary (CHO) cell lines, W138, 293, BHK, COS-7 and MDCK cell lines.

A variation on the above procedures contemplates the use of gene fusions, wherein the gene encoding the desired peptide is associated, in the vector, with a gene encoding another protein or a fragment of another protein. This results in the desired peptide being produced by the host cell as a fusion with another protein or peptide. The "other" protein or peptide can be a protein or peptide that can be secreted by the cell, making it possible to isolate and purify the desired peptide from the culture medium. Alternatively, the fusion protein can be expressed intracellularly. It is useful to use fusion proteins that are highly expressed. The use of gene fusions, though not essential, can facilitate the expression of heterologous peptides as well as the subsequent purification of those gene products. Harris, in *Genetic Engineering*, Williamson, R., Ed. (Academic Press, London, Vol. 4, 1983), p. 127; Ljungquist et al., *Eur. J. Biochem.*, 186: 557-561 (1989) and Ljungquist et al., *Eur. J. Biochem.*, 186: 563-569 (1989). See Nilsson et al., *Protein Engineering*, 1: 107-113 (1987). Marston, *Biochem J.* 240: 1 (1986).

After expression and secretion, the fusion protein may be cleaved to yield free peptide, which can be purified from the reaction mix. The cleavage may be accomplished using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide. Alternatively, one can employ proteolytic cleavage of fusion protein (Carter, in *Protein Purification: From Molecular Mechanisms to Large-Scale Processes*, Ladisch et al., eds. (American Chemical Society Symposium Series No. 427, 1990), Ch 13, pages 181-193; Varadarajan et al., *Proc. Natl. Acad. Sci. USA*, 82: 5681-5684 (1985); Castellanos-Serra et al., *FEBS Letters*, 378: 171-176 (1996); Nilsson et al., *J. Biotechnol.*, 48: 241-250 (1996)). Proteases such as Factor Xa, thrombin, subtilisin, or trypsin, or its mutants, and a number of others have been successfully used to cleave fusion proteins. *Methods in Mol. Biol.*, 32: 289-196 (1994). Typically, a peptide linker that is amenable to cleavage by the protease used is inserted between the "other" protein and the desired peptide. Using recombinant DNA methodology, the nucleotide base pairs encoding the linker are inserted between the genes or gene fragments coding for the other proteins. Proteolytic cleavage of the partially-purified fusion protein containing the correct linker can then be carried out on either the native fusion protein, or the reduced or denatured fusion protein.

As well as by recombinant methods, peptides of the present disclosure can be conveniently prepared by solid-phase synthesis and purified according to methods known in the art. Any of a number of well-known procedures utilizing a variety of resins and reagents may be used to prepare the peptides of this disclosure. See, for example, Merrifield, *J. Am. Chem. Soc.*, 85: 2149 (1964); Houghten, *Proc. Natl. Acad. Sci. USA*, 82: 5132 (1985)), although other equivalent chemical syntheses known in the art are employable. Solid-phase synthesis is typically initiated from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London), 38: 1597-1598 (1966). Chloromethylated resins are commercially available from BioRad Laboratories, Richmond, Calif. and from Lab. Systems, Inc. The preparation of such a resin is described by Stewart et al., *Solid Phase Peptide Synthesis* (Freeman & Co., San Francisco 1969), Chapter 1, pp. 1-6. BHA and MBHA resin supports are commercially available and are generally used only when the desired polypeptide being synthesized has an unsubstituted amide at the C-terminus.

The amino acids are coupled to the peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethylchloroformate, phenyl chloroformate, sec-butyl chloroformate, isobutyl chloroformate, pivaloyl chloride or like acid chlorides. Alternatively, the amino acid can be converted to an active ester such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole Another coupling method involves use of a suitable coupling agent such as N,N'-dicyclohexylcarbodiimide or N,N'-diisopropyl-carbodiimide. Other appropriate coupling agents, apparent to those skilled in the art, are disclosed in E. Gross & J. Meienhofer, *The Peptides: Analysis Structure, Biology*, Vol. 1: Major Methods of Peptide Bond Formation (Academic Press: New York, 1979).

It should be recognized that the α-amino group of each amino acid employed in the peptide synthesis must be protected during the coupling reaction to prevent side reactions involving their active α-amino function. It should also be recognized that certain amino acids contain reactive side-chain functional groups (e.g., sulfhydryl, amino, carboxyl, and hydroxyl) and that such functional groups must also be protected with suitable protecting groups to prevent a chemical reaction from occurring at that site during both the initial and subsequent coupling steps. Suitable protecting groups, known in the art, are described in Gross and Meienhofer, *The Peptides: Analysis. Structure, Biology*, Vol. 3: "Protection of Functional Groups in Peptide Synthesis" (Academic Press: New York, 1981).

In the selection of a particular side-chain protecting group to be used in synthesizing the peptides, the following general rules are followed. An α-amino protecting group (a) must render the α-amino function inert under the conditions employed in the coupling reaction, (b) must be readily removable after the coupling reaction under conditions that will not remove side-chain protecting groups and will not alter the structure of the peptide fragment, and (c) must eliminate the possibility of racemization upon activation immediately prior to coupling. A side-chain protecting group (a) must render the side-chain functional group inert under the conditions employed in the coupling reaction, (b) must be stable under the conditions employed in removing the α-amino protecting group, and (c) must be readily removable upon completion of the desired amino acid peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups such as triphenylmethyl and 2-(p-biphenylyl)isopropyloxycarbonyl are very labile and can be cleaved under mild acid conditions. Other protecting groups, such as t-butyloxycarbonyl (BOC), t-amyloxycarbonyl adamantyl-oxycarbonyl, and p-methoxybenzyloxycarbonyl, are less labile and require moderately strong acids, such as trifluoroacetic, hydrochloric, or boron trifluoride in acetic acid, for their removal. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal. Among the classes of useful amino acid protecting groups are included: (1) for an α-amino group, (a) aromatic urethane-type protecting groups, such as fluorenylmethyloxycarbonyl (FMOC) CBZ, and substituted CBZ, such as, e.g., p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenylyl)-isopropyloxycarbonyl, allyloxycarbonyl and the like; (c) cycloalkyl urethane-type protecting groups, such as cyclopentyloxycarbonyl, adamantyloxycarbonyl, and cyclohexyloxycarbonyl; and d) allyloxycarbonyl. The preferred α-amino protecting groups are BOC or FMOC; (2) for the side chain amino group present in Lys, protection may be by any of the groups mentioned above in (1) such as BOC, p-chlorobenzyloxycarbonyl, etc.; (3) for the guanidino group of Arg, protection may be by nitro, tosyl, CBZ, adamantyloxycarbonyl, 2,2,5,7,8-pentamethylchroman-6-sulfonyl, 2,3,6-trimethyl-4-methoxyphenylsulfonyl, or BOC; (4) for the hydroxyl group of Ser, Thr, or Tyr, protection may be, for example, by C1-C4 alkyl, such as t-butyl; benzyl (BZL); or substituted BZL, such as p-methoxybenzyl, p-nitrobenzyl, p-chlorobenzyl, o-chlorobenzyl, and 2,6-dichlorobenzyl; (5) for the carboxyl group of Asp or Glu, protection may be, for example, by esterification using groups such as BZL, t-butyl, cyclohexyl, cyclopentyl, and the like; (6) for the imidazole nitrogen of His, the tosyl moiety is suitably employed; (7) for the phenolic hydroxyl group of Tyr, a protecting group such as tetrahydropyranyl, tert-butyl, trityl, BZL, chlorobenzyl, 4-bromobenzyl, or 2,6-dichlorobenzyl is suitably employed. The preferred protecting group is 2,6-dichlorobenzyl; (8) for the side-chain amino group of Asn or Gln, xanthyl (Xan) is preferably employed; (9) for Met, the amino acid is preferably left unprotected; (10) for the thio group of Cys, p-methoxybenzyl is typically employed; The C-terminal amino acid, e.g., Lys, is protected at the N-amino position by an appropriately-selected protecting group, in the case of Lys, BOC. The BOC-Lys-OH can be first coupled to the benzhydrylamine or chloromethylated resin according to the procedure set forth in Horiki et al., *Chemistry Letters*, 165-168 (1978) or using isopropylcarbodiimide at about 25EC for 2 hours with stirring. Following the coupling of the BOC-protected amino acid to the resin support, the α-amino protecting group is removed, as by using trifluoroacetic acid (TFA) in methylene chloride or TFA alone. The deprotection is carried out at a temperature between about OEC and room temperature. Other standard cleaving reagents, such as HCl in dioxane, and conditions for removal of specific α-amino protecting groups are described in the literature.

After removal of the α-amino protecting group, the remaining α-amino and side-chain protected amino acids are coupled stepwise within the desired order. As an alternative to adding each amino acid separately in the synthesis, some may be coupled to one another prior to addition to the solid-phase synthesizer. The selection of an appropriate coupling reagent is within the skill of the art. Particularly suitable as a coupling reagent is N,N'-dicyclohexyl carbodiimide or diisopropylcarbodiimide.

Each protected amino acid or amino acid sequence is introduced into the solid-phase reactor in excess, and the coupling is suitably carried out in a medium of dimethylformamide (DMF) or $CH_2Cl_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. A preferred method of monitoring the synthesis is by the ninhydrin reaction, as described by Kaiser et al., *Anal. Biochem*, 34: 595 (1970). The coupling reactions can be performed automatically using well-known methods, for example, a BIOSEARCH 9500™ peptide synthesizer.

Upon completion of the desired peptide sequence, the protected peptide must be cleaved from the resin support, and all protecting groups must be removed. The cleavage reaction and removal of the protecting groups is suitably accomplished simultaneously or stepwise. When the resin support is a chloromethylated polystyrene resin, the bond anchoring the peptide to the resin is an ester linkage formed between the free carboxyl group of the C-terminal residue and one of the many chloromethyl groups present on the resin matrix. It will be appreciated that the anchoring bond can be cleaved by reagents that are known to be capable of breaking an ester linkage and of penetrating the resin matrix.

One especially convenient method is by treatment with liquid anhydrous hydrogen fluoride. This reagent not only will cleave the peptide from the resin but also will remove all protecting groups. Hence, use of this reagent will directly afford the fully deprotected peptide. When the chloromethylated resin is used, hydrogen fluoride treatment results in the formation of the free peptide acids. When the benzhydrylamine resin is used, hydrogen fluoride treatment results directly in the free peptide amines. Reaction with hydrogen fluoride in the presence of anisole and dimethylsulfide at 0° C. for one hour will simultaneously remove the side-chain protecting groups and release the peptide from the resin.

When it is desired to cleave the peptide without removing protecting groups, the protected peptide-resin can undergo methanolysis to yield the protected peptide in which the C-terminal carboxyl group is methylated. The methyl ester is then hydrolyzed under mild alkaline conditions to give the free C-terminal carboxyl group. The protecting groups on the peptide chain then are removed by treatment with a strong acid, such as liquid hydrogen fluoride. A particularly useful technique for methanolysis is that of Moore et al., *Peptides, Proc. Fifth Amer. Pept. Symp*., M. Goodman and J. Meienhofer, Eds., (John Wiley, N.Y., 1977), p. 518-521, in which the protected peptide-resin is treated with methanol and potassium cyanide in the presence of crown ether.

Another method for cleaving the protected peptide from the resin when the chloromethylated resin is employed is by ammonolysis or by treatment with hydrazine. If desired, the resulting C-terminal amide or hydrazide can be hydrolyzed to the free C-terminal carboxyl moiety, and the protecting groups can be removed conventionally.

It will also be recognized that the protecting group present on the N-terminal α-amino group may be removed preferentially either before or after the protected peptide is cleaved from the support.

Purification of the polypeptides of the invention is typically achieved using conventional procedures such as preparative high-pressure liquid chromatography (HPLC) (including reversed-phase HPLC) or other known chromatographic techniques, including but not limited to gel permeation, ion exchange, partition chromatography, affinity chromatography (including monoclonal antibody columns), or countercurrent distribution.

Many suitable methods per se are known for preparing cyclized peptides as contemplated herein. Lys/Asp cyclization has been accomplished using Nα-Boc-amino acids on solid-phase support with Fmoc/9-fluorenylmethyl (OFm) side-chain protection for Lys/Asp; the process is completed by piperidine treatment followed by cyclization. Glu and Lys side-chains also have been crosslinked in preparing cyclic peptides: the peptide is synthesized by solid-phase chemistry on a p-methylbenzhydrylamine resin. The peptide is cleaved from the resin and deprotected. The cyclic peptide is formed using diphenylphosphorylazide in diluted methylformamide. For an alternative procedure, see Schiller et al., *Peptide Protein Res*., 25: 171-177 (1985). See also U.S. Pat. No. 4,547,489. Also useful are thiomethylene bridges. Lebl and Hruby, *Tetrahedron Letters*, 25: 2067-2068 (1984). See also Cody et al., *J. Med. Chem*., 28: 583 (1985). Cyclic peptides may be purified by gel filtration followed by reversed-phase HPLC or other conventional procedures. The peptides can be sterile filtered and formulated into conventional pharmacologically acceptable vehicles.

The starting materials required for the processes described herein are known in the literature or can be prepared using known methods and known starting materials.

If in the peptides being created carbon atoms bonded to four non-identical substituents are asymmetric, then the compounds may exist as diastereoisomers, enantiomers, or mixtures thereof. The syntheses described above may employ racemates, enantiomers, or diastereomers as starting materials or intermediates. Diastereomeric products resulting from such syntheses may be separated by chromatographic or crystallization methods. Likewise, enantiomeric product mixtures may be separated using the same techniques or by other methods known in the art. Each of the asymmetric carbon atoms, when present, may be in one of two configurations (R or S), and both are within the scope of the present invention.

The peptides described in this invention may be isolated as the free acid or base or converted to salts of various inorganic and organic acids and bases. Such salts are within the scope of this invention. Examples of such salts include ammonium, metal salts like sodium, potassium, calcium, and magnesium; salts with organic bases like dicyclohexylamine, N-methyl-D-glucamine and the like; and salts with amino acids like arginine or lysine. Salts with inorganic and organic acids may be likewise prepared, for example, using hydrochloric, hydrobromic, sulfuric, phosphoric, trifluoroacetic, methanesulfonic, malic, maleic, fumaric acid, and the like. Non-toxic and physiologically-compatible salts are particularly useful, although other less desirable salts may have use in the processes of isolation and purification.

A number of methods are useful for the preparation of the salts described above and are known to those skilled in the art. Examples include reaction of the free acid or free base form of the peptide with one or more molar equivalents of the desired acid or base in a solvent or solvent mixture in which the salt is insoluble; or in a solvent like water after which the solvent is removed by evaporation, distillation or freeze drying. Alternatively, the free acid or base form of the product may be passed over an ion-exchange resin to form the desired salt or one salt form of the product may be converted to another using the same general process.

(d) Vectors

In another aspect, the present disclosure provides a nucleic acid sequence encoding a peptide of Section II(d), which can be readily determined by one of skill in the art. In another aspect, the present disclosure provides a vector comprising a nucleic acid sequence encoding a peptide of Section II(d). Suitable vectors include plasmid vectors, phagemids, cosmids, artificial/mini-chromosomes, transposons, and viral vectors. The choice of the vector will vary depending upon the intended use (e.g., stable transformation in bacterial cells, stable transformation in a mammalian cell, etc.). In one embodiment, a nucleic acid sequence encoding a peptide of Section II(d) is present in a plasmid vector. Non-limiting examples of suitable plasmid vectors include pUC, pBR322, pET, pBluescript, pCAMBIA2300, pRI 101, pBI121, pPZP100, and variants thereof. In another embodiment, a nucleic acid sequence encoding a peptide of Section II(d) is present in a viral vector. Suitable viral vectors include, but are not limited to, lentiviral vectors and adeno-associated viral vectors. A vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., $3^{rd}$ edition, 2001.

(e) Functional Activity

In addition to specifically binding to HIV-1 TAR, preferred linear and cyclic peptides of the present disclosure inhibit Tat-TAR interaction, inhibit TAR dependent transcription, inhibit LTR-dependent gene expression, inhibits TAR processing by DICER, increases host cell apoptosis upon viral infection, and/or reduces viral transmission. Inhibition can be complete or partial (e.g., a reduction of about 10%, about 20%, about 30%, about 40%, about 50%, about 60%, about 70%, about 80%, about 90%, or more). Methods for determining the above are known in the art. Illustrative methods are also detailed in the Examples.

III. Methods of Use

In an aspect, peptides of the present disclosure, including derivatives and conjugates thereof, that specifically bind to HIV-1 TAR can be used to inhibit the interaction between HIV Tat and HIV TAR. In one embodiment, a method for inhibiting an interaction between HIV Tat and HIV TAR comprises admixing a peptide of Section II or a derivative or conjugate thereof, an HIV Tat protein, and HIV TAR. The ability to suppress or inhibit the interaction between Tat peptide and TAR can be evaluated using methods known in the art, such as by using ITC as previously shown. See, for example, Crawford et al., *ACS Chem Biol*, 2016, 11: 2206-2215. In another embodiment, a method for inhibiting an interaction between HIV Tat and HIV TAR comprises contacting an HIV infected cell with a peptide of Section II, or a derivative or conjugate thereof. In preferred embodiments, the virus is HIV-1.

In another aspect, peptides of the present disclosure, including derivatives and conjugates thereof, that specifically bind to HIV-1 TAR can be used to inhibit HIV proliferation (e.g., replication). Generally speaking, the method comprises contacting an HIV infected cell with a peptide of Section II, or a derivative or conjugate thereof. In preferred embodiments, the virus is HIV-1.

Methods for evaluating the effect of a compound on the HIV replication in cultured cells are well known in the art. For example, hematopoietic cells (e.g., MT-2 T-cell lymphoma cells, primary peripheral blood mononuclear cells (PBMCs), isolated macrophages, isolated CD4-positive T cells or cultured H9. human T cells) may be acutely infected with HIV using titers known in the art to acutely infect cells in vitro, such as $10^{4.5}TCID_{50}$/mL for HIV-1. The cells are then cultured in the presence of varying amounts of a test compound. Cultures are then assayed for HIV production (e.g. by measuring levels of reverse transcriptase using a reverse transcriptase assay, or p24 antigen using a commercially available ELISA assay). Reduction in viral levels over levels observed in untreated controls indicates the test compound is effective in vitro for treatment of HIV infection. Also, see, for example, Crawford et al., *ACS Chem Biol*, 2016, 11: 2206-2215. A measure of HIV replication in vivo includes, but is not limited to, viral load.

In another aspect, peptides of the present disclosure, including derivatives and conjugates thereof, that specifically bind to HIV-1 TAR can be used for the treatment of diseases and conditions involving an HIV infection. The process comprises administering an effective amount of an active compound of the present disclosure (i.e., any peptide of the present disclosure, including derivatives and conjugates thereof, that specifically binds to HIV-1 TAR), or a pharmaceutical composition comprising an active compound, to an individual in need of such treatment. An individual who is in need of such treatment is an individual who is infected with HIV or an individual who is at risk of infection due to actual or suspected exposure to the virus. In certain embodiments, the individual is diagnosed with AIDS. In preferred embodiments, the virus is HIV-1.

The presence of HIV-1 can be readily detected by any means standard in the art, e.g., by obtaining a patient blood sample and assaying it in vitro for the presence of HIV-1. Prophylaxis is indicated in previously uninfected individuals after known or suspected acute exposure to HIV. Examples of such prophylactic use of an active compound may include, but is not limited to, prevention of virus transmission from mother to infant and other settings where the likelihood of HIV transmission exists, such as, for example, accidents in health care settings wherein workers are exposed to HIV-containing blood products.

The amount of the active compound that will be effective in the treatment of a particular disorder or condition will depend on the nature of the disorder or condition, is and is determined by standard clinical techniques. In addition, in vitro assays may optionally be employed to help identify optimal dosage ranges. The precise dose to be employed in the formulation also will depend on the route of administration and the seriousness of the disease, disorder, or condition and is decided according to the judgment of the practitioner and each patient's circumstances.

In some embodiments, an effective amount of an active compound inhibits (i.e., slow to some extent and preferably stop) viral replication. In other embodiments, an effective amount of an active compound, inhibits (i.e., slow to some extent and preferably stop) HIV infection of uninfected cells. In some embodiments, an effective amount of an active compound reduces the number of HIV infected cells. In some embodiments, an effective amount of an active compound relieves to some extent one or more of the symptoms associated with the disorder. In some embodiments, an effective amount of an active compound reduces AIDS morbidity. In some embodiments, an effective amount of an active compound reduces AIDS mortality.

Also provided are methods of treatment or prophylaxis of HIV infection and/or AIDS by the administration of a combination of drugs. The method comprises administering an effective amount of the compound, or a pharmaceutical composition comprising the compound, as described herein, in combination with one or more compounds selected from the group consisting of reverse transcriptase inhibitors, HIV-1 protease inhibitors, or fusion inhibitors (collectively referred to below as "conventional HIV drug") to an individual in need of such treatment or prophylaxis.

For marketed conventional HIV-1 drugs, suitable doses and dosing protocols are recommended by the manufacturer and published, for example in the *Physician's Desk Reference*, 60th Edition (Thomson Healthcare, 2006), the entire disclosure of which is incorporated herein by, reference. For both marketed drugs and investigational HIV-1 drugs, suitable doses are recommended and published in the literature, in reports of clinical trials of the compounds. The person skilled in the art will refer to such sources in determining a suitable dosed dosing protocol for any particular indication. However, a possible advantage of the using the HIV-1 drug in combination with the compounds of the present disclosure is that it may be possible to use either or both of the compounds at a lower dose than would be possible if the compounds were used separately.

In each of the above embodiments, treatment can result in a decrease in viral load, an increase in the subject's CD4+ cell count, a reduction in AIDS morbidity, a reduction in AIDS mortality, inhibition of HIV infection of uninfected cells, a reduction in the number of HIV infected cells, a decrease to some extent one or more of the symptoms associated with an HIV infection, and/or prevention of HIV transmission.

IV. Administration

An active compound of the present disclosure (i.e., any peptide of the present disclosure, including derivatives and conjugates thereof) may be administered by any route, including oral, rectal, pulmonary, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration. Typically it is contemplated that treatment would be given at least once per day, typically once, twice, three times or four times per day with the doses given at equal intervals throughout the day and night in order to maintain a constant presence of the drug in order to suppress the virus and reduce the opportunity for development of resistance.

One or more active compounds of the present disclosure may be administered simultaneously, by the same or different routes, or at different times during treatment. The peptides of the invention may also be prescribed to be taken in combination with conventional HIV drugs. When used in such combinations, active compound of the present disclosure and conventional HIV drugs may be administered simultaneously, by the same or different routes, or at different times during treatment. The dose of the conventional HIV drug selected will depend on the particular compound being used and the route and frequency of administration. Typically, treatment of the conventional HIV drug will also be given at least once per day, typically once, twice, three times or four times per day with the doses given at equal intervals throughout the day and night, although not necessarily according to the same schedule as the compound of the invention.

The treatment may be carried out for as long a period as necessary. Typically it is contemplated that treatment would be continued indefinitely while the infection persists, although discontinuation might be indicated if the compounds no longer produce a beneficial effect, for example due to development of resistance by the viruses. The treating physician will know how to increase, decrease, or interrupt treatment based on patient response.

The specific dose of an active compound according to the invention to obtain therapeutic benefit for treatment of an HIV infection will, of course, be determined by the particular circumstances of the individual patient including the size, weight, age and sex of the patient, the nature and stage of the disease, the aggressiveness of the disease, and the route of administration of the compound.

For example, a daily dosage from about 0.02 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. Suitable dosage ranges for intravenous administration are generally about 20-500 micrograms of active compound per kilogram body weight.

Suitable dosage ranges for intranasal or inhaled administration are generally about 0.01 pg/kg body weight to 1 mg/kg body weight. In the case of dry powder inhalers and aerosols, the dosage unit is determined by means of a valve which delivers a metered amount. Units in accordance with the invention are typically arranged to administer a metered dose or "puff" which delivers an appropriate dose. The daily dose which may be administered in a single dose or as divided doses throughout the day.

Suppositories generally contain active ingredient in the range of 0.5% to 10% by weight; oral formulations preferably contain 10% to 95% active ingredient.

Effective doses may be extrapolated from dose-response curves derived from in vitro or animal model test systems.

The present disclosure also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that changes may be made in the specific embodiments that are disclosed and still obtain a like or similar result without departing from the spirit and scope of the invention. Therefore, all matter set forth or shown in the accompanying drawings is to be interpreted as illustrative and not in a limiting sense.

EXAMPLES

The following examples illustrate various iterations of the invention.

Example 1

Figure 3A:
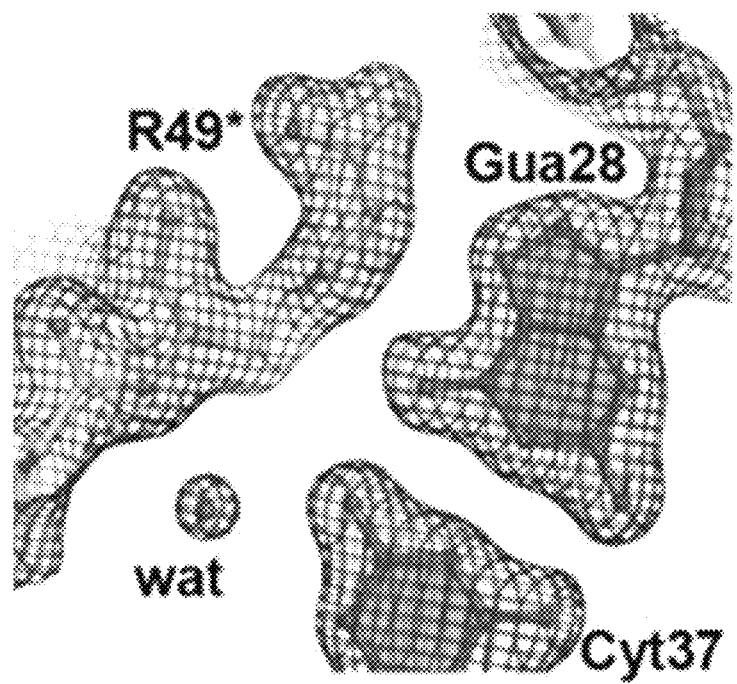
FIG. 3A-C depict TBP6.7-TAR electron density and comparison of RNA binding. (A) $2mF_o\text{-}DF_c$ electron density at 1.0 σ for the refined TBP6.7-TAR complex at 1.8 Å resolution. (B) U1A depicting single-stranded RNA recognition by RNP2 (red) and RNP1 (orange) amino acids that are conserved among RRMs. (C) TBP recognizes the upper duplex stem of TAR and does not make full use of RNP amino acids. RNA termini were truncated for clarity.

The TBP6.7-TAR Crystal Structure Reveals Novel RNA Recognition by a Privileged β-Hairpin Scaffold that Reads the TAR Major-Groove TAR binding protein 6.7 (TBP6.7) is a protein that blocks TAR binding to a Tat-derived peptide, and inhibits Tat-TAR dependent transcription in HeLa nuclear extracts.[12] To understand how the β2-β3 loop of TBP6.7 (i.e., amino acids 41 to 59 of full-length TBP6.7, which corresponds to SEQ ID NO: 15) binds to the TAR bulged stem-loop, the co-crystal structure was determined at 1.8 Å resolution (FIG. 3); $R_{work}/R_{free}$=19.0/22.8% with rmsd bonds and angles of 0.010 Å and 1.36°. All TAR nucleotides are defined in electron density (FIG. 3A), and the TBP main-chain is continuous from A3 to I93.

Figure 3B:
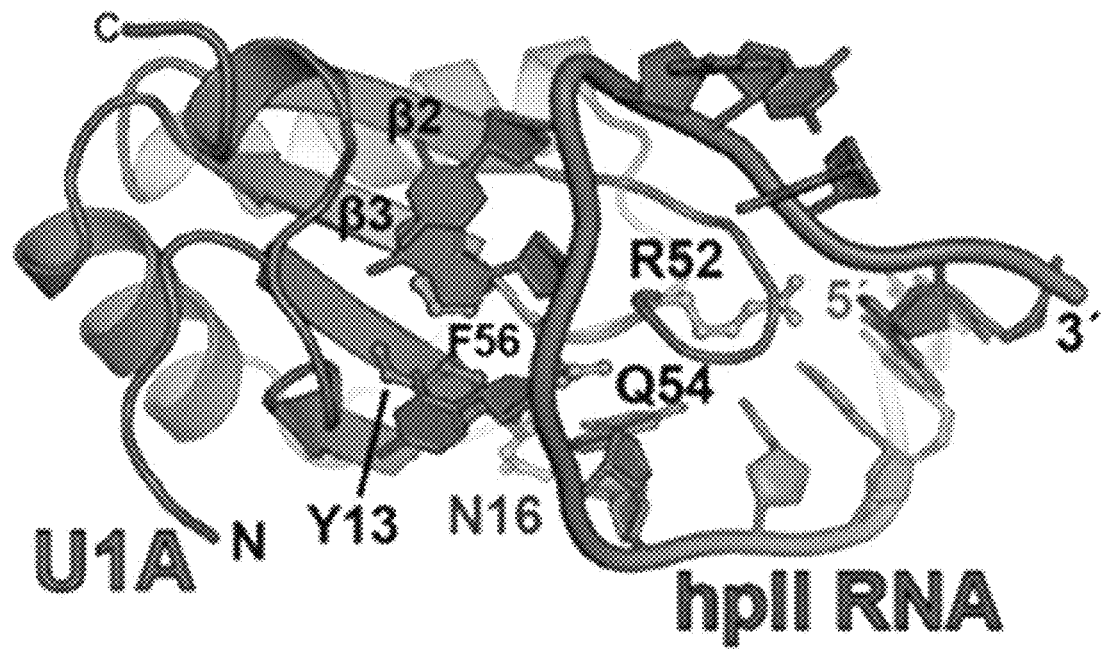
Figure 3C:
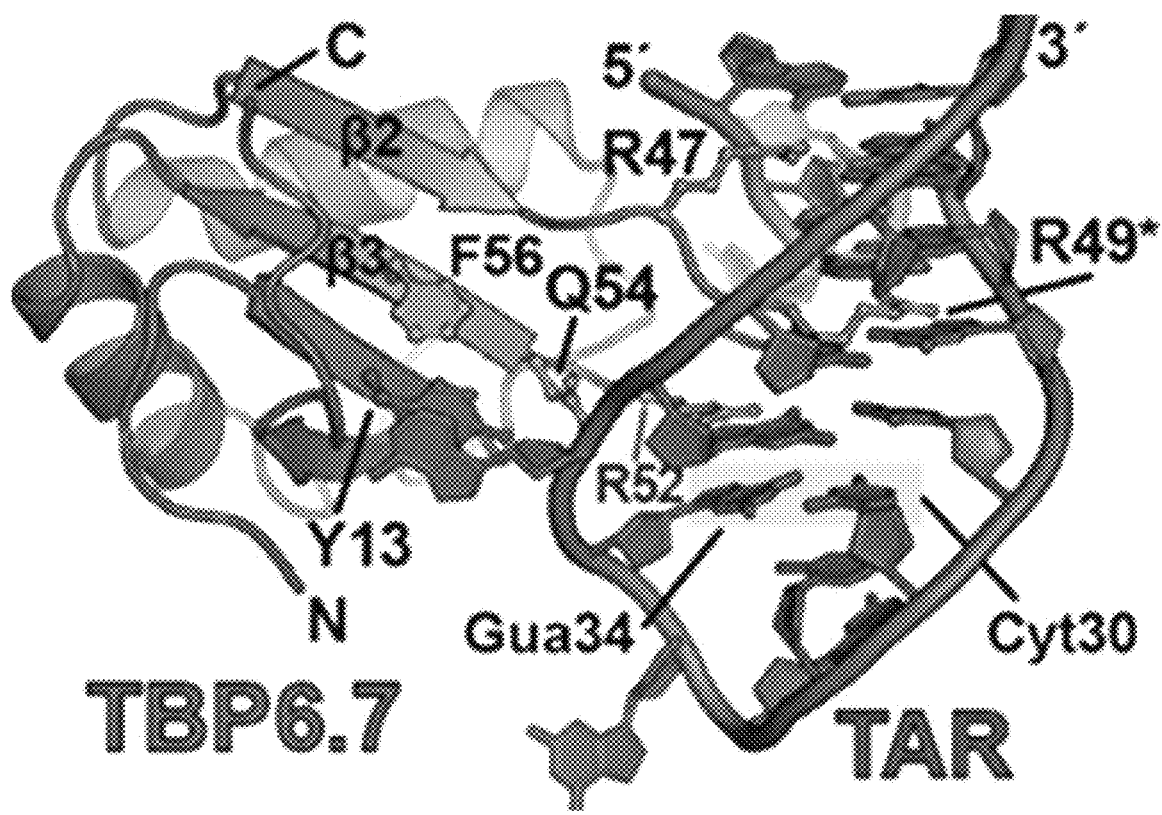

TBP6.7 adopts the same classical RRM fold as parental U1A[11] (Cα rmsd 0.85 Å), but RNA recognition differs distinctly. U1A uses RNP2 and RNP1 amino acids to recognize the single-stranded U1hpII loop (FIG. 3B). Y13 and F56 of U1A stack on Cyt10 and Ade11, whereas TBP6.7 comparably stacks Y13 of RNP2 on Ade25 (FIG. 3C). However, the double-helical fold of the TAR RNA structure prevents analogous RNP1 interactions, leaving F56 of TBP6.7 exposed. Like U1A, Q54 of TBP6.7 recognizes a 2'-OH (Gua34) whereas nearby R52 of RNP1 reads out O6 and N7 of Gua36 in TAR's major groove. Notably, R52 of U1A likewise reads N1 of Ade6 in the RNA loop and N7 in the stem-closing pair Gua16-Cyt5, but this is as close to base-specific readout by Arg as U1A gets. Importantly, the TBP6.7 β2/β3 loop conformation is altered substantially relative to U1A (3.5 Å Cα rmsd), due to changes that fine-tune it for TAR duplex recognition. P46 and P51 of TBP6.7 alter the β2-β3 loop trajectory steering R49 and R47 to read out the Hoogsteen edges of Gua28 and Gua26 (FIG. 3C and FIG. 1B). By contrast, R47 of U1A points away from U1 hpII, avoiding RNA contact. Overall, TBP6.7 binds TAR in a unique manner based primarily on a privileged β-hairpin scaffold selected to bind a duplex, rather single-stranded RNA recognition by RNP motifs.

Beyond the divergence of TBP6.7 from U1A, the observed TAR conformation is consistent with the Tat-peptide-bound state, characterized by a Uri23.Ade27-Uri38 triple (FIG. 1B) and bulged Cyt24 & Uri25[33, 34]. However, an unusual cross-loop Cyt30-Gua34 base pair is also seen (FIG. 1A and FIG. 3C, yellow box), consistent with prior chemical probing, modeling, NMR intermediate analysis, base-pairing requirements for cyclin T1 binding, and TAR sequences needed for Tat-mediated transcription[58, 110-112]. Moreover, the TBP6.7-TAR structure nicely explains TAR mutagenesis data (FIG. 4E and FIG. 4F). Specifically, the essentially of the UCU bulge (mutant hp1) is rationalized by the binding pocket it establishes for R47 (FIG. 1B). Similarly, hp2 & hp4 are detrimental because each mutant abolishes the cross-loop Cyt30-Gua34 pair, thus disrupting the Gua34-to-R52 cation-π stack and underlying R52 readout of the Gua36 Hoogsteen edge (FIG. 3C and FIG. 1B); the latter recognition is ablated by mutants hp5 & hp6. Indeed, only hp3 is tolerated, consistent with our structure in which Gua32 & Gua33 form the apex of a 'triloop', adopting bulged and stacked conformations. The fact that a rare TAR structure was observed, supported by independent and in-house biochemical data, indicates that the TBP6.7-TAR analysis is relevant.

These results reveal that TAR recognition is achieved principally by an evolved β2-β3 loop, wherein three Arg residues read the Hoogsteen edges of opposing guanines, with simultaneous cation-π stacking and salt-bridge formation to the RNA backbone (FIG. 1B). Additional protein-RNA interactions (also involving the β2-β3 loop) appear to add specificity (FIG. 1A), whereas evolved protein-protein interactions stabilize the β2-β3 loop conformation (e.g., Thr50-Arg52).

On the basis of this structural roadmap, it was hypothesized that much simpler biologics (e.g., β2-β3 loop-derived peptides) could be generated with similar affinity and selectivity to the TBP6.7-TAR complex, but with improved pharmacological properties and cell-penetration.

Example 2

The TBP6.7 Scaffold Potently and Selectively Binds HIV-1 TAR RNA

Untagged TBP6.7 was next evaluated for TAR binding using Isothermal Titration calorimetry (ITC). Additionally, point mutants Y31H and Q36R were added to TBP6.7, which facilitated prior U1A crystallization efforts. These surface mutants are distant from the TAR binding face, and we observe them in crystal contacts between TBP subunits. Notably, the extraordinarily high affinity of the TBP6.7-TAR complex requires special consideration to attain an even distribution of injection heats throughout the inflection point of the thermogram for accurate curve fitting[113]. At 20° C., the thermogram was too steep, allowing only a $K_D$ estimate of ~0.7 nM (not shown). At 37° C. curve fitting is reliable resulting in a $K_D$ of 18.5±1.4 nM (FIG. 5) and an acceptable c value of 136. The higher temperature of ITC accounts for $K_D$ differences with SPR, which was done at 20° C. (FIG. 4D and ref.[12]). The ITC shows 1:1 TBP6.7-TAR binding stoichiometry (n=1.07±0.007) with strong binding ($\Delta G$=−10.9±0.2 kcal mol$^{-1}$) driven by a favorable enthalpy ($\Delta H$=−29.5±0.3 kcal mol$^{-1}$) that offsets an unfavorable entropy (−T$\Delta$S=18.6±0.4 kcal mol$^{-1}$). The results demonstrate exceptionally tight binding.

Example 3

A Minimal β-Hairpin Retains TAR Affinity

Figure 2:
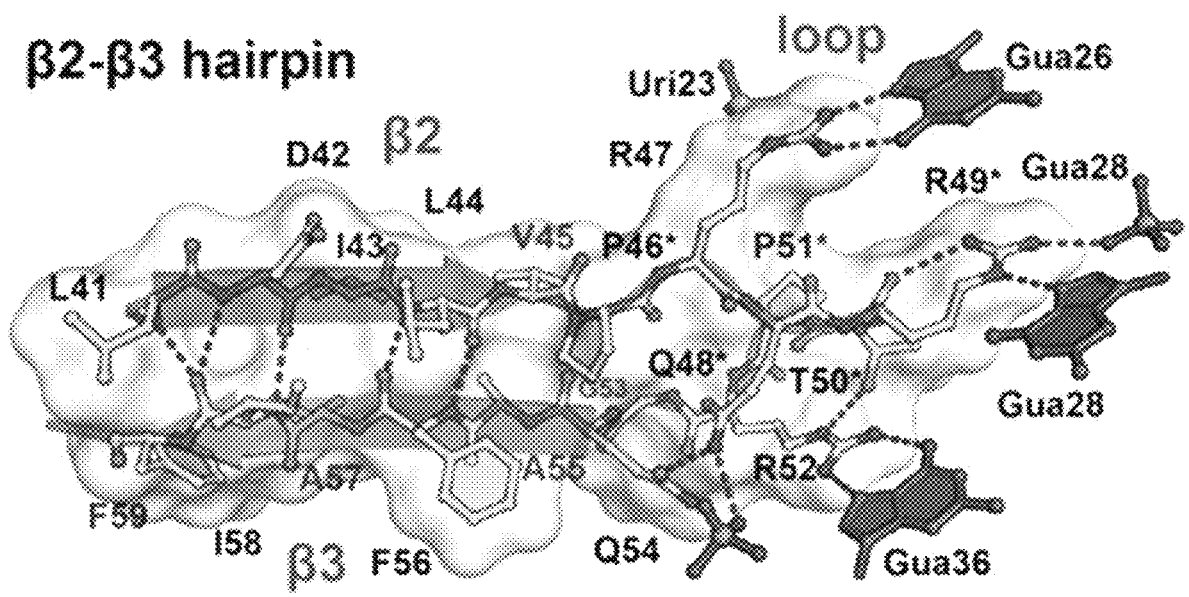
FIG. 2: depicts the β2-β3 hairpin from TBP6.7. Peptides of the present disclosure preserve the β-core, as well as amino acids and H-bond interactions that preserve the loop conformation.
Figure 6A:
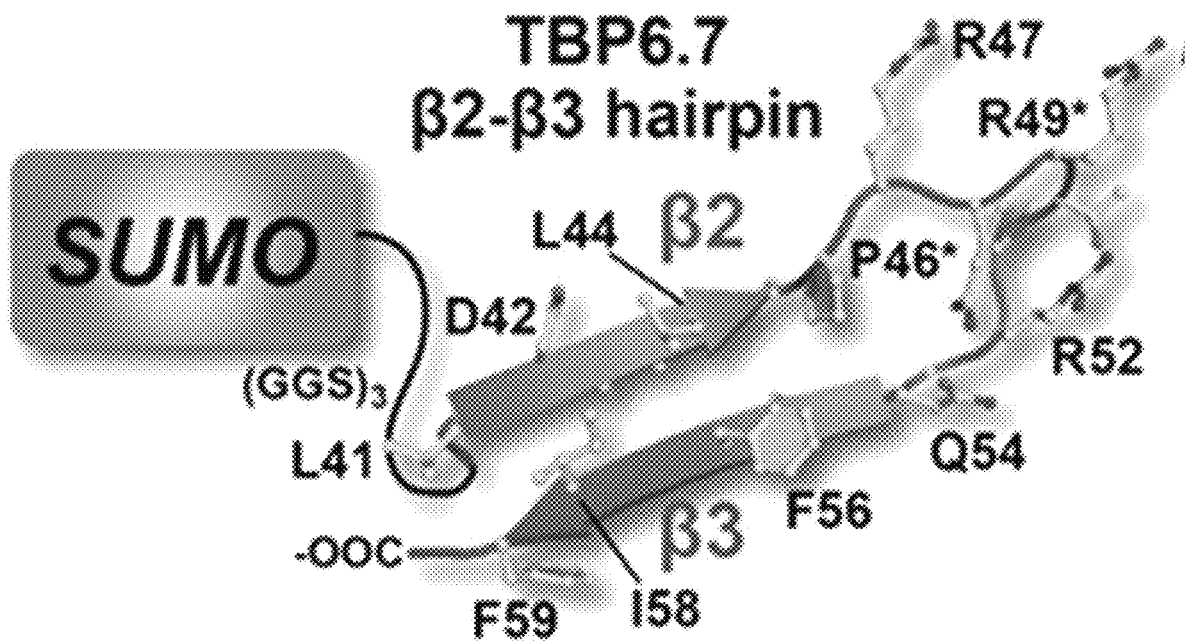
FIG. 6A-B depicts SUMO-$(GGS)_3$-β2-β3 and graphs of ELISA data. (A) Diagram of the SUMO-$(GGS)_3$-β2-β3 hairpin loop of TBP6.7 fused to SUMO. (B) ELISA data: SUMO does not bind TAR, U1hpII, or BIV; SUMO-$(GGS)_3$-β2-β3 retains affinity for TAR but does not bind U1hpII or BIV; U1A control binds U1hpII, but not TAR or BIV TAR.
Figure 6B:
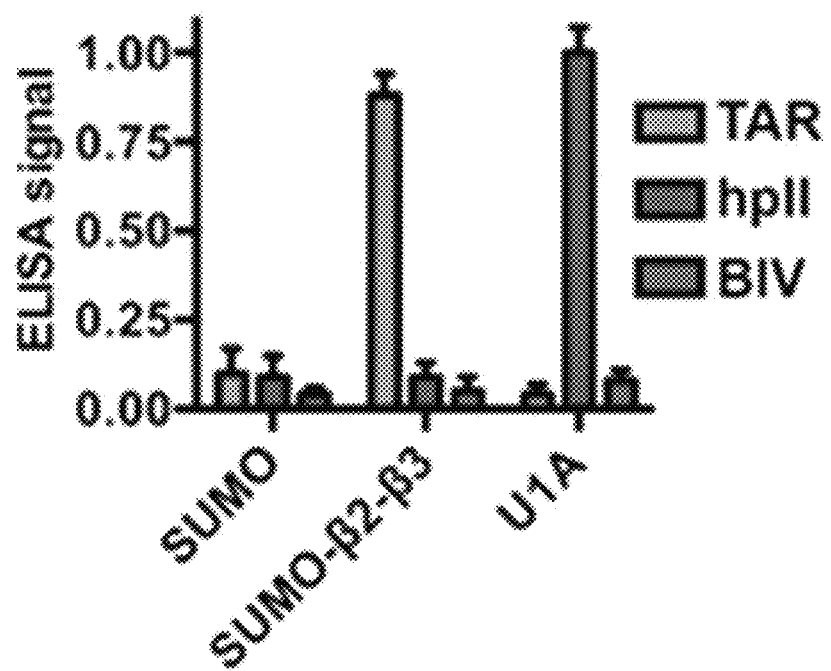

Protein engineering was used to test whether an isolated β2-β3 hairpin of TBP6.7 (FIG. 2) retains TAR binding. Specifically, a fusion protein was created comprising the TBP6.7 β2-β3 hairpin (FIG. 6A) linked by flexible, soluble spacer (GGS)$_3$ to SUMO (Small Ubiquitin-like Modifier), a 12 kDa protein that expresses well in E. coli and stabilizes a variety of structurally diverse fusion proteins.[114] The affinity for TAR was then measured by ELISA (FIG. 6B). SUMO does not have appreciable TAR binding, but the SUMO-β2-β3 hairpin fusion binds TAR. Like TBP6.7, the β2-β3 hairpin fusion shows no appreciable affinity for U1hpII or BIV TAR (FIG. 6B). This demonstrates selectivity for HIV TAR is retained.

Example 4

Cyclic Peptides

Peptides of the present disclosure are prepared by SPPS using standard protocols[136], on an automated SPPS instrument. Multiple cyclization strategies are employed. Suitable strategies allow for efficient synthesis and produce peptides that retain TAR affinity. Peptides having a full length β-loop structure (e.g. SEQ ID NO: 5-24) and truncations (e.g., shorter or no β-strands) are evaluated.

Figure 7:
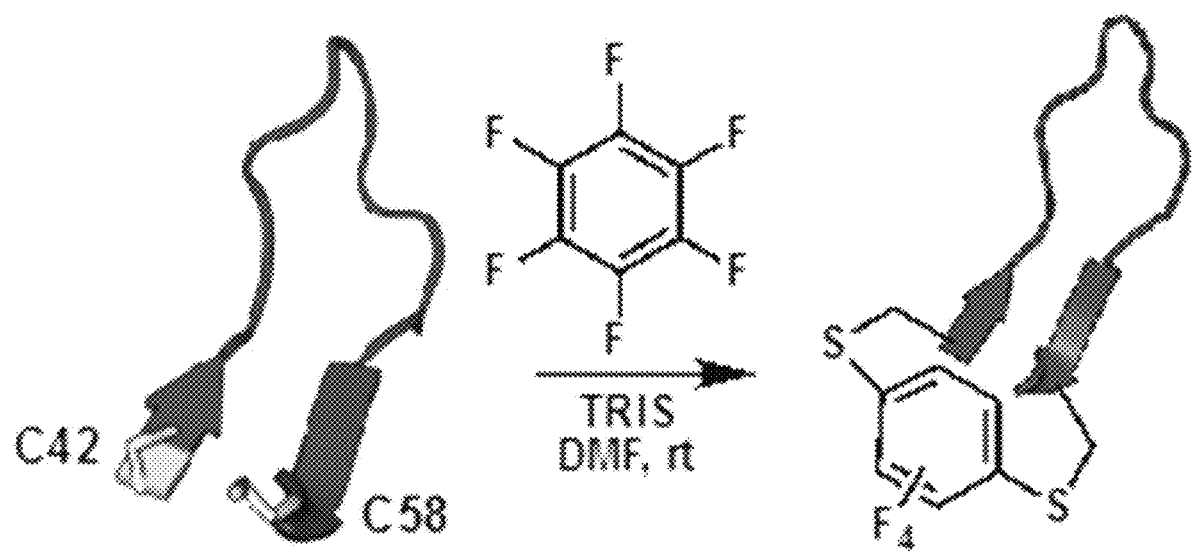
FIG. 7 depicts a scheme for the synthesis of cyclic peptides via double thiol $S_NAr$ reaction on hexafluorobenzene.

Cyclic peptides of the size described in this disclosure are prepared by a number of methods.[136, 137] In one example, on bead N- to C-cyclization is employed following previous methods[138], from linear peptides representing residues 41-59 (i.e., retaining the full β2 and β3 strands, FIG. 6A) or 44-56 (i.e., truncated β-strands). If N-to-C cyclization changes H-bonding in the β2-β3 strand (FIG. 2), thereby altering the positioning of loop residues that engage TAR, alternative strategies are used. Since the cell interior is reducing, relatively simple closure via disulfide bond formation will not be adequate but alternative strategies for ring closure using cysteines can be employed. Residues D42/I58 or L44/F56 (which occupy the same face of β2-β3 minisheet, and are thus well positioned for conjugation) can be replaced with cysteine residues and cyclization can be engaged via a tandem thiol S$_N$Ar reaction with hexafluorobenzene (FIG. 7, only the C42/C58 mutant is shown)—an approach reported previously as selective for cysteine-mediated peptide 'stapling' and cyclization[139, 140]. This reaction is assessed in solution and on solid support (as part of SPPS). In scenarios other than N- to C-cyclization, the N-terminus and C-terminus are modified to retard degradation by peptidases.[141] For example, the N-terminus is methylated and the C-terminus is converted to an amide using standard procedures.[136] Cyclic peptides are HPLC purified and composition verified by mass spectrometry.

Figure 4A:
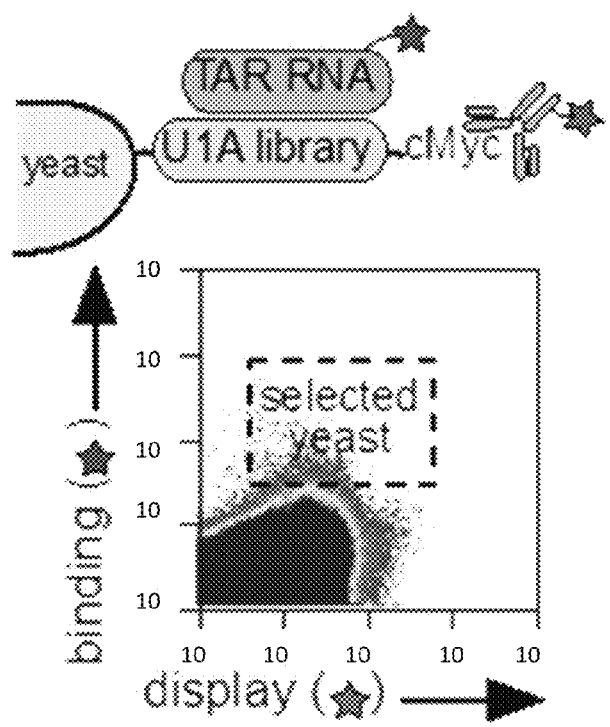
FIG. 4A-F depict the TBP evolution screen. (A) Yeast display platform to identify U1A-derived proteins that bind TAR. (B) Consensus sequences of the β2-β3 loop in 70 clones that were sequenced after six rounds of yeast display screening. (C) ELISA data depicting binding between evolved proteins and TAR. (D) SPR data showing potent and selective recognition between TBP6.6 or TBP6.7 and TAR, but not U1hpII (the starting protein's native target). As expected, U1A does not bind TAR, but tightly binds U1hpII. (E) Sequences of TAR mutants used to elucidate TBP6.6 and TBP 6.7 binding selectivity. (F) ELISA data showing relative affinities between TBP6.6 or TBP6.7.
Figure 4B:
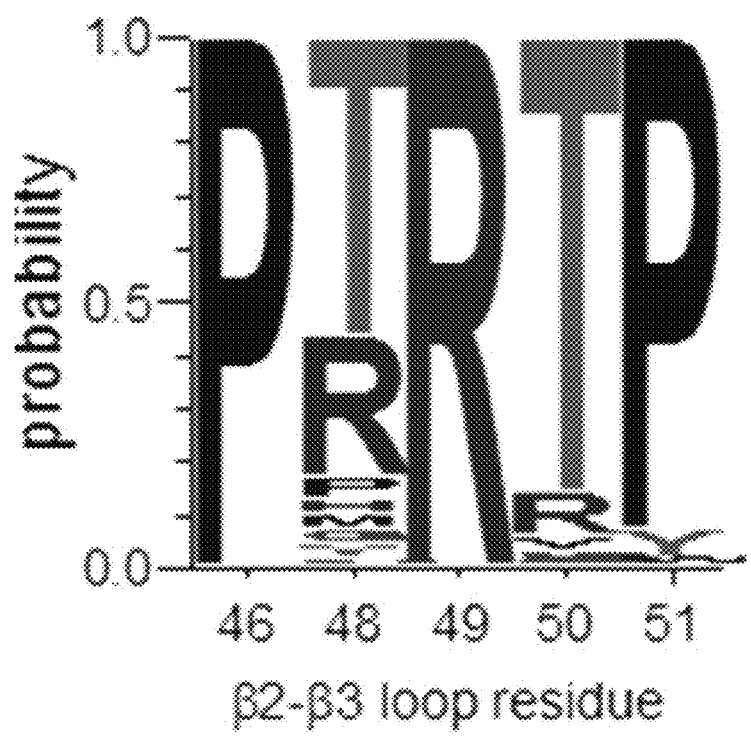
Figure 4C:
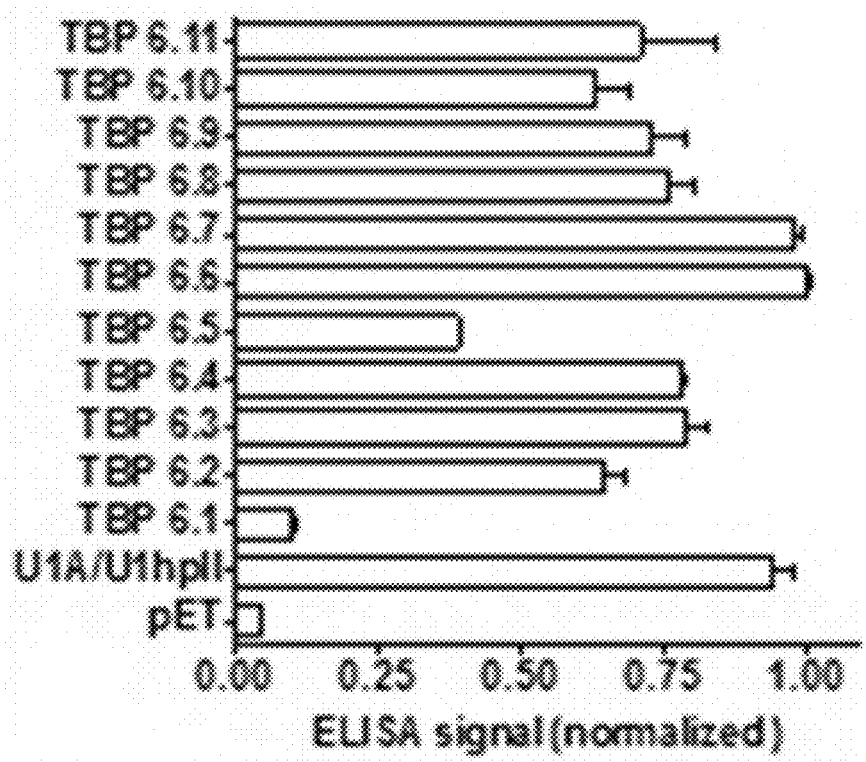
Figure 4D:
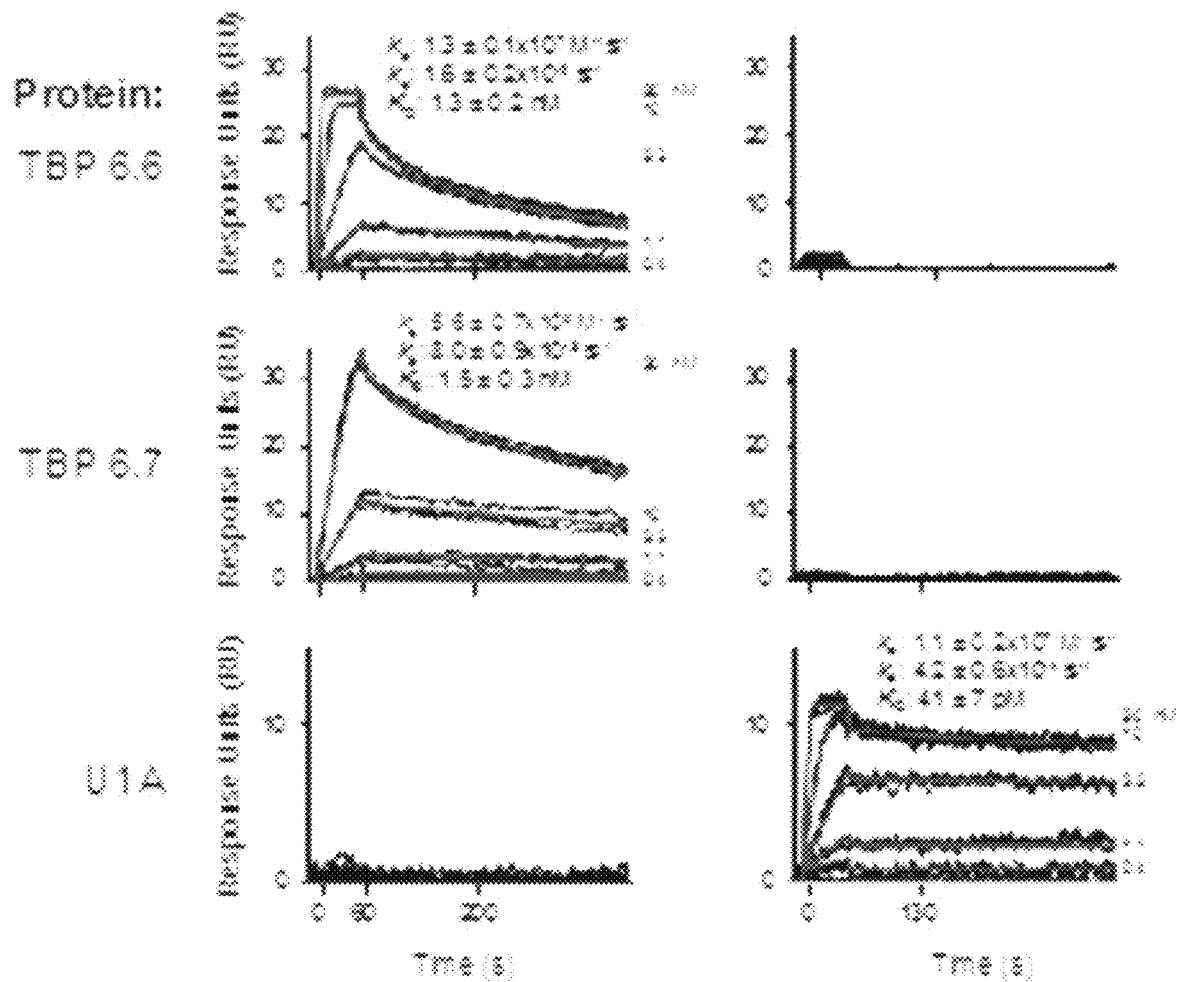
Figure 4E:
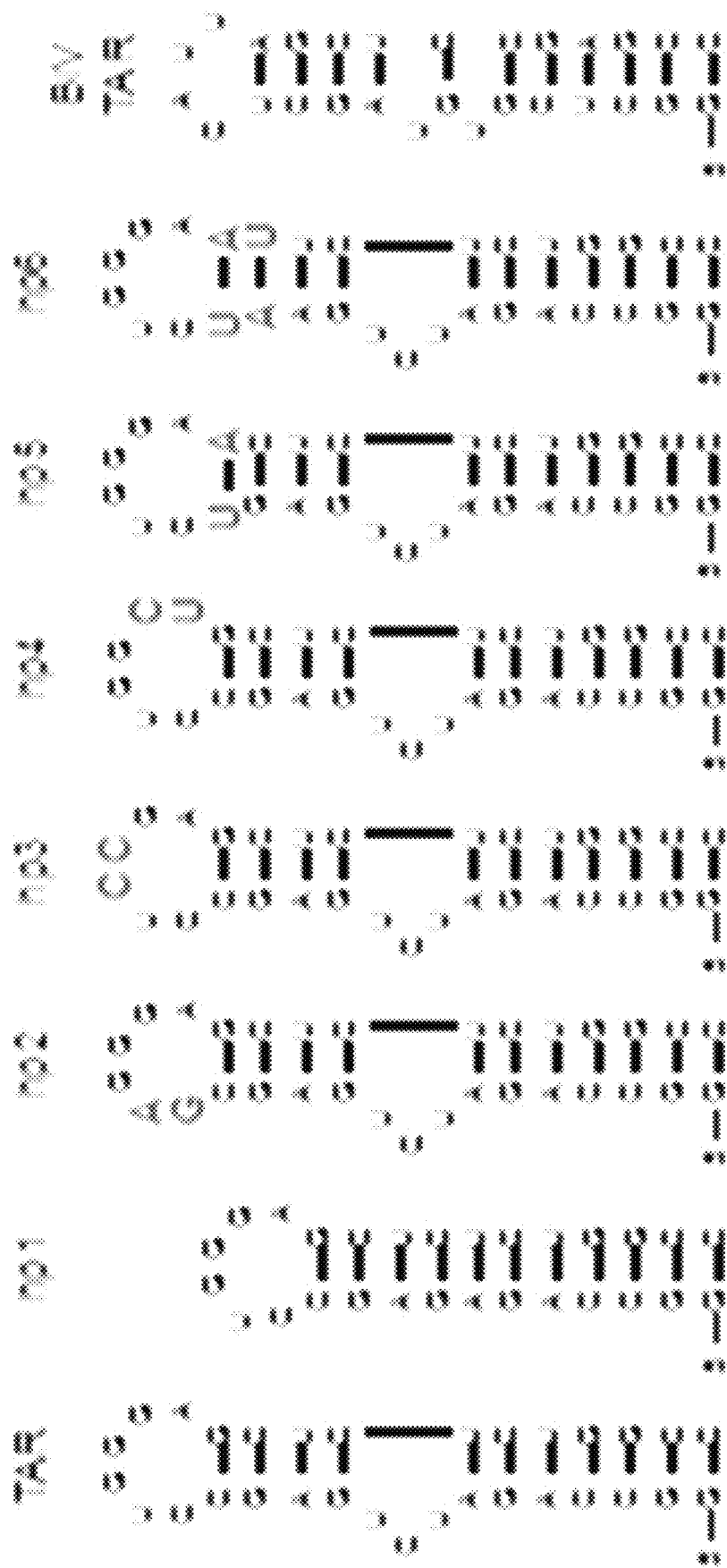
Figure 4F:
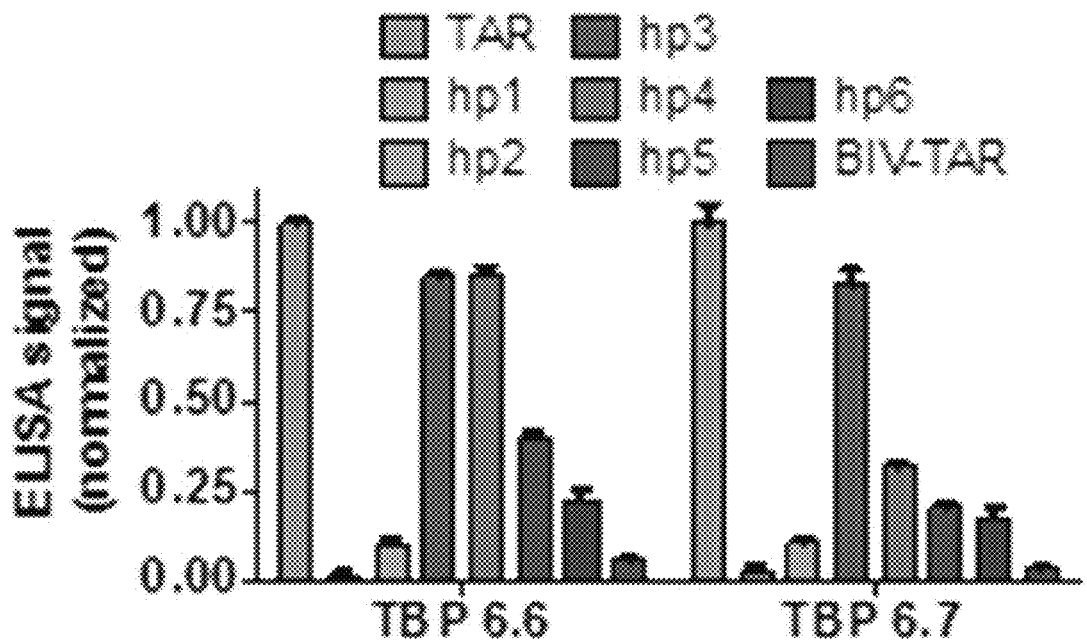
Figure 5:
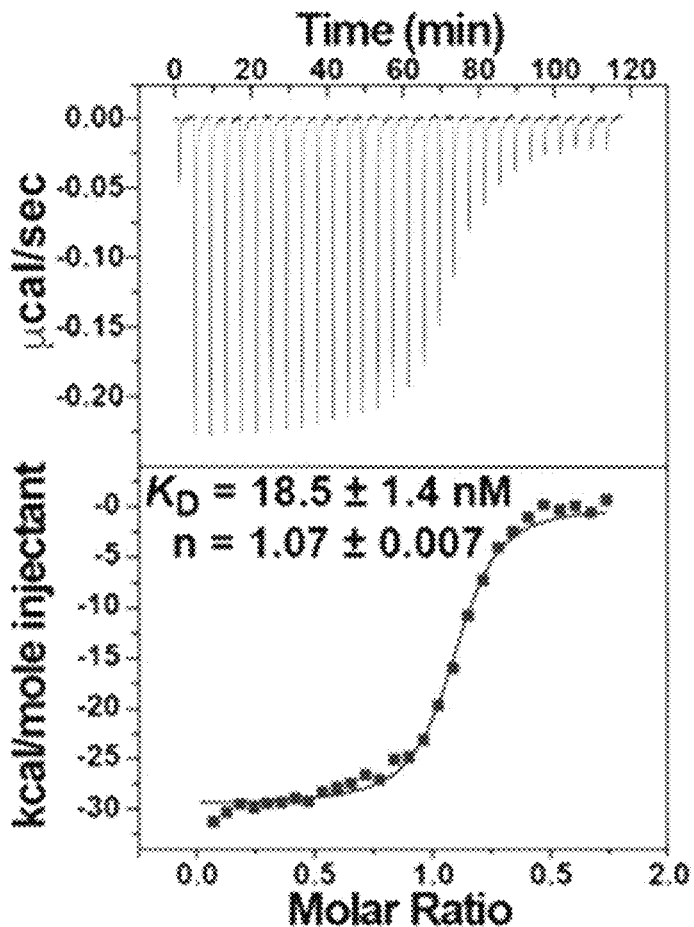
FIG. 5 shows representative ITC for TBP6.7-TAR at 37° C. in 0.05 M NaCl, 0.05 M KCl, 2 mM MgCl2, 2 mM β-mercaptoethanol at pH 7.5.

Affinity between cyclic peptides and TAR are assessed by ELISA as shown[12] (see FIG. 4C). Affinity of the tightest binding cyclic peptides are quantitated by SPR and ITC as shown[12] (FIG. 4D and FIG. 5). Binding selectivity for the tightest TAR binders are assessed with ELISA as shown[12] (FIG. 4F), by comparison to U1hpII and BIV TAR. Cyclic peptides with the best TAR affinity and selectivity profiles are then assessed for the ability to suppress or inhibit the interaction by Tat peptide and TAR, using ITC as previously shown.[12] Finally, selected cyclic peptides are assessed for the ability to suppress Tat-TAR dependent transcription in HeLa cell lysate, as previously shown.[12]

Because toxicity can vary by cell type, cyclic peptides are evaluated for each cell line employed including: 293T, HeLa, and peripheral blood mononuclear cells (PBMCs). The CellTiter 96® AQueous One Solution Cell Proliferation Assay or MTS (Promega) in which a tetrazolium compound is bioreduced to a colored formazan product by metabolically active cells is used. This assay is used to eliminate cyclic peptides that are overtly toxic prior to infectivity analysis. This assay is routinely used to assess toxicity in mammalian cells following biologic treatment.[70, 74, 78, 79, 81, 82, 142]

Concomitant with cell toxicity measurements cyclic peptide uptake by cells is measured, as well as the percent residence within endosomes or the cytosol. Cyclic and stapled[143] peptides of the size described herein—as well as similarly sized organic molecules[144, 145]—often penetrate mammalian cells. Additionally, the prevalence of arginine in the β-loops suggests that these cyclic peptides will be cell penetrating. If not, the addition of as few as three arginines into the cyclic system has been shown to promote penetration of mammalian cells by cyclic peptides[146]. Finally, the amphiphilic nature of the peptides (i.e., side-chains of β-strands are largely hydrophobic, while the evolved loop side chains are more polar, FIG. 2 and FIG. 6A) is often associated with good mammalian cell penetration.[147-150] To measure this directly, fluorescein functionalized cyclic peptides are used. Fluorescein conjugated cyclic peptides are prepared by SPPS. A β-strand residue or a penultimate residue is mutated to lysine, which is conjugated readily to a commercially available fluorescein NHS-ester using standard methods. Once prepared and purified by HPLC, fluorescein conjugated cyclic peptides are incubated with CD4-positive T-cells (Jurkat), which are representative of the cellular targets for the therapeutic leads. Following incubation, cells re washed with a PBS/heparin sulfate solution, which has been used to remove cell surface bound polypeptides.[70, 78, 79, 80-82] Fluorescence microscopy is used initially to determine if the cyclic peptides penetrate cells; an absence of punctuate foci supports residence in the cytoplasm. Using a technique previously used[70, 151], it is directly measured whether internalized cyclic peptides reside in endosomes or within the cytosol. Briefly, cells are lysed with digitonin, which disrupts the cell membrane but not endosomes. Following centrifugation and concentration, lysate are blotted onto nitrocellulose and incubated separately with anti-fluorescein, anti-Erk/1/2 (a cytosolic marker) or Rab5 (an endosomal marker). Following incubation with a near IR dye-labeled secondary antibody, each blot is imaged. Lysate that tests positive for fluorescein and Erk1/2, but not Rab 5 reveal that the fluorescein-labeled peptide resides in the cytosol. Lysis generated from RIPA buffer (which disrupts both the cell membrane and endosomes) are used as a control to reveal material that resides only in endosomes.

While most cyclic peptides of the type and size presented here penetrate mammalian cells placing them in the cytosol, if the cyclic peptides are not cell-penetrating, or reside in endosomes, cell-penetrating and/or endosomolytic sequences[155] are conjugated to the peptides (opposing the β2-β3 loop).

Example 5

Mechanism of Action

Cyclic peptides are validated for the mechanism of action (MOA) based on their dose-dependent ability to: (i) inhibit Tat-mediated LTR-driven expression of luciferase in TZM-bl HeLa reporter cells following infection with pseudotyped HIV; (ii) inhibition of Tat-mediated elongation of full-length viral transcripts in HEK293T producer and TZM-bl reporter cells[156]; and (iii) inhibition of live virus in spreading infection assays.

The pseudotyped HIV proviral vector encodes all HIV genes but nef (replaced by EGFP) and env. This enables dose-dependent determination of cyclic peptide competition with Tat by quantifying: (i) full-length viral transcripts in 293T and TZM-bl cells using primers comprising polyA and upstream viral sequences to prime RT-PCR[157], (ii) viral particle yield (p24 detection), and (iii) effects on viral particle integrity (i.e., based on their infectivity of TZM-bl cells not treated with peptides). These experiments establish the MOAs, and provide controls prior to single-round infectivity and live-virus testing.

HEK 293T producer cells (standard in the field) are transfected with proviral vector and trans complementing cDNAs that provide envelope functionality. Viral particles are harvested from media 24 hr after transfection by 0.45-μm filtering. Viral load for infection of TZM-bl cells are normalized by p24 ELISA (Perkin Elmer). The ability of cyclic peptides to compete with Tat—expressed by these virions following TZM-bl infection—is determined by treating cells with a seven-point dose range of each cyclic peptide (100 nM to 25 μM) prior to infection; 6, 12, 24 and 48 hr post-infection cells are quantified for luciferase expression. Infections of untreated and cyclic peptide-treated TZM-bl cells in 96-well plates (10,000 cells/well) with 500 pg p24/well will proceed for 48 hr before addition of Steady-Glo™ (Promega). Relative luminescence units (RLU) are quantified to assess infectivity changes for each cyclic peptide relative to infected cells without peptide (i.e., the maximum luminescence signal from Tat activation of LTR transcription).

This assay is conducted to identify cyclic peptides vetted by single-cycle infectivity (above) that show dose-dependent antiviral activity with a high therapeutic index (efficacy/toxicity). The activity of cyclic peptides is evaluated against isolates from 9 viral clades with different tropisms, along with 7 single- and multi-drug resistant strains. Briefly, cyclic peptides with the maximum Tat-dependent antiviral activity (above) are assayed in a standard spreading infection of pooled PBMCs using live HIV-1. Test cPepTb dilutions are prepared at a 2× concentration and 100 μL of each concentration placed in appropriate wells. 100 μL of a pre-determined dilution of virus stock is placed in each test well (final MOI≅0.1). Identical plates are prepared without virus for cyclic peptide cytotoxicity assays. PBMC cultures are maintained at 37° C. with 5% $CO_2$. Seven days after infection, cell-free supernatant are analyzed for reverse transcriptase activity, and cyclic peptide cytotoxicity is assayed by MTS on the separate cytotoxicity plates. Data analysis will include: $IC_{50}$ (50% inhibition of virus replication), $IC_{90}$ (90% inhibition of virus replication), $TC_{50}$ (50% cytotoxicity), and therapeutic index (TI=TC/IC; i.e., the antiviral index or AI). Deliverables are cyclic peptides with a high therapeutic index.

Example 6

Minimal TAR-Binding Peptides Retain HIV-1 TAR-Binding Function

To understand how TBP6.7 recognizes TAR with exceptional affinity and specificity, the co-crystal structure at 1.80 Å resolution under low salt conditions at neutral pH (Table 1). The protein main-chain electron density is continuous from V3 to A95 with discernible side-chain rotamers and carbonyl oxygens at most positions; all nucleotides of the TAR 27-mer are well defined with obvious sugar puckers. Refinement statistics include $R_{work}/R_{free}$ values of 18.5/22.0% with acceptable bond and angle deviations of 0.014 Å and 1.6°. These quality indicators provide confidence in the observed mode of protein-mediated TAR recognition.

The TAR fold herein is consistent with prior structural features observed by NMR for TAR complexes with small-molecules. Specifically, the TAR 27-mer comprises helical stems S1a and S1b interrupted by the Uri23.Ade27-Uri38 triple. The flanking UCU-bulge extrudes bases Cyt24 and Uri25 from the duplex core, consistent with solution studies. The apical loop exhibits a canonical Cyt30-Gua34 pair separated from S1b by bulged base Ade35. Hexaloop bases Gua32 and Uri31 stack on Cyt30, whereas Gua33 projects outward. Overall, the apical loop features of the co-crystal structure agree well with NMR assignments, chemical probing, modeling, sequence conservation, and the requirement of the Cyt30-Gua34 base pair for TAR binding to cyclin-T1.

Comparison of the TBP6.7 fold to the U1A structure revealed that the evolved protein adopts the same classical mixed α/β topology as parental RRM1. A superposition of Cα atoms produced a modest rmsd of 1.1 Å, although some local conformational differences are apparent. Regions of greatest variation include the β2-β3 loop (amino acids 46 to 51 with an rmsd of 3.9 Å), and the C-terminus (amino acids 91 to 95 with an rmsd of 3.6 Å). Each region was subjected to yeast display maturation to elicit TAR binding. When both proteins are oriented similarly, it is clear that TBP6.7 and U1A engage their RNA targets differently. TBP6.7 binds the TAR duplex at S1b burying 1555 Å$^2$, whereas U1A recognizes mostly single-stranded RNA in the U1hpII loop between Ade66 and C72. The preponderance of specific contacts to TAR originates from the β2-β3 loop.

Recognition of Duplex Versus Single-Stranded RNA by TBP6.7 and U1A: Having established that the TBP6.7 structure maintains the classical RRM fold, studies were undertaken to determine if TBP6.7 uses the underlying set of conserved RNP amino acids for RNA binding. This point is especially significant because RNPs function in single-stranded RNA recognition, whereas TBP6.7 engages the TAR duplex. In U1A, Y13 of RNP2 and F56 of RNP1—located in β1 and β3—stack on bases Cyt70 and Ade71. Although Y13 of TBP6.7 stacks on Ade25, F56 does not engage TAR due to the lack of bulged, unpaired bases in this region where the core fold forms a duplex. The Q54 amide of U1A RNP1 approaches the 2'-OH of Gua69 in U1hpII but does not interact, whereas the amide NO of TBP6.7 H-bonds to the 2'-OH of Gua34 in TAR—consistent with its role in RNA readout in other RRMs. Finally, R52 of RNP1 recognizes the Hoogsteen edge of the loop-closing pair Gua76-

Cyt65 in U1hpII, as well as Gua36 in TAR. The former interaction is the only instance of Arg-mediated base readout by U1A, and its simultaneous recognition of Ade66 N1 yields a non-optimal, inclined guanidinium-guanine interaction. A major finding is that TBP6.7 utilizes its RNP motifs to bind the TAR duplex, although the preponderance of its affinity and specificity appears to arise from contacts contributed by the evolved β2-β3 loop, thus distinguishing it from U1A.

TBP6.7 Specificity Relies on Three Arginines to Read the TAR Major Groove: ITC analysis of the TBP6.7-TAR complex showed a $K_{D,App}$ of 2.5±0.1 nM (Table 2), consistent with tight binding measured by surface plasmon resonance. From the analysis of the co-crystal structure, binding interactions were parsed into four groups: (i) β2-β3 loop arginines that read major-groove guanines to impart specificity; β2-β3 loop residues that add affinity by interaction with the backbone or 2'-OH groups; (iii) evolved protein-protein interactions that stabilize the β2-β3 loop; and (iv) interactions outside the β2-β3 loop that impart affinity. Mutants from each category were prepared to test specific structural observations. Each amino acid was changed to Ala to disrupt TAR binding without the potential to form new interactions.

Of the three arginines in the TBP6.7 β2-β3 loop, R52 exhibits the fewest interactions with TAR, making it straightforward to assess their energetic contributions to binding. The guanidinium group donates H-bonds from NH1 and NH2 to the N7 and O6 moieties of Gua36, while forming a cation-π interaction involving Cζ and the imidazole of Gua34 in the apical loop. Accordingly, R52A reduced binding by a factor of 116, resulting in a ΔΔG of +2.8 kcal mol$^{-1}$. This value is consistent with prior observations that suggest a single H-bond contributes ~0.5 kcal mol$^{-1}$ and a cation-π interaction is worth ~1.8 kcal mol$^{-1}$.

R49 of TBP6.7 is the only arginine that resulted from selection. Its side-chain makes more contacts to TAR than R47 by positioning the guanidinium group to form H-bond and salt-bridge contacts that readout N7 and the pro-$R_p$ backbone oxygen of Gua28, while forming a cation-π contact with Ade27. As such, R49A TBP6.7 mutant yielded a ΔΔG of +3.3 kcal mol$^{-1}$, corresponding to a loss in binding by a factor of 284 (Table 2). The energetic loss is consistent with the observed structural interaction comprising: a H-bond of ~0.5 kcal mol$^{-1}$; an exposed salt-bridge of ~1 kcal mol$^{-1}$; and a non-optimal cation-π contact between Cζ of R49 and the Ade27 imidazole worth ~1.8 kcal mol$^{-1}$.

R47 is present in the U1A sequence but it does not make contacts to the U1hpII RNA. In contrast, R47 of TBP6.7 makes the most extensive number of contacts with TAR relative to any arginine in the co-crystal structure. The R47 guanidinium forms 'arginine fork' interaction whereby NH1 and NH2 groups H-bond to O6 and N7 of the Gua26 base, while its Nε and NH2 groups form H-bond and salt-bridge contacts to O5' and the pro-$R_p$ oxygen of Uri23. Simultaneously, the guanidinium is sandwiched between the bases of Ade22 and Uri23 forming cation-π interactions consistent with other protein-RNA complexes. To assess its binding contribution, the R47A TBP6.7 mutant was made, which yielded a ΔΔG of ~+3.8 kcal mol$^{-1}$ corresponding to a loss in binding of ~600 (Table 2). R47K was not as severe with ΔΔG of +2.5 kcal mol$^{-1}$, corresponding to reduction in binding by a factor of 160 (Table 2). The latter observation is consistent with the ability of lysine Nε to salt bridge with the Uri23 phosphate while retaining cation-7 stacking, as well as possible H-bonding to Gua26. Although the severity of the R47A mutant makes it difficult to measure and relate specific energetic contributions to the structure. An estimated 324 Å$^2$ of buried area is lost for this mutant, which is nearly double that of R52A. From this analysis it is clear that R47 is a key amino acid in TAR binding and specificity. Overall, the solution ITC measurements support the crystallographic observations, demonstrating the importance of each β2-β3 loop arginine for TAR recognition Amino Acids Contributions from the β2-β3 Loop and C-Terminus to Tar Binding: Other β2-β3 loop amino acids of TBP6.7 observed to bind directly to TAR were next evaluated by mutagenesis. Q48 of TBP6.7 H-bonds to the pro-$R_p$ O of Gua36 in a non-specific manner that appears to add affinity rather than specificity. The Q48A TBP6.7 mutant reduced binding by a factor of two, resulting in a modest ΔΔG of +0.4 kcal mol$^{-1}$, consistent with loss of one H-bond (Table 2). Q48T was then evaluated. The mutant side-chain is likely too short to interact with TAR, but binding was lowered by a factor of only 1.4, resulting in a subtle ΔΔG increase of +0.2 kcal mol$^{-1}$ (Table 2). This small change and the ability of T48 Oγ1 to form an H-bond suggest a favorable new interaction likely occurs.

Q54 of TBP6.7 was next evaluated because it binds TAR at the 2'-OH group of Gua34 of the apical loop, noted as an RNP1 interaction. The loss in binding for Q54A TBP6.7 mutant was only a factor of 2.2 with a ΔΔG of +0.5 kcal mol$^{-1}$ (Table 2), consistent with a single H-bond. Such amino acids are consistent with individual H-bond interactions that recognize RNA backbone or sugar features, rather than sequence specific readout observed for R47, R49 or R52.

Mutagenesis was also used to determine if specific, evolved protein-protein contacts contribute to TAR binding by stabilizing the loop conformation. Although neither P46 nor P51 of TBP6.7 engages in classic turn interactions, each adopts type II pro helix main-chain dihedral angles that position the pyrrolidine within van der Waals contact of nearby residues. Cγ and Cδ of P46 abut the aromatic ring edge of RNP1 residue F56 in a hydrophobic pocket. The P46A TBP6.7 mutant is devoid of these contacts, and reduces binding by a factor of four with a ΔΔG of +0.9 kcal mol$^{-1}$ (Table 2)—consistent with its role in loop stabilization. Similarly, Cγ of P51 borders O4' of Cyt24 in the UCU bulge. The P51A TBP6.7 mutant reduces TAR binding by a factor of 3.7 with ΔΔG of +0.8 kcal mol$^{-1}$ (Table 2), suggesting a minor role in loop stabilization. To complete the analysis of this amino acids class, T50 of TBP6.7 was examined. T50 of TBP6.7 forms an H-bond to Nε of R52 that steers the guanidinium group into the Gua36 Hoogsteen edge. The T50A TBP6.7 mutant reduces binding by a factor of four with a ΔΔG of +1.0 kcal mol$^{-1}$ (Table 2), consistent with the greater strength of neutral-to-charged H-bonds interactions.

The U1A C-terminus forms a short helix that interacts with U1hpII at residues 91, 92 and 94. These positions were diversified and subjected to selection, but no clear consensus emerged. The co-crystal structure revealed no appreciable interaction between the TBP6.7 C-terminus and RNA. To corroborate this observation, we truncated TBP6.7 after residue 90. ITC analysis revealed a reduction in binding by a factor of 3.9, and a ΔΔG of +0.8 kcal mol$^{-1}$ (Table 2). A plausible explanation for this modest binding contribution is that K91 makes van der Waals contacts to F56 of RNP1, and R52 makes H-bonds to the carbonyl oxygen of nearby K60, which likely favor the core fold.

Minimal TAR-Binding Peptides Retain HIV-1 TAR-Binding Function: The TBP selection approach[12] led to the identification of a privileged peptide sequence for high-affinity TAR recognition. It was then discovered that RNA specificity is achieved primarily by three arginines and flanking residues in the β2-β3 loop. The loop conformation is stabilized by evolved residues P46, T50, P51, and an intra-amino acid H-bond between the R49 carbonyl oxygen and its NH1 moiety. This loop joins antiparallel β-strands with typical backbone H-bonding, and hydrophobic side-chain packing. As such, we hypothesized that the β2-β3 loop is a supersecondary structure capable of binding TAR RNA outside the context of the TBP6.7 protein.

To test for TAR binding by the isolated β2-β3 loop sequence, we first fused this short peptide to SUMO (Small Ubiquitin-like Modifier). The results revealed that TAR binds the β2-β3 loop when fused to SUMO, whereas non-cognate RNA sequences, such as BIV TAR and U1hpII, did not elicit significant binding. As expected, SUMO alone showed no appreciable RNA binding, whereas U1A produced the highest relative level of binding to its cognate target, U1hpII, but did not interact with BIV or HIV TAR. Arg-to-Ala mutants were then tested. The R47A, R49A and R52A mutants each lowered the extent of SUMO-β2-β3 loop binding to HIV TAR, and did not enhance interactions with non-cognate RNAs. These data suggest that the isolated β2-β3 loop interacts with HIV TAR in the arginine-dependent manner established by the co-crystal structure.

To reduce conformational flexibility while promoting formation of the β2-β3 supersecondary structure, a "stapled" peptide variant of the β2-β3 loop was prepared on the E. coli surface. In this context, the cyclic peptide produced a $K_{D,App}$ of ~80 nM, whereas BIV TAR and U1hpII RNAs did not interact appreciably. Stapled peptides harboring R47A, R49A or R52A mutations were each impaired in their ability to bind HIV TAR, supporting the mode of peptide-RNA binding in the co-crystal structure.

Inhibition of Tat-Peptide Binding and Tat-Mediated Transcription: Experiments were then performed to determine if cyclic peptides comprising the β2-β3 loop are capable of blocking Tat peptide binding. Prior work demonstrated that short peptides of the Tat basic domain can mimic the protein's interaction with TAR, providing a means to assess the efficacy of TAR-binding molecules that compete with Tat. Intact TBP6.7 inhibited Tat-peptide binding when pre-incubated with TAR, but closely related TBP6.6 did not show inhibition, suggesting that TBP6.6 binds TAR in a region that does not overlap Tat. SUMO-β2-β3 loop proteins compete with the TAR-Tat peptide interaction, which has a measured $K_D$ of ~260 nM, but the various R-to-A variants within the β2-β3 loop do not compete well. These results demonstrate that peptides of the isolated β2-β3 loop have Tat-inhibitory properties similar to intact TBP6.7.

Finally, studies were performed to determine if cyclic peptides could block Tat-dependent in vitro transcription in HeLa cell nuclear extracts. As with TBP6.7, concentration-dependent suppression of Tat-mediated transcription was observed in the presence of a cyclic peptide harboring the β2-β3 loop.

Molecular Dynamics Supports Stability of TBP6.7-TAR Interactions: TAR-peptide complexes show a variety of low-energy conformations in the solution ensemble in which distinct arginines alternate between RNA-bound and free states. To interrogate the dynamics of the TAR-TBP6.7 complex, the coordinates were subjected to molecular dynamics (MD) and the average occupancy of interactions were quantified over multiple trajectories spanning a total of >20 μs. To provide a basis for comparison, trajectories were ran on: (i) isolated TAR RNA; (ii) TAR-TBP6.7; and (iii) TAR-(β2-β3 loop cyclic peptide). Trajectories of the unbound TAR RNA showed remarkable agreement with prior free-state features including: dissolution of the U•A-U major-groove base triple, unstacking of bases Uri31 and Gua32 in the apical loop, and sequestration of the S1b major groove. In contrast, the TAR-TBP6.7 and TAR-peptide trajectories each exhibit stable U•A-U base triples. In general, Cyt30-Gua34 base pair of the apical loop was stable on the timescale of analysis, although bulged base Ade35 made transient excursions into the apical loop to form a minor groove interaction with Cyt30. The latter observations are consistent with ground and excited state conformation of TAR. Despite bulged Gua33 making a crystal contact with bulged Cyt24' of a neighboring molecule, neither base was foisted inside the apical loop or duplex during MD trajectories.

An analysis of contacts made between the β2-β3 loop of TBP6.7 to TAR S1b revealed that specific interactions observed in the crystal structure show variations during MD. Specifically, side-chains that make single H-bonds to the backbone, such as Q48 and Q54, are transient. In contrast, sequence-specific H-bond contacts between arginine and the major-groove edge of guanine are more persevering, whereas arginine contacts to the RNA backbone, such as R49, seem to fluctuate. Guanidinium groups in more sequestered environments appear to maintain interactions longer in the order: R47>R49*>R52; this trend also follows the measured thermodynamic stability (Table 2). Notably, all interactions appeared to be sustained longer in the context of the TAR-TBP6.7 complex compared to the TAR-(β2-β3 loop peptide) complex, which could reflect the absence of stabilizing interactions contributed by the overall protein fold. Surprisingly, the base-specific readout achieved by each arginine of the β2-β3 loop was sustained well in MD simulations of the TAR-peptide complex, which agrees with the biochemical data that the cyclic peptide retains TAR binding, and can block Tat-peptide binding in solution and HeLa extracts.

Importance of Individual Arginines: Each arginine recognizes a specific guanine in the major groove but also utilizes conformational features of TAR, such as the U•A-U triple and apical loop that distinguish it from A-form duplexes. In this manner, TBP6.7 appears to avoid interactions with other RNAs such as Bovine immunodeficiency virus TAR and U1hpII. Notably, each arginine of the TBP6.7 β2-β3 loop recognizes a strictly conserved guanine in TAR, suggesting that TAR RNA recognition by TBP6.7 will be preserved over most HIV-1 clades and circulating recombinant forms.

Production of TBP6.7 and TAR RNA for Isothermal Titration Calorimetry (ITC). TBP6.7 and mutants thereof was prepared by production of a synthetic gene based on the human U1A sequence used in structural studies including crystallization mutants Y31H and Q36R. TAR strands ranging in size from 25 to 31-mers were produced by chemical synthesis (GE Lifesciences), and purified by denaturing PAGE. Lyophilized RNA was suspended in a folding buffer comprising 0.050 M Na-HEPES pH 7.0 containing 0.10 M NaCl. The RNA was heated to 65° C. for 5 min followed by addition of 0.006 M $MgCl_2$ before slow cooling. Samples were then incubated at 37° C. for 20 min followed by flash cooling on ice. Isothermal titration calorimetry (ITC) measurements were conducted using a VP-ITC calorimeter (MicroCal, Inc.) as described (68) in which the folding buffer above included 0.006 M $MgCl_2$ or 0.0005 M EDTA to produce ITC buffer. Each sample was dialyzed at 4° C. overnight against 4 L of ITC buffer. RNA was diluted with dialysis buffer to 3.1-3.3 μM for wild type Fpr, 3.2-7.8 μM for the A52G and A84G Fpr mutants, 10.5-15.7 μM for the C7U and U17C Fpr mutants, 2.4-3.6 µM for 74 env, and 1.8 µM for 74 env-s2Δ30-43. PreQ$_1$ was dissolved in dialysis buffer at concentrations ~10-fold higher than RNA. Thermograms were analyzed with Origin 7.0 (MicroCal) using a 1:1 binding model. Average thermodynamic parameters and representative thermograms with curve fits are provided (Table 2).

Crystallization and X-Ray Data Collection: TAR RNA was dissolved to 0.16 mM in 0.010 M Na-cacodylate pH 7.0. RNA was folded by heating to 65° C. for 3 min followed by addition of 0.006 M MgCl$_2$ and 0.32 mM preQ$_1$; subsequently, the RNA was heated to 65° C. for 5 min, followed by slow cooling and 0.2 µm filtration. Crystals were prepared by the hanging drop vapor-diffusion method in which 1.6-2.0 µL of folded RNA was mixed with an equal volume of well solution, followed by equilibration over 1 mL of well solution at 20° C. Crystals grew as isosceles trapezoidal plates within 3 d and achieved a maximum size of 0.2 mm×0.2 mm×0.015 mm within 3 weeks. The well solution used to prepare a 'native' crystal of the PM construct with a G•U pair was 74.5% Tacsimate pH 7.0 (Hampton Research), 0.050 M MOPS pH 7.0, 0.020 M Co(NH$_3$)$_6$Cl$_3$, and 0.001 M spermine•HCl. The well solution used to prepare a heavy-atom-derivatized PM crystal contained 1.9 M Na-malonate pH 7.0 (Hampton Research), 0.20 M CsCl$_2$, 0.050 M Na-MOPS pH 7.0, 0.050 M Mg(C$_2$H$_3$O$_2$)$_2$, and 0.001 M spermine•HCl. Crystals of the wild type sequence used for "high-resolution" refinement were prepared from a well solution of 85% Tacsimate pH 7.0, 0.010 M Mg(C$_2$H$_3$O$_2$)$_2$, 0.006 M Co(NH$_3$)$_6$Cl$_3$, and 0.001 M spermine•HCl. All crystals were flash frozen by washing in well solution supplemented with 0.32 mM preQ$_1$, then plunging into N$_2$(l). X-ray diffraction data for phasing were recorded at the Stanford Synchrotron Radiation Lightsource (SSRL, Menlo Park, Calif.) beam line 12-2 and were reduced with XDS/XSCALE (41) (Table 1).

Phase Determination, Refinement, and Analysis: Phases were obtained by molecular replacement in Phenix starting from the U1A coordinates devoid of U1hpII. Phenix.Auto-Build (42) was used to trace the backbone, followed by iterative use of Phenix.refine interspersed with manual building in Coot. The resolution of the structure was extended to 2.75 Å resolution using data from an isomorphous crystal with the wild type Fpr sequence. The structure converged on R$_{cryst}$/R$_{work}$/R$_{free}$ values of 21.4%/21.2%/22.8% with acceptable geometry, and a clash score of 1.24 (Table 1). The quality of the refined structure is indicated by the clear electron density for all nucleotides, except a break at positions 34 and 35 within the P3 loop. PreQ$_1$ is visible in omit and unbiased electron density maps that define its placement in the structure; the ligand-binding pocket is free from crystallographic contacts.

Preparation of SUMO-Fusion Proteins and Cyclic Peptides: SUMO is 12 kDa protein that expresses well in *E. coli* and stabilizes a variety of diverse fusion proteins. A β2-β3 loop peptide comprising the sequence L$^{41}$-to-F$^{59}$—or mutants thereof—was fused to a flexible GGS linker at the SUMO C-terminus, and RNA binding was measured by ELISA. A cyclized variant comprising the β2-β3 loop peptide was displayed on the surface of *E. coli* by fusion to the cell-surface protein OmpX by an intervening (GGS)$_3$ linker harboring a TEV protease site. Stapling was accomplished by inserting nucleophiles using L44C and F56C mutations. Following treatment with a reducing agent (DTT), chemical cyclization was achieved by SNAr conjugation using polyfluorinated biarylsulfoxide; β2-β3 loop peptides with R-to-A mutations were prepared similarly. RNA affinity was then measured by flow cytometry at 25° C. more than three times. The peptide product was subjected to TEV cleavage and the product was verified by mass spectrometry. *E. coli* displaying OmpX alone did not show appreciable TAR binding.

Molecular Dynamics (MD) Simulations: To evaluate the dynamics of the TBP6.7-TAR complex, a TAR-peptide complex comprising the β2-β3 loop, and isolated TAR RNA, we subjected the crystallographic coordinates, or subsets thereof, to MD using the Amber package.

TABLE 1

TBP6.7-TAR X-ray diffraction and refinement statistics

| Data Collection[a] | |
| --- | --- |
| Wavelength (Å) | 0.9795 |
| Space Group | P4$_3$2$_1$2 |
| Cell Constants | |
| a = b, c (Å) | 40.4, 284.6 |
| α = β = γ (°) | 90.0 |
| Resolution (Å) | 38.90-1.80 |
|  | (1.83-1.80) |
| R$_{p.i.m.}$ (%)[b] | 2.6 (45.1) |
| CC1/2 (%)[c] | 98.7 (69.2) |
| I/σ(I) | 19.9 (1.8) |
| Complete (%) | 99.4 (91.8) |
| Redundancy | 8.8 (7.9) |
| Refinement | |
| Resolution (Å) | 37.2-1.80 |
| No. reflections | 23297 |
| R$_{work}$/R$_{free}$ (%) | 18.5/21.0 |
| RMSD | |
| bonds (Å) | 0.014 |
| angles (°) | 1.60 |
| Clash Score[d] | 2.9 |
| Ramachandran (%) | |
| Allowed | 98.9 |
| Outliers | 1.1 |
| Coord. Error[d] (Å) | 0.19 |

[a]X-ray data collection was conducted remotely at the Stanford Synchrotron Radiation Lightsource (Menlo Park, CA) using Blu-Ice software and the Stanford Auto-Mounter.

[b]
$$R_{precision-indicting\ merging\ R-value} = \frac{\sum_{hkl} \sqrt{\frac{1}{N-1} \sum_{i=1}^{N} |I(hkl) - <I(hkl)>|}}{\sum_{hkl} \sum_{i=1}^{N} I(hkl)},$$

where N is the redundancy of the the data and </(hkl)> is the average intensity.
[c]The Pearson correlation coefficient calculated for the average intensities resulting from division of the unmerged data into two parts, each containing half of the measurements selected at random for each unique reflection.
[d]Coordinate error as implemented in PHENIX.

TABLE 2

Thermodynamic Parameters for TAR Binding by TBP6.7 at 20° C.

| Sample TBP | $K_D$ nM | n number sites | $\Delta H$ kcal mol$^{-1}$ | $-T\Delta S$ kcal mol$^{-1}$ | $\Delta G$ kcal mol$^{-1}$ | $\Delta\Delta G^{a,b}$ kcal mol$^{-1}$ | $K_{rel}$ |
|---|---|---|---|---|---|---|---|
| TBP6.7 | 2.5 ± 0.1 | 0.99 ± 0.02 | −25.0 ± 0.2 | 13.5 ± 0.2 | −11.6 ± 0.03 | n/a | |
| P46A | 11.7 ± 2.5 | 0.97 ± 0.05 | −22.7 ± 0.2 | 12.1 ± 0.1 | −10.6 ± 0.1 | 1.0 | |
| R47A | 1516 ± 163 | 0.96 ± 0.2 | −7.5 ± 1.1 | 0.3 ± 1.1 | −7.8 ± 0.1 | ~3.8$^c$ | |
| R47K | 156 | 1.01 | −11.0 | 1.9 | −9.1 | 2.5 | |
| Q48A | 5.5 ± 1.0 | 1.00 ± 0.01 | −22.6 ± 2.2 | 11.5 ± 2.1 | −11.1 ± 0.1 | 0.5 | |
| Q48T | 3.6 ± 1.9 | 1.00 ± 0.04 | −25.7 ± 0.1 | 14.4 ± 0.2 | −11.4 ± 0.3 | 0.2 | |
| R49A | 710 ± 205 | 0.91 ± 0.2 | −11.7 ± 3.2 | 3.4 ± 3.1 | −8.3 ± 0.2 | 3.3 | |
| T50A | 11.4 ± XX | 1.00 ± XX | −20.7 ± XX | 10.1 ± XX | −10.6 ± XX | 1. | |
| P51A | 10.8 ± 2.1 | 0.95 ± 0.05 | −23.1 ± 0.1 | 12.4 ± 0.0 | −10.7 ± 0.1 | 0.9 | |
| R52A | 290 ± 57 | 1.00 ± 0.01 | −14.3 ± 0.3 | 5.5 ± 0.2 | −8.8 ± 0.08 | 2.8 | |
| Q54A | 7.2 ± 2.4 | 1.05 ± 0.05 | −21.9 ± 2.0 | 10.9 ± 1.8 | −11.0 ± 0.2 | 0.6 | |
| ΔC | 12.0 ± 3.0 | 1.01 ± 0.01 | −24.7 ± 2.7 | 14.1 ± 2.5 | −10.6 ± 0.2 | 1.0 | |

$^a$The difference of [$\Delta G_{mutant} - \Delta G_{TBP6.7}$].
$^b$Defined as the ratio of [Mutant $K_{D,\,App}$]/[WT $K_{D,\,App}$] TBP6.7 at 20° C.
$^c$Considered an estimate due to the low c-value associated with the measurement.

Example 7

Pharmacological Properties of Cyclic Peptides

Toxicity of cyclic peptides that specifically bind to TAR are assessed in balb/c mice by a dose-escalation schema starting at an initial intravenous (tail vein) dose of 20 µg/mouse (~1 mg/kg) and increasing in an accelerated format until gross toxicity is observed or dosing is limited by other factors. Toxicity in groups of 3 treated mice are determined grossly by monitoring mouse weight in each treatment cohort a minimum of 3× weekly following a single dose. At sacrifice, heart, liver, colon, lung, spleen and kidney are collected for histopathologic evaluation by a board certified veterinary pathologist. All sections are scored based on overall percentage of tissue affected as well as degree of individual cellular alterations. A score of 1-4 can be assessed for <25%, 26-50%, 51-75%, and 75-100% tissue involvement, while a score of 1-3 can be assessed for mild, moderate, and marked cellular alterations. Cardiomyocyte changes assessed include: myocytic vacuolar degeneration, myocytolysis, myofibril atrophy, and fibrosis. Hepatocyte changes assessed include: hydropic and vacuolar degeneration. Tissues for toxicity assessment can be collected from animals 5 days post-dosing. Toxicity is assessed following a multiple-dosing protocol following pharmacokinetic (PK) evaluation and establishment of a presumed dosing schema (how much/how often) to test therapeutic efficacy. These multiple-dosing studies are done in cohorts of 5 mice using the PK calculated doses and schedule.

Serum stability is determined by incubation in mouse serum and determining levels over time by analytical methods (below). The PK of single-doses is carried out in balb/c mice using 3 doses determined to be safe based on toxicity (above). Cyclic peptides are administered intravenously (tail vein) and blood collected at 5, 15, 30, 60, 120, 240, 480, 720 and 1440 min by cardiac stick exsanguination under isoflurane anesthesia. Three mice are used per time point per dose and PK analysis is done using the combined animal data ("super-mouse" model). Peptide levels are measured based on amounts of administered cyclic peptide by LC/MS/MS with inclusion of stable isotope-labeled residues and control peptides in the assay protocol. All analytical methodology are validated in matrix (mouse plasma) with quality assurance (QA) and quality control (QC) samples included in each batch. PK data is analyzed by an appropriate modeling method (compartmental or non-compartmental) using Phoenix WinNonlin v.6.3 (Pharshight, St. Louis Mo.). The resulting PK data is used to determine a multiple dosing protocol for toxicity studies.

REFERENCES 1. https://grants.nih.gov/grants/guide/notice-files/NOT-OD-15-137.html.
2. Bannwarth, S. & Gatignol, A. HIV-1 TAR RNA: the target of molecular interactions between the virus and its host. *Curr HIV Res* 3, 61-71 (2005).
3. Puglisi, J. D., Tan, R., Calnan, B. J., Frankel, A. D. & Williamson, J. R. Conformation of the TAR RNA-arginine complex by NMR spectroscopy. *Science* 257, 76-80 (1992).
4. Aboul-ela, F., Karn, J. & Varani, G. Structure of HIV-1 TAR RNA in the absence of ligands reveals a novel conformation of the trinucleotide bulge. *Nucleic Acids Res* 24, 3974-3981 (1996).
5. Huthoff, H. & Berkhout, B. Mutations in the TAR hairpin affect the equilibrium between alternative conformations of the HIV-1 leader RNA. *Nucleic Acids Res* 29, 2594-2600 (2001).
6. Harrich, D., Ulich, C. & Gaynor, R. B. A critical role for the TAR element in promoting efficient human immunodeficiency virus type 1 reverse transcription. *J Virol* 70, 4017-4027 (1996).
Karn, J. & Stoltzfus, C. M. Transcriptional and posttranscriptional regulation of HIV-1 gene expression. *Cold Spring Harb Perspect Med* 2, a006916 (2012).
8. Ouellet, D. L., Plante, I., Landry, P., Barat, C., Janelle, M. E., Flamand, L., Tremblay, M. J. & Provost, P. Identification of functional microRNAs released through asymmetrical processing of HIV-1 TAR element. *Nucleic Acids Res* 36, 2353-2365 (2008).
9. Klase, Z., Winograd, R., Davis, J., Carpio, L., Hildreth, R., Heydarian, M., Fu, S., McCaffrey, T., Meiri, E., Ayash-Rashkovsky, M., Gilad, S., Bentwich, Z. & Kashanchi, F. HIV-1 TAR miRNA protects against apoptosis by altering cellular gene expression. *Retrovirology* 6, 18 (2009).
10. Klase, Z., Kale, P., Winograd, R., Gupta, M. V., Heydarian, M., Berro, R., McCaffrey, T. & Kashanchi, F. HIV-1 TAR element is processed by Dicer to yield a viral 10. micro-RNA involved in chromatin remodeling of the viral LTR. *BMC Mol Biol* 8, 63 (2007).
11. Oubridge, C., Ito, N., Evans, P. R., Teo, C. H. & Nagai, K. Crystal structure at 1.92 A resolution of the RNA-binding domain of the U1A spliceosomal protein complexed with an RNA hairpin. *Nature* 372, 432-438 (1994).
12. Crawford, D. W., Blakeley, B. D., Chen, P. H., Sherpa, C., Le Grice, S. F., Laird-Offringa, I. A. & McNaughton, B. R. An Evolved RNA Recognition Motif That Suppresses HIV-1 Tat/TAR-Dependent Transcription. *ACS Chem Biol* 11, 2206-2215 (2016).
13. Richter, S., Ping, Y. H. & Rana, T. M. TAR RNA loop: a scaffold for the assembly of a regulatory switch in HIV replication. *Proc Natl Acad Sci USA* 99, 7928-7933 (2002).
14. Hamy, F., Felder, E. R., Heizmann, G., Lazdins, J., Aboul-ela, F., Varani, G., Karn, J. & Klimkait, T. An inhibitor of the Tat/TAR RNA interaction that effectively suppresses HIV-1 replication. *Proc Natl Acad Sci USA* 94, 3548-3553 (1997).
15. Dingwall, C., Ernberg, I., Gait, M. J., Green, S. M., Heaphy, S., Karn, J., Lowe, A. D., Singh, M., Skinner, M. A. & Valerio, R. Human immunodeficiency virus 1 tat protein binds trans-activation-responsive region (TAR) RNA in vitro. *Proc Natl Acad Sci USA* 86, 6925-6929 (1989).
16. Dingwall, C., Ernberg, I., Gait, M. J., Green, S. M., Heaphy, S., Karn, J., Lowe, A. D., Singh, M. & Skinner, M. A. HIV-1 tat protein stimulates transcription by binding to a U-rich bulge in the stem of the TAR RNA structure. *EMBO J* 9, 4145-4153 (1990).
17. Roy, S., Delling, U., Chen, C. H., Rosen, C. A. & Sonenberg, N. A bulge structure in HIV-1 TAR RNA is required for Tat binding and Tat-mediated trans-activation. *Genes Dev* 4, 1365-1373 (1990).
18. Muesing, M. A., Smith, D. H. & Capon, D. J. Regulation of mRNA accumulation by a human immunodeficiency virus trans-activator protein. *Cell* 48, 691-701 (1987).
19. Jeang, K. T., Xiao, H. & Rich, E. A. Multifaceted activities of the HIV-1 transactivator of transcription, Tat. *J Biol Chem* 274, 28837-28840 (1999).
20. Toohey, M. G. & Jones, K. A. In vitro formation of short RNA polymerase II transcripts that terminate within the HIV-1 and HIV-2 promoter-proximal downstream regions. *Genes Dev* 3, 265-282 (1989).
21. Selby, M. J., Bain, E. S., Luciw, P. A. & Peterlin, B. M. Structure, sequence, and position of the stem-loop in tar determine transcriptional elongation by tat through the HIV-1 long terminal repeat. *Genes Dev* 3, 547-558 (1989).
22. Verhoef, K., Koper, M. & Berkhout, B. Determination of the minimal amount of Tat activity required for human immunodeficiency virus type 1 replication. *Virology* 237, 228-236 (1997).
23. Sampey, G. C., Saifuddin, M., Schwab, A., Barclay, R., Punya, S., Chung, M. C., Hakami, R. M., Zadeh, M. A., Lepene, B., Klase, Z. A., El-Hage, N., Young, M., Iordanskiy, S. & Kashanchi, F. Exosomes from HIV-1-infected Cells Stimulate Production of Pro-inflammatory Cytokines through Trans-activating Response (TAR) RNA. *J Biol Chem* 291, 1251-1266 (2016).
24. Richter, S., Parolin, C., Gatto, B., Del Vecchio, C., Brocca-Cofano, E., Fravolini, A., Palu, G. & Palumbo, M. Inhibition of human immunodeficiency virus type 1 tat-trans-activation-responsive region interaction by an antiviral quinolone derivative. *Antimicrob Agents Chemother* 48, 1895-1899 (2004).
25. Parolin, C., Gatto, B., Del Vecchio, C., Pecere, T., Tramontano, E., Cecchetti, V., Fravolini, A., Masiero, S., Palumbo, M. & Palu, G. New anti-human immunodeficiency virus type 1 6-aminoquinolones: mechanism of action. *Antimicrob Agents Chemother* 47, 889-896 (2003).
26. Lind, K. E., Du, Z., Fujinaga, K., Peterlin, B. M. & James, T. L. Structure-based computational database screening, in vitro assay, and NMR assessment of compounds that target TAR RNA. *Chem Biol* 9, 185-193 (2002).
27. Stelzer, A. C., Frank, A. T., Kratz, J. D., Swanson, M. D., Gonzalez-Hernandez, M. J., Lee, J., Andricioaei, I., Markovitz, D. M. & Al-Hashimi, H. M. Discovery of selective bioactive small molecules by targeting an RNA dynamic ensemble. *Nat Chem Biol* 7, 553-559 (2011).
28. Hamasaki, K. & Ueno, A. Aminoglycoside antibiotics, neamine and its derivatives as potent inhibitors for the RNA-protein interactions derived from HIV-1 activators. *Bioorg Med Chem Lett* 11, 591-594 (2001).
29. Cabrera, C., Gutierrez, A., Blanco, J., Barretina, J., Litovchick, A., Lapidot, A., Evdokimov, A. G., Clotet, B. & Este, J. A. Anti-human immunodeficiency virus activity of novel aminoglycoside-arginine conjugates at early stages of infection. *AIDS Res Hum Retroviruses* 16, 627-634 (2000).
30. Litovchick, A., Evdokimov, A. G. & Lapidot, A. Arginine-aminoglycoside conjugates that bind to HIV trans-activation responsive element RNA in vitro. *FEBS Lett* 445, 73-79 (1999).
31. Litovchick, A., Evdokimov, A. G. & Lapidot, A. Aminoglycoside-arginine conjugates that bind TAR RNA: synthesis, characterization, and antiviral activity. *Biochemistry* 39, 2838-2852 (2000).
32. Litovchick, A., Lapidot, A., Eisenstein, M., Kalinkovich, A. & Borkow, G. Neomycin B-arginine conjugate, a novel HIV-1 Tat antagonist: synthesis and anti-HIV activities. *Biochemistry* 40, 15612-15623 (2001).
33. Davidson, A., Leeper, T. C., Athanassiou, Z., Patora-Komisarska, K., Karn, J., Robinson, J. A. & Varani, G. Simultaneous recognition of HIV-1 TAR RNA bulge and loop sequences by cyclic peptide mimics of Tat protein. *Proc Natl Acad Sci USA* 106, 11931-11936 (2009).
34. Davidson, A., Patora-Komisarska, K., Robinson, J. A. & Varani, G. Essential structural requirements for specific recognition of HIV TAR RNA by peptide mimetics of Tat protein. *Nucleic Acids Res* 39, 248-256 (2011).
35. Lalonde, M. S., Lobritz, M. A., Ratcliff, A., Chamanian, M., Athanassiou, Z., Tyagi, M., Wong, J., Robinson, J. A., Karn, J., Varani, G. & Arts, E. J. Inhibition of both HIV-1 reverse transcription and gene expression by a cyclic peptide that binds the Tat-transactivating response element (TAR) RNA. *PLoS Pathog* 7, e1002038 (2011).
36. Mousseau, G. & Valente, S. Strategies to Block HIV Transcription: Focus on Small Molecule Tat Inhibitors. *Biology (Basel)* 1, 668-697 (2012).
37. Velagapudi, S. P., Cameron, M. D., Haga, C. L., Rosenberg, L. H., Lafitte, M., Duckett, D. R., Phinney, D. G. & Disney, M. D. Design of a small molecule against an oncogenic noncoding RNA. *Proc Natl Acad Sci USA* 113, 5898-5903 (2016).
38. Costales, M. G., Rzuczek, S. G. & Disney, M. D. Comparison of small molecules and oligonucleotides that target a toxic, non-coding RNA. *Bioorg Med Chem Lett* 26, 2605-2609 (2016).

39. Bernat, V. & Disney, M. D. RNA Structures as Mediators of Neurological Diseases and as Drug Targets. *Neuron* 87, 28-46 (2015).
40. Rzuczek, S. G., Gao, Y., Tang, Z. Z., Thornton, C. A., Kodadek, T. & Disney, M. D. Features of modularly assembled compounds that impart bioactivity against an RNA target. *ACS Chem Biol* 8, 2312-2321 (2013).
41. Disney, M. D. Rational design of chemical genetic probes of RNA function and lead therapeutics targeting repeating transcripts. *Drug Discov Today* 18, 1228-1236 (2013).
42. Velagapudi, S. P. & Disney, M. D. Defining RNA motif-aminoglycoside interactions via two-dimensional combinatorial screening and structure-activity relationships through sequencing. *Bioorg Med Chem* 21, 6132-6138 (2013).
43. Childs-Disney, J. L., Parkesh, R., Nakamori, M., Thornton, C. A. & Disney, M. D. Rational design of bioactive, modularly assembled aminoglycosides targeting the RNA that causes myotonic dystrophy type 1. *ACS Chem Biol* 7, 1984-1993 (2012).
44. Childs-Disney, J. L., Hoskins, J., Rzuczek, S. G., Thornton, C. A. & Disney, M. D. Rationally designed small molecules targeting the RNA that causes myotonic dystrophy type 1 are potently bioactive. *ACS Chem Biol* 7, 856-862 (2012).
45. Childs-Disney, J. L., Tsitovich, P. B. & Disney, M. D. Using modularly assembled ligands to bind RNA internal loops separated by different distances. *Chembiochem* 12, 2143-2146 (2011).
46. Pushechnikov, A., Lee, M. M., Childs-Disney, J. L., Sobczak, K., French, J. M., Thornton, C. A. & Disney, M. D. Rational design of ligands targeting triplet repeating transcripts that cause RNA dominant disease: application to myotonic muscular dystrophy type 1 and spinocerebellar ataxia type 3. *J Am Chem Soc* 131, 9767-9779 (2009).
47. Lee, M. M., Pushechnikov, A. & Disney, M. D. Rational and modular design of potent ligands targeting the RNA that causes myotonic dystrophy 2. *ACS Chem Biol* 4, 345-355 (2009).
48. Blakeley, B. D. & McNaughton, B. R. Synthetic RNA recognition motifs that selectively recognize HIV-1 trans-activation response element hairpin RNA. *ACS Chem Biol* 9, 1320-1329 (2014).
49. Churcher, M. J., Lamont, C., Hamy, F., Dingwall, C., Green, S. M., Lowe, A. D., Butler, J. G., Gait, M. J. & Karn, J. High affinity binding of TAR RNA by the human immunodeficiency virus type-1 tat protein requires base-pairs in the RNA stem and amino acid residues flanking the basic region. *J Mol Biol* 230, 90-110 (1993).
50. Delling, U., Reid, L. S., Barnett, R. W., Ma, M. Y., Climie, S., Sumner-Smith, M. & Sonenberg, N. Conserved nucleotides in the TAR RNA stem of human immunodeficiency virus type 1 are critical for Tat binding and trans activation: model for TAR RNA tertiary structure. *J Virol* 66, 3018-3025 (1992).
51. Weeks, K. M. & Crothers, D. M. RNA recognition by Tat-derived peptides: interaction in the major groove? *Cell* 66, 577-588 (1991).
52. Calnan, B. J., Tidor, B., Biancalana, S., Hudson, D. & Frankel, A. D. Arginine-mediated RNA recognition: the arginine fork. *Science* 252, 1167-1171 (1991).
53. Hamy, F., Asseline, U., Grasby, J., Iwai, S., Pritchard, C., Slim, G., Butler, P. J., Karn, J. & Gait, M. J. Hydrogen-bonding contacts in the major groove are required for human immunodeficiency virus-1 tat protein recognition of TAR RNA. *J Mol Biol* 230, 111-123 (1993).
54. Pritchard, C. E., Grasby, J. A., Hamy, F., Zacharek, A. M., Singh, M., Karn, J. & Gait, M. J. Methylphosphonate mapping of phosphate contacts critical for RNA recognition by the human immunodeficiency virus tat and rev proteins. *Nucleic Acids Res* 22, 2592-2600 (1994).
55. Tao, J. & Frankel, A. D. Specific binding of arginine to TAR RNA. *Proc Natl Acad Sci USA* 89, 2723-2726 (1992).
56. Sumner-Smith, M., Roy, S., Barnett, R., Reid, L. S., Kuperman, R., Delling, U. & Sonenberg, N. Critical chemical features in trans-acting-responsive RNA are required for interaction with human immunodeficiency virus type 1 Tat protein. *J Virol* 65, 5196-5202 (1991).
57. Aboul-ela, F., Karn, J. & Varani, G. The structure of the human immunodeficiency virus type-1 TAR RNA reveals principles of RNA recognition by Tat protein. *J Mol Biol* 253, 313-332 (1995).
58. Borkar, A. N., Bardaro, M. F., Jr., Camilloni, C., Aprile, F. A., Varani, G. & Vendruscolo, M. Structure of a low-population binding intermediate in protein-RNA recognition. *Proc Natl Acad Sci USA* 113, 7171-7176 (2016).
59. Fu, A., Tang, R., Hardie, J., Farkas, M. E. & Rotello, V. M. Promises and pitfalls of intracellular delivery of proteins. *Bioconjug Chem* 25, 1602-1608 (2014).
60. Frokjaer, S. & Otzen, D. E. Protein drug stability: a formulation challenge. *Nat Rev Drug Discov* 4, 298-306 (2005).
61. Patel, I. H., Zhang, X., Nieforth, K., Salgo, M. & Buss, N. Pharmacokinetics, pharmacodynamics and drug interaction potential of enfuvirtide. *Clin Pharmacokinet* 44, 175-186 (2005).
62. Fosgerau, K. & Hoffmann, T. Peptide therapeutics: current status and future directions. *Drug Discov Today* 20, 122-128 (2015).
63. Howell, S. M., Fiacco, S. V., Takahashi, T. T., Jalali-Yazdi, F., Millward, S. W., Hu, B., Wang, P. & Roberts, R. W. Serum stable natural peptides designed by mRNA display. *Sci Rep* 4, 6008 (2014).
64. Adessi, C., Frossard, M. J., Boissard, C., Fraga, S., Bieler, S., Ruckle, T., Vilbois, F., Robinson, S. M., Mutter, M., Banks, W. A. & Soto, C. Pharmacological profiles of peptide drug candidates for the treatment of Alzheimer's disease. *J Biol Chem* 278, 13905-13911 (2003).
65. Bockus, A. T., McEwen, C. M. & Lokey, R. S. Form and function in cyclic peptide natural products: a pharmacokinetic perspective. *Curr Top Med Chem* 13, 821-836 (2013).
66. Sieber, S. A. & Marahiel, M. A. Learning from nature's drug factories: nonribosomal synthesis of macrocyclic peptides. *J Bacteriol* 185, 7036-7043 (2003).
67. Watanabe, K., Hotta, K., Praseuth, A. P., Koketsu, K., Migita, A., Boddy, C. N., Wang, C. C., Oguri, H. & Oikawa, H. Total biosynthesis of antitumor nonribosomal peptides in *Escherichia coli*. *Nat Chem Biol* 2, 423-428 (2006).
68. Blakeley, B. D., Shattuck, J., Coates, M. B., Tran, E., Laird-Offringa, I. A. & McNaughton, B. R. Analysis of protein-RNA complexes involving a RNA recognition motif engineered to bind hairpins with seven- and eight-nucleotide loops. *Biochemistry* 52, 4745-4747 (2013).
69. Chapman, A. M. & McNaughton, B. R. Scratching the Surface: Resurfacing Proteins to Endow New Properties and Function. *Cell Chem Biol* 23, 543-553 (2016).
70. Bruce, V. J., Lopez-Islas, M. & McNaughton, B. R. Resurfaced cell-penetrating nanobodies: A potentially general scaffold for intracellularly targeted protein discovery. *Protein Sci* 25, 1129-1137 (2016).

71. Gray, M. A., Tao, R. N., DePorter, S. M., Spiegel, D. A. & McNaughton, B. R. A Nanobody Activation Immunotherapeutic that Selectively Destroys HER2-Positive Breast Cancer Cells. *Chembiochem* 17, 155-158 (2016).
72. Chapman, A. M. & McNaughton, B. R. Synthetic Proteins Potently and Selectively Bind the Oncoprotein Gankyrin, Modulate Its Interaction with S6 ATPase, and Suppress Gankyrin/MDM2-Dependent Ubiquitination of p53. *ACS Chem Biol* 10, 1880-1886 (2015).
73. Walker, S. N., Tennyson, R. L., Chapman, A. M., Kennan, A. J. & McNaughton, B. R. GLUE that sticks to HIV: a helix-grafted GLUE protein that selectively binds the HIV gp41 N-terminal helical region. *Chembiochem* 16, 219-222 (2015).
74. Chapman, A. M. & McNaughton, B. R. Resurfaced shape complementary proteins that selectively bind the oncoprotein gankyrin. *ACS Chem Biol* 9, 2223-2228 (2014).
75. McNaughton, B. R. & Miller, B. L. Resin-bound dynamic combinatorial chemistry. *Org Lett* 8, 1803-1806 (2006).
76. McNaughton, B. R., Gareiss, P. C. & Miller, B. L. Identification of a selective small-molecule ligand for HIV-1 frameshift-inducing stem-loop RNA from an 11,325 member resin bound dynamic combinatorial library. *J Am Chem Soc* 129, 11306-11307 (2007).
77. Gareiss, P. C., Sobczak, K., McNaughton, B. R., Palde, P. B., Thornton, C. A. & Miller, B. L. Dynamic combinatorial selection of molecules capable of inhibiting the (CUG) repeat RNA-MBNL1 interaction in vitro: discovery of lead compounds targeting myotonic dystrophy (DM1). *J Am Chem Soc* 130, 16254-16261 (2008).
78. McNaughton, B. R., Cronican, J. J., Thompson, D. B. & Liu, D. R. Mammalian cell penetration, siRNA transfection, and DNA transfection by supercharged proteins. *Proc Natl Acad Sci USA* 106, 6111-6116 (2009).
79. Cronican, J. J., Thompson, D. B., Beier, K. T., McNaughton, B. R., Cepko, C. L. & Liu, D. R. Potent delivery of functional proteins into Mammalian cells in vitro and in vivo using a supercharged protein. *ACS Chem Biol* 5, 747-752 (2010).
80. DePorter, S. M., Lui, I., Mohan, U. & McNaughton, B. R. A protein transduction domain with cell uptake and selectivity profiles that are controlled by multivalency effects. *Chem Biol* 20, 434-444 (2013).
81. DePorter, S. M., Lui, I., Bruce, V. J., Gray, M. A., Lopez-Islas, M. & McNaughton, B. R. Mutagenesis modulates the uptake efficiency, cell-selectivity, and functional enzyme delivery of a protein transduction domain. *Mol Biosyst* 10, 18-23 (2014).
82. DePorter, S. M. & McNaughton, B. R. Engineered M13 bacteriophage nanocarriers for intracellular delivery of exogenous proteins to human prostate cancer cells. *Bioconjug Chem* 25, 1620-1625 (2014).
83. Jenkins, J. L., Krucinska, J., McCarty, R. M., Bandarian, V. & Wedekind, J. E. Comparison of a preQ1 riboswitch aptamer in metabolite-bound and free states with implications for gene regulation. *J Biol Chem* 286, 24626-24637 (2011).
84. Liberman, J. A., Suddala, K. C., Aytenfisu, A., Chan, D., Belashov, I. A., Salim, M., Mathews, D. H., Spitale, R. C., Walter, N. G. & Wedekind, J. E. Structural analysis of a class III preQ1 riboswitch reveals an aptamer distant from a ribosome-binding site regulated by fast dynamics. *Proc Natl Acad Sci USA* 112, E3485-3494 (2015).
85. Spitale, R. C., Torelli, A. T., Krucinska, J., Bandarian, V. & Wedekind, J. E. The structural basis for recognition of the PreQ0 metabolite by an unusually small riboswitch aptamer domain. *J Biol Chem* 284, 11012-11016 (2009).
86. Suddala, K. C., Rinaldi, A. J., Feng, J., Mustoe, A. M., Eichhorn, C. D., Liberman, J. A., Wedekind, J. E., Al-Hashimi, H. M., Brooks, C. L., 3rd & Walter, N. G. Single transcriptional and translational preQ1 riboswitches adopt similar pre-folded ensembles that follow distinct folding pathways into the same ligand-bound structure. *Nucleic Acids Res* 41, 10462-10475 (2013).
87. Jamburuthugoda, V. K., Guo, D., Wedekind, J. E. & Kim, B. Kinetic evidence for interaction of human immunodeficiency virus type 1 reverse transcriptase with the 3'-OH of the incoming dTTP substrate. *Biochemistry* 44, 10635-10643 (2005).
88. Jamburuthugoda, V. K., Santos-Velazquez, J. M., Skasko, M., Operario, D. J., Purohit, V., Chugh, P., Szymanski, E. A., Wedekind, J. E., Bambara, R. A. & Kim, B. Reduced dNTP binding affinity of 3TC-resistant M184I HIV-1 reverse transcriptase variants responsible for viral infection failure in macrophage. *J Biol Chem* 283, 9206-9216 (2008).
89. Lippa, G. M. in Biochemistry and Biophysics, Vol. Ph.D. 240 (University of Rochester School of Medicine and Dentistry, 2013).
90. Lippa, G. M., Liberman, J. A., Jenkins, J. L., Krucinska, J., Salim, M. & Wedekind, J. E. Crystallographic analysis of small ribozymes and riboswitches. *Methods Mol Biol* 848, 159-184 (2012).
91. Wedekind, J. E., Gillilan, R., Janda, A., Krucinska, J., Salter, J. D., Bennett, R. P., Raina, J. & Smith, H. C. Nanostructures of APOBEC3G support a hierarchical assembly model of high molecular mass ribonucleoprotein particles from dimeric subunits. *J Biol Chem* 281, 38122-38126 (2006).
92. Xie, K., Sowden, M. P., Dance, G. S., Torelli, A. T., Smith, H. C. & Wedekind, J. E. The structure of a yeast RNA-editing deaminase provides insight into the fold and function of activation-induced deaminase and APOBEC-1. *Proc Natl Acad Sci USA* 101, 8114-8119 (2004).
93. Bennett, R. P., Salter, J. D., Liu, X., Wedekind, J. E. & Smith, H. C. APOBEC3G subunits self-associate via the C-terminal deaminase domain. *J Biol Chem* 283, 33329-33336 (2008).
94. Wang, W., Maucuer, A., Gupta, A., Manceau, V., Thickman, K. R., Bauer, W. J., Kennedy, S. D., Wedekind, J. E., Green, M. R. & Kielkopf, C. L. Structure of phosphorylated SF1 bound to U2AF(6)(5) in an essential splicing factor complex. *Structure* 21, 197-208 (2013).
95. Dutton, G. HIV Researchers Seek a Potential Cure. *Genetic Engineering & Biotechnology News* 33, 4997 (2013).
96. Majmudar, N. OyaGen blazing path toward anti-AIDS drug. *Rochester Democrat and Chronicle*, D106 (2005).
97. Salter, J. D., Morales, G. A. & Smith, H. C. Structural insights for HIV-1 therapeutic strategies targeting Vif. *Trends Biochem Sci* 39, 373-380 (2014).
98. Pilon, J. L., Clausen, D. J., Hansen, R. J., Lunghofer, P. J., Charles, B., Rose, B. J., Thamm, D. H., Gustafson, D. L., Bradner, J. E. & Williams, R. M. Comparative pharmacokinetic properties and antitumor activity of the marine HDACi Largazole and Largazole peptide isostere. *Cancer Chemother Pharmacol* 75, 671-682 (2015).
99. Paoloni, M. C., Mazcko, C., Fox, E., Fan, T., Lana, S., Kisseberth, W., Vail, D. M., Nuckolls, K., Osborne, T., Yalkowsy, S., Gustafson, D., Yu, Y., Cao, L. & Khanna, C. Rapamycin pharmacokinetic and pharmacodynamic rela- 100. Hudachek, S. F. & Gustafson, D. L. Physiologically based pharmacokinetic model of lapatinib developed in mice and scaled to humans. *J Pharmacokinet Pharmacodyn* 40, 157-176 (2013).
101. Thomas, R. S., Conolly, R. B., Gustafson, D. L., Long, M. E., Benjamin, S. A. & Yang, R. S. A physiologically based pharmacodynamic analysis of hepatic foci within a medium-term liver bioassay using pentachlorobenzene as a promoter and diethylnitrosamine as an initiator. *Toxicol Appl Pharmacol* 166, 128-137 (2000).
102. Puglisi, J. D., Chen, L., Blanchard, S. & Frankel, A. D. Solution structure of a bovine immunodeficiency virus Tat-TAR peptide-RNA complex. *Science* 270, 1200-1203 (1995).
103. Wilkinson, K. A., Merino, E. J. & Weeks, K. M. Selective 2'-hydroxyl acylation analyzed by primer extension (SHAPE): quantitative RNA structure analysis at single nucleotide resolution. *Nat Protoc* 1, 1610-1616 (2006).
104. Berkhout, B. & van Wamel, J. L. The leader of the HIV-1 RNA genome forms a compactly folded tertiary structure. *RNA* 6, 282-295 (2000).
105. Clever, J., Sassetti, C. & Parslow, T. G. RNA secondary structure and binding sites for gag gene products in the 5' packaging signal of human immunodeficiency virus type 1. *J Virol* 69, 2101-2109 (1995).
106. Keane, S. C., Heng, X., Lu, K., Kharytonchyk, S., Ramakrishnan, V., Carter, G., Barton, S., Hosic, A., Florwick, A., Santos, J., Bolden, N. C., McCowin, S., Case, D. A., Johnson, B. A., Salemi, M., Telesnitsky, A. & Summers, M. F. RNA structure. Structure of the HIV-1 RNA packaging signal. *Science* 348, 917-921 (2015).
107. Olsen, G. L., Edwards, T. E., Deka, P., Varani, G., Sigurdsson, S. T. & Drobny, G. P. Monitoring tat peptide binding to TAR RNA by solid-state 31P-19F REDOR NMR. *Nucleic Acids Res* 33, 3447-3454 (2005).
108. Bandziulis, R. J., Swanson, M. S. & Dreyfuss, G. RNA-binding proteins as developmental regulators. *Genes Dev* 3, 431-437 (1989).
109. Query, C. C., Bentley, R. C. & Keene, J. D. A common RNA recognition motif identified within a defined U1 RNA binding domain of the 70K U1 snRNP protein. *Cell* 57, 89-101 (1989).
110. Critchley, A. D., Haneef, I., Cousens, D. J. & Stockley, P. G. Modeling and solution structure probing of the HIV-1 TAR stem-loop. *J Mol Graph* 11, 92-97, 124 (1993).
111. Kulinski, T., Olejniczak, M., Huthoff, H., Bielecki, L., Pachulska-Wieczorek, K., Das, A. T., Berkhout, B. & Adam iak, R. W. The apical loop of the HIV-1 TAR RNA hairpin is stabilized by a cross-loop base pair. *J Biol Chem* 278, 38892-38901 (2003).
112. Richter, S., Cao, H. & Rana, T. M. Specific HIV-1 TAR RNA loop sequence and functional groups are required for human cyclin T1-Tat-TAR ternary complex formation. *Biochemistry* 41, 6391-6397 (2002).
113. Liberman, J. A., Bogue, J. T., Jenkins, J. L., Salim, M. & Wedekind, J. E. ITC analysis of ligand binding to preQ(1) riboswitches. *Methods Enzymol* 549, 435-450 (2014).
114. Hay, R. T. SUMO: a history of modification. *Mol Cell* 18, 1-12 (2005).
115. Wedekind, J. E. & McKay, D. B. Purification, crystallization, and X-ray diffraction analysis of small ribozymes. *Methods Enzymol* 317, 149-168 (2000).
116. Liberman, J. A., Salim, M., Krucinska, J. & Wedekind, J. E. Structure of a class II preQ1 riboswitch reveals ligand recognition by a new fold. *Nat Chem Biol* 9, 353-355 (2013).
117. Myszka, D. G. Kinetic analysis of macromolecular interactions using surface plasmon resonance biosensors. *Curr Opin Biotechnol* 8, 50-57 (1997).
118. Rupert, P. B., Xiao, H. & Ferre-D'Amare, A. R. U1A RNA-binding domain at 1.8 A resolution. *Acta Crystallogr D Biol Crystallogr* 59, 1521-1524 (2003).
119. McPherson, A. Introduction to protein crystallization. *Methods* 34, 254-265 (2004).
120. Doudna, J. A., Grosshans, C., Gooding, A. & Kundrot, C. E. Crystallization of ribozymes and small RNA motifs by a sparse matrix approach. *Proc Natl Acad Sci USA* 90, 7829-7833 (1993).
121. Gilliland, G. L., Tung, M., Blakeslee, D. M. & Ladner, J. E. Biological Macromolecule Crystallization Database, Version 3.0: new features, data and the NASA archive for protein crystal growth data. *Acta Crystallogr D Biol Crystallogr* 50, 408-413 (1994).
122. Ke, A. & Doudna, J. A. Crystallization of RNA and RNA-protein complexes. *Methods* 34, 408-414 (2004).
123. Scott, W. G., Finch, J. T., Grenfell, R., Fogg, J., Smith, T., Gait, M. J. & Klug, A. Rapid crystallization of chemically synthesized hammerhead RNAs using a double screening procedure. *J Mol Biol* 250, 327-332 (1995).
124. Kraft, P., Bergamaschi, A., Broennimann, C., Dinapoli, R., Eikenberry, E. F., Henrich, B., Johnson, I., Mozzanica, A., Schleputz, C. M., Willmott, P. R. & Schmitt, B. Performance of single-photon-counting PILATUS detector modules. *J Synchrotron Radiat* 16, 368-375 (2009).
125. Kabsch, W. Xds. *Acta Crystallogr D Biol Crystallogr* 66, 125-132 (2010).
126. Mueller, M., Wang, M. & Schulze-Briese, C. Optimal fine phi-slicing for single-photon-counting pixel detectors. *Acta Crystallogr D Biol Crystallogr* 68, 42-56 (2012).
127. Pflugrath, J. W. The finer things in X-ray diffraction data collection. *Acta Crystallogr D Biol Crystallogr* 55, 1718-1725 (1999).
128. Gonzalez, A., Moorhead, P., McPhillips, S. E., Song, J., Sharp, K., Taylor, J. R., Adams, P. D., Sauter, N. K. & Soltis, S. M. Web-Ice: integrated data collection and analysis for macromolecular crystallography. *Journal of Applied Crystallography* 41, 176-184 (2008).
129. Murray, J. W., Garman, E. F. & Ravelli, R. B. G. X-ray absorption by macromolecular crystals: the effects of wavelength and crystal composition on absorbed dose. *Journal of Applied Crystallography* 37, 513-522 (2004).
130. McCoy, A. J., Grosse-Kunstleve, R. W., Adams, P. D., Winn, M. D., Storoni, L. C. & Read, R. J. Phaser crystallographic software. *J Appl Crystallogr* 40, 658-674 (2007).
131. Wedekind, J. E., Frey, P. A. & Rayment, I. Three-dimensional structure of galactose-1-phosphate uridylyltransferase from *Escherichia coli* at 1.8 A resolution. *Biochemistry* 34, 11049-11061 (1995).
132. Wedekind, J. E. & McKay, D. B. Crystal structure of a lead-dependent ribozyme revealing metal binding sites relevant to catalysis. *Nat Struct Biol* 6, 261-268 (1999).
133. Goodman, J. L., Wang, S., Alam, S., Ruzicka, F. J., Frey, P. A. & Wedekind, J. E. Ornithine cyclodeaminase: structure, mechanism of action, and implications for the mu-crystallin family. *Biochemistry* 43, 13883-13891 (2004).

134. Ferre-D'Amare, A. R. Use of the spliceosomal protein U1A to facilitate crystallization and structure determination of complex RNAs. *Methods* 52, 159-167 (2010).
135. Bruno, B. J., Miller, G. D. & Lim, C. S. Basics and recent advances in peptide and protein drug delivery. *Ther Deliv* 4, 1443-1467 (2013).
136. Amblard, M., Fehrentz, J. A., Martinez, J. & Subra, G. Methods and protocols of modern solid phase Peptide synthesis. *Mol Biotechnol* 33, 239-254 (2006).
137. Palomo, J. M. Solid-phase peptide synthesis: an overview focused on the preparation of biologically relevant peptides. *Rsc Advances* 4, 32658-32672 (2014).
138. Chatterjee, J., Laufer, B. & Kessler, H. Synthesis of N-methylated cyclic peptides. *Nature Protocols* 7, 432-444 (2012).
139. Mishra, J. K., Zhang, C., Spokoyny, A. M., Pentelute, B. L. & Snyder, S. E. A Perfluoroaryl-Cysteine SNAr Chemistry Approach towards F-18 labeling of Bioactive Peptides. *Journal of Labelled Compounds & Radiopharmaceuticals* 58, S265-S265 (2015).
140. Spokoyny, A. M., Zou, Y. K., Ling, J. J., Yu, H. T., Lin, Y. S. & Pentelute, B. L. A Perfluoroaryl-Cysteine SNAr Chemistry Approach to Unprotected Peptide Stapling. *Journal of the American Chemical Society* 135, 5946-5949 (2013).
141. Rink, R., Arkema-Meter, A., Baudoin, I., Post, E., Kuipers, A., Nelemans, S. A., Akanbi, M. H. & Moll, G. N. To protect peptide pharmaceuticals against peptidases. *J Pharmacol Toxicol Methods* 61, 210-218 (2010).
142. Chapman, A. M., Rogers, B. E. & McNaughton, B. R. Characterization of the binding interaction between the oncoprotein gankyrin and a grafted S6 ATPase. *Biochemistry* 53, 6857-6859 (2014).
143. Bird, G. H., Mazzola, E., Opoku-Nsiah, K., Lammert, M. A., Godes, M., Neuberg, D. S. & Walensky, L. D. Biophysical determinants for cellular uptake of hydrocarbon-stapled peptide helices. *Nat Chem Biol* (2016).
144. Maianti, J. P., McFedries, A., Foda, Z. H., Kleiner, R. E., Du, X. Q., Leissring, M. A., Tang, W. J., Charron, M. J., Seeliger, M. A., Saghatelian, A. & Liu, D. R. Antidiabetic activity of insulin-degrading enzyme inhibitors mediated by multiple hormones. *Nature* 511, 94-98 (2014).
145. Hilimire, T. A., Bennett, R. P., Stewart, R. A., Garcia-Miranda, P., Blume, A., Becker, J., Sherer, N., Helms, E. D., Butcher, S. E., Smith, H. C. & Miller, B. L. N-Methylation as a Strategy for Enhancing the Affinity and Selectivity of RNA-binding Peptides: Application to the HIV-1 Frameshift-Stimulating RNA. *ACS Chem Biol* 11, 88-94 (2016).
146. Qian, Z., Liu, T., Liu, Y. Y., Briesewitz, R., Barrios, A. M., Jhiang, S. M. & Pei, D. Efficient delivery of cyclic peptides into mammalian cells with short sequence motifs. *ACS Chem Biol* 8, 423-431 (2013).
147. Oh, D., Sun, J., Nasrolahi Shirazi, A., LaPlante, K. L., Rowley, D. C. & Parang, K. Antibacterial activities of amphiphilic cyclic cell-penetrating peptides against multidrug-resistant pathogens. *Mol Pharm* 11, 3528-3536 (2014).
148. Yang, J., Tsutsumi, H., Furuta, T., Sakurai, M. & Mihara, H. Interaction of amphiphilic alpha-helical cell-penetrating peptides with heparan sulfate. *Org Biomol Chem* 12, 4673-4681 (2014).
149. Sardan, M., Kilinc, M., Genc, R., Tekinay, A. B. & Guler, M. O. Cell penetrating peptide amphiphile integrated liposomal systems for enhanced delivery of anticancer drugs to tumor cells. *Faraday Discuss* 166, 269-283 (2013).
150. Eiriksdottir, E., Konate, K., Langel, U., Divita, G. & Deshayes, S. Secondary structure of cell-penetrating peptides controls membrane interaction and insertion. *Biochim Biophys Acta* 1798, 1119-1128 (2010).
151. Liao, X. L., Rabideau, A. E. & Pentelute, B. L. Delivery of Antibody Mimics into Mammalian Cells via Anthrax Toxin Protective Antigen. *Chembiochem* 15, 2458-2466 (2014).
152. Alam, S., Grum-Tokars, V., Krucinska, J., Kundracik, M. L. & Wedekind, J. E. Conformational heterogeneity at position U37 of an all-RNA hairpin ribozyme with implications for metal binding and the catalytic structure of the S-turn. *Biochemistry* 44, 14396-14408 (2005).
153. Salter, J., Krucinska, J., Alam, S., Grum-Tokars, V. & Wedekind, J. E. Water in the active site of an all-RNA hairpin ribozyme and effects of Gua8 base variants on the geometry of phosphoryl transfer. *Biochemistry* 45, 686-700 (2006).
154. Wedekind, J. E. & McKay, D. B. Crystal structure of the leadzyme at 1.8 A resolution: metal ion binding and the implications for catalytic mechanism and allo site ion regulation. *Biochemistry* 42, 9554-9563 (2003).
155. Li, M., Tao, Y., Shu, Y. L., LaRochelle, J. R., Steinauer, A., Thompson, D., Schepartz, A., Chen, Z. Y. & Liu, D. R. Discovery and Characterization of a Peptide That Enhances Endosomal Escape of Delivered Proteins in Vitro and in Vivo. *Journal of the American Chemical Society* 137, 14084-14093 (2015).
156. Platt, E. J., Wehrly, K., Kuhmann, S. E., Chesebro, B. & Kabat, D. Effects of CCR5 and CD4 cell surface concentrations on infections by macrophagetropic isolates of human immunodeficiency virus type 1. *J Virol* 72, 2855-2864 (1998).
157. Shan, L., Rabi, S. A., Laird, G. M., Eisele, E. E., Zhang, H., Margolick, J. B. & Siliciano, R. F. A novel PCR assay for quantification of HIV-1 RNA. *J Virol* 87, 6521-6525 (2013).

What is claimed is:

1. An isolated peptide comprising an amino acid sequence, the amino acid sequence consisting of the amino acid sequence of SEQ ID NO: 2, wherein the isolated peptide specifically binds to HIV-1 trans-activation responsive element.

2. The isolated peptide of claim 1, the amino acid sequence consisting of the amino acid sequence of SEQ ID NO: 3.

3. The isolated peptide of claim 2, the amino acid sequence consisting of the amino acid sequence of SEQ ID NO: 4.

4. The isolated peptide of claim 1, the amino acid sequence consisting of 13 amino acid residues at position 4 to position 16 of the amino acid sequence selected from the group consisting of SEQ ID NOs: 8-9 and SEQ ID NOs: 12-22.

5. The isolated peptide of claim 1, wherein the peptide is a cyclic peptide.

6. The cyclic peptide of claim 5, wherein the cyclic peptide is a head-to-tail cyclization, a side chain-to-side chain cyclization, a head-to-side chain cyclization, or a side chain-to-tail cyclization.

7. The cyclic peptide of claim 5, wherein the cyclic peptide is a side chain-to-side chain cyclization and the side chains of the amino acids at positions 1 and 13 are conjugated to form the cyclic peptide.

8. The cyclic peptide of claim 7, wherein the amino acids at positions 1 and 13 are cysteines.

9. An isolated peptide comprising an amino acid sequence, the amino acid sequence consisting of the amino acid sequence selected from the group consisting of SEQ ID NOs: 5-24 wherein the isolated peptide specifically binds to HIV-1 trans-activation responsive element.

10. The isolated peptide of claim 9 consisting of the amino acid sequence of SEQ ID NO: 6.

11. The isolated peptide of claim 10 consisting of the amino acid sequence of SEQ ID NO: 7.

12. The isolated peptide of claim 9 consisting of the amino acid sequence selected from the group consisting of SEQ ID NOs: 8-24.

13. The isolated peptide of claim 9, wherein the peptide is a cyclic peptide.

14. The cyclic peptide of claim 13, wherein the cyclic peptide is a head-to-tail cyclization, a side chain-to- side chain cyclization, a head-to-side chain cyclization, or a side chain-to-tail cyclization.

15. The cyclic peptide of claim 13, wherein the cyclic peptide is a side chain-to-side chain cyclization and the side chains of the amino acids at positions 2 and 18, or the amino acids at positions 4 and 16, are conjugated to form the cyclic peptide.

16. The cyclic peptide of claim 15, wherein the amino acids at positions 2 and 18 of SEQ ID NO: 5, or the amino acids at positions 4 and 16 of SEQ ID NO: 5, are cysteines.

17. A cyclic peptide comprising an amino acid sequence, the amino acid sequence comprising the 13 amino acid residues at position 4 to position 16 of one of SEQ ID NOs: 7-24.

18. The cyclic peptide of claim 17, wherein the 13 amino acid sequence comprises residues at position 4 to position 16 of SEQ ID NO: 15.

19. The cyclic peptide of claim 17, wherein the 13 amino acid sequence comprises residues at position 4 to position 16 of one of SEQ ID NOs: 8-24.

20. The cyclic peptide of claim 17, wherein the cyclic peptide specifically binds to HIV-1 trans-activation responsive element.

21. The cyclic peptide of claim 17, wherein the cyclic peptide is a head-to-tail cyclization, a side chain-to-side chain cyclization, a head-to-side chain cyclization, or a side chain-to-tail cyclization.

22. The cyclic peptide of claim 17, wherein the cyclic peptide is a side chain-to-side chain cyclization and the side chains of the amino acids at positions 4 and 16 of SEQ ID NO: 7-24 are conjugated to form the cyclic peptide.

23. The cyclic peptide of claim 22, wherein the amino acids at positions 4 and 16 of SEQ ID NO: 7 are cysteines.

24. A cyclic peptide comprising an amino acid sequence, the amino acid sequence comprising the amino acid sequence of one or SEQ ID NOs: 5-24.

25. The cyclic peptide of claim 24 comprising the amino acid sequence of SEQ ID NO: 6.

26. The cyclic peptide of claim 25 comprising the amino acid sequence of SEQ ID NO: 7.

27. The cyclic peptide of claim 24, wherein the amino acid sequence is one of SEQ ID NOs: 8-24.

28. The cyclic peptide of claim 24, wherein the cyclic peptide specifically binds to HIV-1 trans-activation responsive element.

29. The cyclic peptide of claim 24, wherein the cyclic peptide is a head-to-tail cyclization, a side chain-to-side chain cyclization, a head-to-side chain cyclization, or a side chain-to-tail cyclization.

30. The cyclic peptide of claim 24, wherein the cyclic peptide is a side chain-to-side chain cyclization and the side chains of the amino acids at positions 2 and 18 of SEQ ID NO: 5, or the amino acids at positions 4 and 16 of SEQ ID NO: 5, are conjugated to form the cyclic peptide.

31. The cyclic peptide of claim 30, wherein the amino acids at positions 2 and 18, or the amino acids at positions 4 and 16, are cysteines.

32. A pharmaceutical composition comprising the peptide of claim 1.

33. A method of inhibiting the interaction between HIV Tat and HIV TAR, the method comprising contacting an HIV infected cell with the peptide of claim 1.

34. A method of reducing HIV proliferation, the method comprising contacting an HIV infected cell with the peptide of claim 1.

* * * * *

UNITED STATES PATENT AND TRADEMARK OFFICE
CERTIFICATE OF CORRECTION

Page 1 of 1

PATENT NO.       : 10,538,556 B2
APPLICATION NO.  : 15/805933
DATED            : January 21, 2020
INVENTOR(S)      : McNaughton et al.

It is certified that error appears in the above-identified patent and that said Letters Patent is hereby corrected as shown below:

In the Claims

Claim 24, Column 63, Line 19, delete "or" and replace with --of--.

Signed and Sealed this
Fifth Day of May, 2020

Andrei Iancu
*Director of the United States Patent and Trademark Office*

SEQUENCE LISTING

<160> NUMBER OF SEQ ID NOS: 26

<210> SEQ ID NO 1
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 1

Leu Asp Ile Leu Val Ser Arg Ser Leu Lys Met Arg Gly Gln Ala Phe
1               5                   10                  15

Val Ile Phe

<210> SEQ ID NO 2
<211> LENGTH: 13
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(2)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Thr, Asn, Gln, Lys, Arg, or His
<220> FEATURE:
<221> NAME/KEY: MISC_FEATURE
<222> LOCATION: (7)..(7)
<223> OTHER INFORMATION: Xaa is Thr, Asn, Gln, Ser, Arg, or His
<220> FEATURE:
<221> NAME/KEY: MISC_FEATURE
<222> LOCATION: (8)..(8)
<223> OTHER INFORMATION: Xaa is Pro, Tyr, Trp, Phe, Leu, Ile, Val, or
      Ala
<220> FEATURE:
<221> NAME/KEY: MISC_FEATURE
<222> LOCATION: (10)..(13)
<223> OTHER INFORMATION: Xaa is any amino acid

<400> SEQUENCE: 2

Xaa Xaa Pro Arg Xaa Arg Xaa Xaa Arg Xaa Xaa Xaa Xaa
1               5                   10

<210> SEQ ID NO 3
<211> LENGTH: 13
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(2)
<223> OTHER INFORMATION: X is any amino acid
<220> FEATURE:
<221> NAME/KEY: MISC_FEATURE
<222> LOCATION: (5)..(5)
<223> OTHER INFORMATION: Xaa is Thr, Asn, or Gln
<220> FEATURE:
<221> NAME/KEY: MISC_FEATURE
<222> LOCATION: (7)..(7)
<223> OTHER INFORMATION: Xaa is Thr, Asn, Gln, or Ser
<220> FEATURE:
<221> NAME/KEY: MISC_FEATURE
<222> LOCATION: (8)..(8)
<223> OTHER INFORMATION: Xaa is Pro, Tyr, Trp, or Phe
<220> FEATURE:
<221> NAME/KEY: MISC_FEATURE
<222> LOCATION: (10)..(13)
<223> OTHER INFORMATION: Xaa is any amino acid

<400> SEQUENCE: 3

Xaa Xaa Pro Arg Xaa Arg Xaa Xaa Arg Xaa Xaa Xaa Xaa
1               5                   10

<210> SEQ ID NO 4
<211> LENGTH: 13
<212> TYPE: PRT
<213> ORGANISM: Artificial Sequence
<220> FEATURE:
<223> OTHER INFORMATION: SYNTHESIZED

```
<220> FEATURE:
<221> NAME/KEY: MISC_FEATURE
<222> LOCATION: (1)..(2)
<223> OTHER INFORMATION: Xaa is any amino acid
<220> FEATURE:
<221> NAME/KEY: MISC_FEATURE
<222> LOCATION: (10)..(13)
<223> OTHER INFORMATION: Xaa is any amino acid

<400> SEQUENCE: 4

Xaa Xaa Pro Arg Thr Arg Thr Pro Arg Xaa Xaa Xaa Xaa
1               5                   10

<210> SEQ ID NO 5
<211> LENGTH: 19
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(5)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Thr, Asn, Gln, Lys, Arg, or His
<220> FEATURE:
<221> NAME/KEY: MISC_FEATURE
<222> LOCATION: (10)..(10)
<223> OTHER INFORMATION: Xaa is Thr, Asn, Gln, Ser, Arg, or His
<220> FEATURE:
<221> NAME/KEY: MISC_FEATURE
<222> LOCATION: (11)..(11)
<223> OTHER INFORMATION: Xaa is Pro, Tyr, Trp, Phe, Leu, Ile, Val, or
      Ala
<220> FEATURE:
<221> NAME/KEY: MISC_FEATURE
<222> LOCATION: (13)..(19)
<223> OTHER INFORMATION: Xaa is any amino acid

<400> SEQUENCE: 5

Xaa Xaa Xaa Xaa Xaa Pro Arg Xaa Arg Xaa Xaa Arg Xaa Xaa Xaa Xaa
1               5                   10                  15

Xaa Xaa Xaa

<210> SEQ ID NO 6
<211> LENGTH: 19
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(5)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Thr, Asn, or Gln
<220> FEATURE:
<221> NAME/KEY: MISC_FEATURE
<222> LOCATION: (10)..(10)
<223> OTHER INFORMATION: Xaa is Thr, Asn, Gln, or Ser
<220> FEATURE:
<221> NAME/KEY: MISC_FEATURE
<222> LOCATION: (11)..(11)
<223> OTHER INFORMATION: Xaa is Pro, Tyr, Trp, or Phe
<220> FEATURE:
<221> NAME/KEY: MISC_FEATURE
<222> LOCATION: (13)..(19)
<223> OTHER INFORMATION: Xaa is any amino acid

<400> SEQUENCE: 6
```

```
Xaa Xaa Xaa Xaa Xaa Pro Arg Xaa Arg Xaa Xaa Arg Xaa Xaa Xaa Xaa
1               5                   10                  15

Xaa Xaa Xaa

<210> SEQ ID NO 7
<211> LENGTH: 19
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(5)
<223> OTHER INFORMATION: Xaa is any amino acid
<220> FEATURE:
<221> NAME/KEY: MISC_FEATURE
<222> LOCATION: (13)..(19)
<223> OTHER INFORMATION: Xaa is any amino acid

<400> SEQUENCE: 7

Xaa Xaa Xaa Xaa Xaa Pro Arg Thr Arg Thr Pro Arg Xaa Xaa Xaa Xaa
1               5                   10                  15

Xaa Xaa Xaa

<210> SEQ ID NO 8
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 8

Leu Asp Ile Leu Val Pro Arg His Arg Thr Pro Arg Gly Gln Ala Phe
1               5                   10                  15

Val Ile Phe

<210> SEQ ID NO 9
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 9

Leu Asp Ile Leu Val Pro Arg Lys Arg Thr Pro Arg Gly Gln Ala Phe
1               5                   10                  15

Val Ile Phe

<210> SEQ ID NO 10
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 10

Leu Asp Ile Leu Val Pro Arg Met Arg Arg Pro Arg Gly Gln Ala Phe
1               5                   10                  15

Val Ile Phe

<210> SEQ ID NO 11
<211> LENGTH: 19
<212> TYPE: PRT
<213> ORGANISM: Artificial Sequence
```

-continued

<220> FEATURE:
<223> OTHER INFORMATION: SYNTHESIZED

<400> SEQUENCE: 11

Leu Asp Ile Leu Val Pro Arg Met Arg Thr Pro Arg Gly Gln Ala Phe
1               5                   10                  15

Val Ile Phe

<210> SEQ ID NO 12
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 12

Leu Asp Ile Leu Val Pro Arg Pro Arg Arg Pro Arg Gly Gln Ala Phe
1               5                   10                  15

Val Ile Phe

<210> SEQ ID NO 13
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 13

Leu Asp Ile Leu Val Pro Arg Pro Arg Thr Pro Arg Gly Gln Ala Phe
1               5                   10                  15

Val Ile Phe

<210> SEQ ID NO 14
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 14

Leu Asp Ile Leu Val Pro Arg Pro Arg Thr Tyr Arg Gly Gln Ala Phe
1               5                   10                  15

Val Ile Phe

<210> SEQ ID NO 15
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 15

Leu Asp Ile Leu Val Pro Arg Gln Arg Thr Pro Arg Gly Gln Ala Phe
1               5                   10                  15

Val Ile Phe

<210> SEQ ID NO 16
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 16

```
Leu Asp Ile Leu Val Pro Arg Arg Gln Pro Arg Gly Gln Ala Phe
1               5                   10                  15

Val Ile Phe

<210> SEQ ID NO 17
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 17

Leu Asp Ile Leu Val Pro Arg Arg Arg Thr Pro Arg Gly Gln Ala Phe
1               5                   10                  15

Val Ile Phe

<210> SEQ ID NO 18
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 18

Leu Asp Ile Leu Val Pro Arg Arg Arg Thr Trp Arg Gly Gln Ala Phe
1               5                   10                  15

Val Ile Phe

<210> SEQ ID NO 19
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 19

Leu Asp Ile Leu Val Pro Arg Arg Arg Thr Tyr Arg Gly Gln Ala Phe
1               5                   10                  15

Val Ile Phe

<210> SEQ ID NO 20
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 20

Leu Asp Ile Leu Val Pro Arg Thr Arg Asn Pro Arg Gly Gln Ala Phe
1               5                   10                  15

Val Ile Phe

<210> SEQ ID NO 21
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 21

Leu Asp Ile Leu Val Pro Arg Thr Arg Arg Pro Arg Gly Gln Ala Phe
1               5                   10                  15
```

Val Ile Phe

<210> SEQ ID NO 22
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 22

Leu Asp Ile Leu Val Pro Arg Thr Arg Thr Pro Arg Gly Gln Ala Phe
1               5                   10                  15

Val Ile Phe

<210> SEQ ID NO 23
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 23

Leu Asp Ile Leu Val Pro Arg Thr Arg Val Pro Arg Gly Gln Ala Phe
1               5                   10                  15

Val Ile Phe

<210> SEQ ID NO 24
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 24

Leu Asp Ile Leu Val Pro Arg Tyr Arg Thr Pro Arg Gly Gln Ala Phe
1               5                   10                  15

Val Ile Phe

<210> SEQ ID NO 25
<211> LENGTH: 31
<212> TYPE: RNA
<213> ORGANISM: Lentivirus Human Immunodeficiency Virus 1

<400> SEQUENCE: 25
ggccagaucu ggcccuggga ggccucuggc c                              31

<210> SEQ ID NO 26
<211> LENGTH: 282
<212> TYPE: PRT
<213> ORGANISM: Homo sapiens

<400> SEQUENCE: 26

Met Ala Val Pro Glu Thr Arg Pro Asn His Thr Ile Tyr Ile Asn Asn
1               5                   10                  15

Leu Asn Glu Lys Ile Lys Lys Asp Glu Leu Lys Lys Ser Leu Tyr Ala
                20                  25                  30

Ile Phe Ser Gln Phe Gly Gln Ile Leu Asp Ile Leu Val Ser Arg Ser
            35                  40                  45

Leu Lys Met Arg Gly Gln Ala Phe Val Ile Phe Lys Glu Val Ser Ser
        50                  55                  60

Ala Thr Asn Ala Leu Arg Ser Met Gln Gly Phe Pro Phe Tyr Asp Lys
65                  70                  75                  80

```
Pro Met Arg Ile Gln Tyr Ala Lys Thr Asp Ser Asp Ile Ile Ala Lys
                85                  90                  95

Met Lys Gly Thr Phe Val Glu Arg Asp Arg Lys Arg Glu Lys Arg Lys
            100                 105                 110

Pro Lys Ser Gln Glu Thr Pro Ala Thr Lys Lys Ala Val Gln Gly Gly
            115                 120                 125

Gly Ala Thr Pro Val Val Gly Ala Val Gln Gly Pro Val Pro Gly Met
            130                 135                 140

Pro Pro Met Thr Gln Ala Pro Arg Ile Met His His Met Pro Gly Gln
145                 150                 155                 160

Pro Pro Tyr Met Pro Pro Pro Gly Met Ile Pro Pro Pro Gly Leu Ala
                165                 170                 175

Pro Gly Gln Ile Pro Pro Gly Ala Met Pro Pro Gln Gln Leu Met Pro
                180                 185                 190

Gly Gln Met Pro Pro Ala Gln Pro Leu Ser Glu Asn Pro Pro Asn His
            195                 200                 205

Ile Leu Phe Leu Thr Asn Leu Pro Glu Glu Thr Asn Glu Leu Met Leu
            210                 215                 220

Ser Met Leu Phe Asn Gln Phe Pro Gly Phe Lys Glu Val Arg Leu Val
225                 230                 235                 240

Pro Gly Arg His Asp Ile Ala Phe Val Glu Phe Asp Asn Glu Val Gln
                245                 250                 255

Ala Gly Ala Ala Arg Asp Ala Leu Gln Gly Phe Lys Ile Thr Gln Asn
                260                 265                 270

Asn Ala Met Lys Ile Ser Phe Ala Lys Lys
            275                 280
```